United States Patent
Johnson et al.

(10) Patent No.: US 6,939,871 B2
(45) Date of Patent: Sep. 6, 2005

(54) BENZOXAZINONE DERIVATIVES, THEIR PREPARATION AND USE

(75) Inventors: Christopher Norbert Johnson, Harlow (GB); Harshad Kantilal Rami, Harlow (GB); Geoffrey Stemp, Harlow (GB); Kevin Thewlis, Harlow (GB); Mervyn Thompson, Harlow (GB); Antonio Keuok Keong Vong, Harlow (GB)

(73) Assignee: SmithKline Beecham p.l.c., Brentford (GB)

(*) Notice: Subject to any disclaimer, the term of this patent is extended or adjusted under 35 U.S.C. 154(b) by 0 days.

(21) Appl. No.: 10/415,119

(22) PCT Filed: Oct. 22, 2001

(86) PCT No.: PCT/EP01/12344

§ 371 (c)(1),
(2), (4) Date: Oct. 16, 2003

(87) PCT Pub. No.: WO02/34754

PCT Pub. Date: May 2, 2002

(65) Prior Publication Data

US 2004/0063704 A1 Apr. 1, 2004

(30) Foreign Application Priority Data

Oct. 26, 2000 (GB) .................................. 0026224
May 15, 2001 (GB) .................................. 0111858

(51) Int. Cl.$^7$ .................. C07D 413/10; A61K 31/538; A61P 25/18; A61P 25/22
(52) U.S. Cl. .................................. 514/230.5; 544/105
(58) Field of Search .................. 544/105; 514/230.5

(56) References Cited

FOREIGN PATENT DOCUMENTS

| EP | 0 900 792 A1 | 3/1999 |
|---|---|---|
| WO | WO 97/45419 | 12/1997 |
| WO | WO 00/40580 | 7/2000 |
| WO | WO 00/40581 | 7/2000 |

Primary Examiner—Mark L. Berch
Assistant Examiner—Kahsay Habte
(74) Attorney, Agent, or Firm—Wayne J. Dustman; Stephen Venetianer

(57) ABSTRACT

The present invention relates to novel compounds of formula (I) or a pharmaceutically acceptable salt thereof, wherein Ar is phenyl, naphthyl, a monocyclic heteroaromatic group or a bicyclic heteroaromatic group, said Ar group being optionally substituted by 1–4 substituents, which may be the same or different, and which are selected from the group consisting of: halogen, hydroxy, cyano, nitro, trifluoromethyl, trifluoromethoxy, C1–6alkyl, trifluoromethanesulfonyloxy, pentafluoroethyl, C1–6alkoxy, arylC1–6alkoxy, C1–6alkylthio, C1–6alkoxyC1–6-alkyl, C3–7cycloalkylC1–6alkoxy, C1–6alkanoyl, C1–6alkoxycarbonyl, C1–6alkylsulfonyl, C1–6alkylsulfinyl, C1–6alkylsulfonyloxy, C1–6alkylsulfonylC1–6alkyl, arylsulfonyl, arylsulfonyloxy, arylsulfonylC1–6alkyl, C1–6alkylsulfonamido, C1–6alkylamido, C1–6alkylsulfonamidoC1–6alkyl, C1–6alkylamidoC1–6alkyl, arylsulfonamido, arylcarboxamido, alkylsulfonamidoC1–6alkyl, arylcarboxamidoC1–6alkyl, aroyl, arolC1–6alkyl, arylC1–6alkanoyl, a group R<3>OCO(CH2)s, R<3>CON(R<4>)(CH2)s, R<3>R<4>NCO(CH2)s or R<3>R<4>NSO2(CH2) where each of R<3> and R<4> independently represents a hydrogen atom or C1–4alkyl or R<3> and R<4> form part of a C3–6azacyloalkane or C3–6(2-oxo)azacycloalkane ring and s represents zero or an integer from 1 to 4, and a group Ar<1>Z, wherein Z represents a single bond, O, S or CH2 and Ar<1> represents a phenyl or a monocyclic heteroaromatic group, said Ar<1> group being optionally substituted by 1–3 substituents, which may be the same or different, and which are selected from the group consisting of a halogen, hydroxy, cyano, trifluoromethyl, C1–6alkyl, C1–6alkoxy or C1–6alkanoyl; when Ar is a phenyl or a monocyclic heteroaromatic group, substitutents positioned ortho to one another may be linked to form a 5- or 6-membered ring; R<1> is hydrogen, C1–6alkyl, C3–6alkenyl, C3–6alkynyl or arylC1–6alkyl; R<2> is halogen, C1–6alkyl, cyano, CF3, C1–6alkanoyl, C1–6alkoxy or hydroxy; X is CH or N; Y is a single bond, O, or C=O; p is 0, 1 or 2; r is 0, 1, 2 or 3; m is 2, 3 or 4; n and q are independently 1 or 2. Processes for preparing the compounds, pharmaceutical compositions containing them and their use as medicaments for various CNS disorders, including deression and/or anxiety, are also disclosed.

16 Claims, No Drawings

BENZOXAZINONE DERIVATIVES, THEIR PREPARATION AND USE

The present invention relates to novel compounds, processes for their preparation, pharmaceutical compositions containing the same and their use as medicaments. More particularly this invention relates to novel benzoxazinone derivatives and their utility in the treatment and/or prophylaxis of CNS and other disorders.

WO 97/45419 discloses a series of benzoxazinone compounds as dopamine $D_4$ receptor antagonists which are claimed to be useful in the treatment of psychosis and schizophrenia. EP 0900 792 A1 discloses a series of piperazine and piperidine derivatives as 5-HT$_1$ receptor agonists which are claimed to be useful for treating CNS disorders.

Artigas (Trends in Pharmacological Sciences, Vol. 14, 262, 1993) suggests that the co-administration of a 5-HT$_{1A}$ receptor antagonist and a selective serotonin reuptake inhibitor (SSRI) may give rise to an improvement in antidepressant efficacy. Patent applications WO 00/40580 and WO 00/40581 both disclose a series of benzoxazine derivatives that are claimed to possess such a combined activity profile.

A novel series of benzoxazinone compounds has now been found that possess high affinity for 5-HT$_1$ type receptors and/or potent serotonin reuptake inhibition activity. The present invention therefore provides, in a first aspect, a compound of formula (I) or a pharmaceutically acceptable salt thereof:

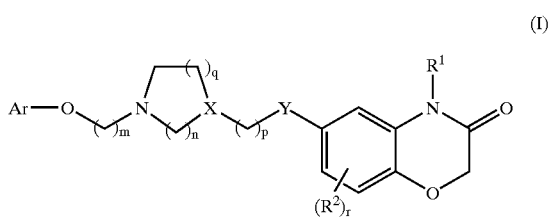

(I)

in which
Ar is phenyl, naphthyl, a monocyclic heteroaromatic group or a bicyclic heteroaromatic group, said Ar group being optionally substituted by 1–4 substituents, which may be the same or different, and which are selected from the group consisting of:
halogen, hydroxy, cyano, nitro, trifluoromethyl, trifluoromethoxy, $C_{1-6}$alkyl, trifluoromethanesulfonyloxy, pentafluoroethyl, $C_{1-6}$alkoxy, aryl$C_{1-6}$alkoxy, $C_{1-6}$alkylthio, $C_{1-6}$alkoxy$C_{1-6}$alkyl, $C_{3-7}$cycloalkyl$C_{1-6}$alkoxy, $C_{1-6}$alkanoyl, $C_{1-6}$alkoxycarbonyl, $C_{1-6}$alkylsulfonyl, $C_{1-6}$alkylsulfinyl, $C_{1-6}$alkylsulfonyloxy, $C_{1-6}$alkylsulfonyl$C_{1-6}$alkyl, arylsulfonyl, arylsulfonyloxy, arylsulfonyl$C_{1-6}$alkyl, $C_{1-6}$alkylsulfonamido, $C_{1-6}$alkylamido, $C_{1-6}$alkylsulfonamido$C_{1-6}$alkyl, $C_{1-6}$alkylamido$C_{1-6}$alkyl, arylsulfonamido, arylcarboxamido, arylsulfonamido$C_{1-6}$alkyl, arylcarboxamido$C_{1-6}$alkyl, aroyl, aroyl$C_{1-16}$alkyl, aryl$C_{1-6}$alkanoyl, a group $R^3OCO(CH_2)_s$, $R^3CON(R^4)(CH_2)_s$, $R^3R^4NCO(CH_2)_s$ or $R^3R^4NSO_2(CH_2)_s$ where each of $R^3$ and $R^4$ independently represents a hydrogen atom or $C_{1-4}$alkyl or $R^3$ and $R^4$ form part of a $C_{3-6}$azacyloalkane or $C_{3-6}$(2-oxo)azacycloalkane ring and s represents zero or an integer from 1 to 4, and a group $Ar^1$-Z, wherein Z represents a single bond, O, S or $CH_2$ and $Ar^1$ represents a phenyl or a monocyclic heteroaromatic group, said $Ar^1$ group being optionally substituted by 1–3 substituents, which may be the same or different, and which are selected from the group consisting of a halogen, hydroxy, cyano, trifluoromethyl, $C_{1-6}$alkyl, $C_{1-6}$alkoxy or $C_{1-6}$alkanoyl;
when Ar is a phenyl or a monocyclic heteroaromatic group, substituents positioned ortho to one another may be linked to form a 5- or 6-membered ring;
$R^1$ is hydrogen $C_{1-6}$alkyl, $C_{3-6}$alkenyl, $C_{3-6}$alkynyl or aryl$C_{1-6}$alkyl;
$R^2$ is halogen, $C_{1-6}$alkyl, cyano, $CF_3$, $C_{1-6}$alkanoyl, $C_{1-6}$alkoxy or hydroxy.
X is CH or N;
Y is a single bond, O, or C=O;
p is 0, 1 or 2;
r is 0, 1, 2 or 3;
m is 2, 3 or 4;
n and q are independently 1 or 2.

Alkyl groups which may be employed, whether alone or part of another group, include methyl, ethyl, n-propyl, n-butyl, n-pentyl, n-hexyl and any branched isomers thereof such as isopropyl, t-butyl, sec-butyl, and the like. "$C_{1-4}$ alkyl" and "$C_{1-6}$alkyl" respectively refer to alkyl groups having from one to four and from one to six carbon atoms, in all isomeric forms. Thus, $C_{1-4}$alkyl would include: methyl, ethyl, propyl, isopropyl, butyl, isobutyl, sec-butyl and tert-butyl. $C_{1-6}$alkyl would include, in addition, pentyl, neopentyl, sec-pentyl, n-pentyl, isopentyl, tert-pentyl and hexyl.

The term "halogen" is used herein to describe, unless otherwise stated, a group selected from fluorine, chlorine, bromine and iodine.

Where used herein the term "aryl", whether alone or as part of another group, is intended, unless otherwise stated, to denote an aromatic carbocyclic or heterocyclic group such as phenyl, pyrimidine, pyrazine or naphthyl, optionally substituted by one or more halogen, $C_{1-6}$alkyl, $CF_3$, cyano, hydroxy, $C_{1-6}$alkanoyl, or $C_{1-6}$alkoxy. Where used herein the term naphthyl, whether alone or as part of another group, is intended, unless otherwise stated, to denote both 1-naphthyl and 2-naphthyl groups.

The term "monocyclic heteroaromatic group" is used to describe stable 5 or 6 membered heteroaromatic rings containing 1 to 4 heteroatoms selected from oxygen, nitrogen and sulfur. Suitable examples of such groups include thienyl, furanyl, pyrrolyl, triazolyl, imidazolyl, pyrazolyl, oxazolyl, isoxazolyl, thiazolyl, oxadiazolyl, isothiazolyl, isoxazolyl, thiadiazolyl, pyridyl, pyrimidyl, triazinyl, pyridazyl and pyrazinyl.

The term "bicyclic heteroaromatic group" is used to describe stable 6,5 and 6,6 heteroaromatic rings containing 1 to 4 heteroatoms selected from oxygen, nitrogen and sulfur. Suitable examples of such groups include indolyl, quinolinyl, isoquinolinyl, benzofuranyl, benzothienyl, benzimidazolyl, indazolyl, 4-, 5-, 6- or 7-azaindolyl, benzothiazolyl, benzoxazolyl, benzisoxazolyl, benzisothiazolyl, quinazolinyl, quinoxalinyl, cinnolinyl and naphthyridinyl.

The term "$C_{1-6}$alkoxy" refers to a straight chain or branched chain alkoxy (or "alkyloxy") group having from one to six carbon atoms, such as methoxy, ethoxy, propoxy, isopropoxy, butoxy, isobutoxy, sec-butoxy, tert-butoxy, pentoxy, neopentoxy, sec-pentoxy, n-pentoxy, isopentoxy, tert-pentoxy and hexoxy.

The term "$C_{1-6}$alkylthio" refers to a straight chain or branched chain alkylthio group having from one to six carbon atoms, such as methylthio, ethylthio, propylthio, isopropylthio, butylthio, isobutylthio, sec-butylthio, tert-butylthio, pentylthio, neopentylthio, sec-pentylthio, n-pentylthio, isopentylthio, tert-pentylthio and hexylthio.

The term "arylC$_{1-6}$alkoxy" refers to an aryl group which is linked by a C$_{1-6}$alkoxy group. Examples include phenylmethoxy, phenylethoxy, naphthymethoxy, naphthylethoxy, phenylpropoxy, naphthylpropoxy, phenylbutoxy and naphthylpentoxy.

The term "C$_{3-7}$cycloalkylC$_{1-6}$alkoxy" refers to a cycloalkyl group consisting of from 3 to 7 carbon atoms (for example cyclopropane, cyclobutane, cyclopentane, cyclohexane and cycloheptane) attached to an C$_{1-6}$alkoxy group.

The term "C$_{1-6}$alkanoyl" refers to an alkanoyl group having from 1 to 6 carbon atoms, such as methanol (or "formyl"), ethanoyl (or "acetyl"), propanoyl, butanoyl, pentanoyl and hexanoyl.

The term "aroyl" refers to a group having the formula "aryl-CO" wherein "aryl" is as defined above.

The term "C$_{3-6}$azacyloalkane ring" refers to a cycloalkane ring containing from 3 to 6 carbon atoms, wherein one or more of the carbon atoms may be replaced by a nitrogen atom. Examples include aziridinyl, azetidinyl, pyrrolidinyl, piperidinyl, piperazinyl and azepanyl.

The term "C$_{3-6}$(2-oxo)azacycloalkane ring" refers to a C$_{3-6}$azacyloalkane ring which also contains a C=O group, e.g. a cyclic amide or a lactam. Examples include aziridin-2-one, azetidinone, pyrrolidinone, piperidinone and azepanone.

The term "C$_{3-6}$alkenyl" refers to an unsaturated hydrocarbon group containing one or more C=C bonds and having from three to six carbon atoms, in all isomeric forms, such as propenyl, butenyl, pentenyl, and hexenyl.

The term "C$_{3-6}$alkynyl" refers to an unsaturated hydrocarbon group containing one or more triple C—C bonds, having from three to six carbon atoms, in all isomeric forms, such as propynyl, butanediylidyne, butenylidyne, butylidyne, pentenynyl, and pentylidyne.

Preferably Ar is phenyl, naphthyl, indolyl, quinolinyl, quinazolinyl, indazolyl, isoquinolinyl, cinnolinyl or benzofuranyl, said groups being optionally substituted as defined above.

When a substituent on Ar is a further group Ar$^1$-Z. Ar$^1$ is preferably a monocyclic heteroaromatic group (particularly isoxazolyl), optionally substituted as defined above. Preferably Z is a single bond.

When the group Ar is phenyl or a monocyclic heteroaromatic group and optional substituents on the group Ar are positioned ortho to one another are linked to form a 5- or 6-membered ring, preferred examples of the resulting bicyclic system include 2,3-dihydrobenzo[b]furanyl, 3,4-dihydro-2H-benzo[b]pyranyl, 2,2-dimethyl-2,3-dihydrobenzo[b]furanyl, 2,2-dimethyl-3,4-dihydro-2H-benzo[b]pyranyl, or 5-oxo-5,6,7,8-tetrahydronaphthyl, the said groups being optionally further substituted as defined above.

Preferred optional substituents for Ar are halogen (particularly fluoro or chloro), C$_{1-6}$alkyl (particularly methyl, ethyl and propyl), cyano, CF$_3$, C$_{1-6}$alkoxy (particularly methoxy, ethoxy or isopropoxy), C$_{1-6}$alkanoyl or a group Ar$^1$-Z as defined above.

Particularly preferred Ar groups, including optional substituents, are 4-indolyl, 4-indolyl(2-CN), 5-quinolinyl, 5-quinolinyl(2-Me), 8-quinolinyl, 1-isoquinolinyl, naphthyl, phenyl(2-CN), phenyl(2,3-dichloro), phenyl(3-Br), phenyl (3-Me), phenyl(3-CF$_3$), phenyl(2-propyl), phenyl(2-CN, 4-F), phenyl(2-(5-isoxazolyl), phenyl(3-ethyl-4-Cl), 2,2-dimethyl-2,3-dihydrobenzo[b]furan-7-yl, (5-F)-2,2-dimethyl-2,3-dihydrobenzo[b]furan-7-yl, (6-F)-3,4-dihydro-2H-benzo[b]pyranyl, (2,2-dimethyl)3,4-dihydro-2H-benzo[b]pyranyl, 5-oxo-5,6,7,8-tetrahydronaphthyl-1-yl, 7-(2,3-dihydrobenzofuranyl), 7-(2-methyl)benzo[b] furanyl, 7-benzo[b]furanyl, 5-quinolinyl(2-Me, 8-Cl), 5-quinolinyl(2-Me, 8-F), 5-quinolinyl(2-Me, 7-Cl), 5-quinolinyl(2-Me, 7-F) and 5-quinazolinyl(2-Me).

Most particularly preferred Ar groups, including optional substituents, are 5-quinolinyl(2-Me), 5-quinolinyl(2-Me, 7-Cl), 5-quinolinyl(2-Me, 7-F) and 5-quinazolinyl(2-Me).

When R$^1$ is C$_{1-6}$alkyl a preferred group is methyl. Preferably R$^1$ is hydrogen or methyl.

When r is other than 0, preferred substituents include halogen (particularly fluoro or chloro), C$_{1-6}$alkyl (particularly methyl or ethyl), cyano, C$_{1-6}$alkanoyl or CF$_3$.

Preferably m is 2.

When n is 2, preferably q is 1.

Preferably, r is 0, 1 or 2.

Preferably R$^2$ is halogen, particularly fluoro.

Preferably Y is oxygen or is a single bond. When Y is oxygen, preferably p is 0 or 1. When Y is a single bond, it is preferred that p is 1, so that X and the benzoxazinone group are linked by a CH$_2$ group.

Preferred compounds of this invention are examples E1–E167 (as described below) and pharmaceutically acceptable salts thereof. Particularly preferred compounds according to this invention are:

6-(4-(1-(2-(4-1H-Indolyloxy)ethyl)piperidinyl)oxy)-4H-benzo[1,4]oxazin-3-one, 6-(4-(1-(2-(4-(2-Cyano)-1H-indolyloxy)ethyl)piperidinyl) oxy)-4H-benzo[1,4]oxazin-3-one, 6-(4-(1-(3-(2-(5-Isoxazolyl)phenoxy)propyl)piperidinyl) oxy)-4H-benzo[1,4]oxazin-3-one, 6-(4-(1-(2-(5-Quinolinyloxy)ethyl)piperidinyl)methyl)-4H-benzo[1,4]oxazin-3-one, 6-(4-(1-(3-(2-Cyanophenoxy)propyl)piperidinyl)oxy)-4H-benzo[1,4]oxazin-3-one, 6-(4-(1-(3-(7-(2,2-Dimethyl-2,3-dihydro)benzo[b] furanyloxy)propyl)piperidinyl)-oxy)-4H-benzo[1,4] oxazin-3-one, 6-(4-(1-(2-(7-(2,2-Dimethyl-2,3-dihydro)benzo[b] furanyloxy)ethyl)piperidinyl)oxy)-4-methyl-4H-benzo[1, 4]oxazin-3-one, 6-(4-(1-(2-(1-naphthyloxy)ethyl)piperidinyl)oxy)-4-methyl-4H-benzo[1,4]oxazin-3-one, (±)-6-(3-(1-(3-(2-Cyanophenoxy)propyl)piperidinyl) methoxy)-4H-benzo[1,4]oxazin-3-one, (±)-6-(3-(1-(3-(2-Cyanophenoxy)propyl)pyrrolidinyl) methoxy)-4H-benzo [1,4]oxazin-3)-one, 6-(4-(1-(3-(2-(5-Isoxazolyl)phenoxy)propyl)piperazinyl) methyl)-4H-benzo[1,4]oxazin-3-one, 6-(4-(1-(2-(5-(2-Methyl)quinolinyloxy)ethyl)piperidinyl) methyl)-4H-benzo[1,4]oxazin-3-one, 6-(4-(1-(2-(5-(3-Methyl)quinolinyloxy)ethyl)piperidinyl) methyl)-4H-benzo[1,4]oxazin-3-one, 6-(4-(1-(2-(5-quinolinyloxy)ethyl)piperidinyl)methyl)-4H-benzo[1,4]oxazin-3-one, 6-(4-(1-(2-(4-(1,2-Dihydro)benzo[b]furanyloxy)ethyl) piperidinyl)methyl)-4H-benzo[1,4]oxazin-3-one, 6-(4-(1-(2-(4-(1H)-Indazolyloxy)ethyl)piperidinyl)methyl)-4H-benzo[1,4]oxazin-3-one, 6-(4-(1-(2-(5-(2-Methyl)quinolinyloxy)ethyl)piperidinyl) oxy)-4H-benzo[1,4]oxazin-3-one, 4-Methyl-6-(4-(1-(2-(5-(2-methyl)quinolinyloxy)ethyl) piperidinyl)oxy)-4H-benzo[1,4]oxazin-3-one, 6-(4-(1-(2-(5-(2-Methyl)quinolinyloxy)ethyl)piperazinyl) methyl)-4H-benzo[1,4]oxazin-3-one, 6-(4-(1-(3-(5-(2-Methyl)quinolinyloxy)propyl)piperidinyl) methyl)-4H-benzo[1,4]oxazin-3-one,
6-(4-(1-(3-(5-(2-Methyl)quinolinyloxy)propyl)piperazinyl) methyl)-4H-benzo[1,4]oxazin-3-one,
6-(4-(1-(3-(5-(2-Methyl)quinolinyloxy)propyl)piperidinyl) oxy)-4H-benzo[1,4]oxazin-3-one,
4-Methyl-6-(4-(1-(3-(5-(2-methyl)quinolinyloxy)propyl) piperidinyl)oxy)-4H-benzo[1,4]oxazin-3-one,
4-Methyl-6-(4-(1-(2-(5-(2-methyl)quinolinyloxy)ethyl) piperidinyl)methyl)-4H-benzo[1,4]oxazin-3-one,
6-(4-(1-(2-(5-(8-Chloro-2-methyl)quinolinyloxy)ethyl) piperidinyl)methyl)-4H-benzo[1,4]oxazin-3-one,
4-Methyl-6-(4-(1-(3-(5-(2-methyl)quinolinyloxy)propyl) piperidinyl)-methyl)-4H-benzo[1,4]oxazin-3-one,
6-(4-(1-(2-(5-(8-Chloro-2-methyl)quinolinyloxy)ethyl) piperidinyl)methyl)-4-methyl-4H-benzo[1,4]oxazin-3-one,
6-(4-(1-(2-(5-(8-Fluoro-2-methyl)quinolinyloxy)ethyl) piperidinyl)methyl)-4H-benzo[1,4]oxazin-3-one,
6-(4-(1-(2-(5-(8-Fluoro-2-methyl)quinolinyloxy)ethyl) piperidinyl)methyl)-4-methyl-4H-benzo[1,4]oxazin-3-one,
6-(4-(1-(2-(5-(8-Fluoro-2-methyl)quinolinyloxy)ethyl) piperidinyl)oxy)-4H-benzo[1,4]oxazin-3-one,
6-(4-(1-(2-(5-(8-Fluoro-2-methyl)quinolinyloxy)ethyl) piperidinyl)oxy)-4-methyl-4H-benzo[1,4]oxazin-3-one,
6-(4-(1-(2-(5-(7-Chloro-2-methyl)quinolinyloxy)ethyl) piperidinyl)methyl)-4H-benzo[1,4]oxazin-3-one,
6-(4-(1-(2-(5-(7-Chloro-2-methyl)quinolinyloxy)ethyl) piperidinyl)methyl)-4-methyl-4H-benzo[1,4]oxazin-3-one,
6-(4-(1-(2-(5-(7-Chloro-2-methyl)quinolinyloxy)ethyl) piperidinyl)oxy)-4H-benzo[1,4]oxazin-3-one,
6-(4-(1-(2-(5-(7-Chloro-2-methyl)quinolinyloxy)ethyl) piperidinyl)oxy)-4-methyl-4H-benzo[1,4]oxazin-3-one,
6-(4-(1-(2-(5-(7-Chloro-2-methyl)quinolinyloxy)ethyl) piperazinyl)methyl)-4H-benzo[1,4]oxazin-3-one,
6-(4-(1-(3-(5-(7-Chloro-2-methyl)quinolinyloxy)propyl) piperidinyl)oxy)-4H-benzo[1,4]oxazin-3-one,
6-(4-(1-(3-(5-(7-Chloro-2-methyl)quinolinyloxy)propyl) piperidinyl)oxy)-4-methyl-4H-benzo[1,4]oxazin-3-one,
6-(4-(1-(2-(5-(2-Methyl)quinolinyloxy)ethyl)piperidinyl) methyl)-4-(2-propyl)-4H-benzo[1,4]oxazin-3-one,
6-(4-(1-(2-(5-(2-Methyl)quinazolinyloxy)ethyl)piperidinyl) methyl)-4H-benzo[1,4]-oxazin-3-one,
6-(4-(1-(2-(5-(7-Fluoro-2-methyl)quinolinyloxy)ethyl) piperidinyl)methyl)-4H-benzo[1,4]oxazin-3-one,
7-Fluoro-6-(4-(1-(2-(5-(2-methyl)quinolinyloxy)ethyl) piperidinyl)methyl)-4H-benzo[1,4]oxazin-3-one,
8-Fluoro-4-methyl-6-(4-(1-(2-(5-(2-methyl)quinolinyloxy) ethyl)piperidinyl)methyl)-4H-benzo[1,4]oxazin-3-one,
8-Fluoro-6-(4-(1-(2-(5-(2-methyl)quinolinyloxy)ethyl) piperidinyl)methyl)-4H-benzo[1,4]oxazin-3-one,
7,8-Difluoro-6-(4-(1-(2-(5-(2-methyl)quinolinyloxy)ethyl) piperazinyl)methyl)-4H-benzo[1,4]oxazin-3-one,
4-Ethyl-6-{1-[2-(2-methyl-quinolin-5-yloxy)-ethyl]-piperidin-4-ylmethyl}-4H-benzo[1,4]oxazin-3-one
and pharmaceutically acceptable salts thereof.

The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in *J. Pharm. Sci.*, 1977, 66, 1–19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Certain of the compounds of formula (I) may form acid addition salts with one or more equivalents of the acid. The present invention includes within its scope all possible stoichiometric and non-stoichiometric forms.

The compounds of formula (I) may be prepared in crystalline or non-crystalline form, and, if crystalline, may optionally be hydrated or solvated. This invention includes within its scope stoichiometric hydrates or solvates as well as compounds containing variable amounts of water and/or solvent.

Certain compounds of formula (I) are capable of existing in stereoisomeric forms (e.g. geometric or ("cis-trans") isomers, diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof. For compounds of formula (I) where $R^1$ is a $C_{3-6}$alkenyl group, the compounds may also exist as geometric isomers around the double bond. The present invention includes within its scope all such isomers, including mixtures.

In a further aspect, this invention provides a process for the preparation of a compound of formula (I) or a pharmaceutically acceptable salt thereof, which process comprises:

(a) the coupling of a compound of formula (II):

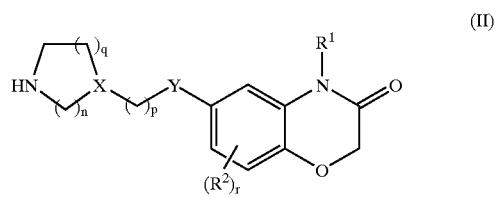

in which $R^1$, $R^2$, Y, n, p, q and r are defined in formula (I), with a compound of formula (III):

in which Ar and m are as defined for formula (I) and L is a leaving group; or (b) reacting a compound of formula (II) as defined above with a compound of formula (IV)

in which Ar and m are defined in formula (I), in the presence of a reducing agent; or (c) for a compound of formula (I) wherein X is N, reacting a compound of formula (V):

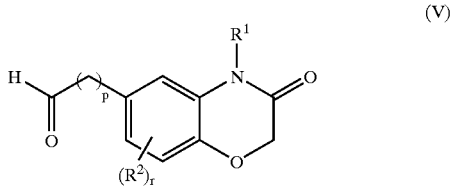

in which p, R², r and R¹ are as defined in formula (I), with a compound of formula (VI):

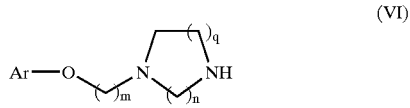

in which Ar, m, q and n are as defined in formula (I), in the presence of a reducing agent;
and optionally thereafter for each of process (a), (b) or (c):
  removing any protecting groups, and/or
  converting a compound of formula (I) into another compound of formula (I), and/or
  forming a pharmaceutically acceptable salt.

For process (a), suitable leaving groups include halogen particularly chloro or bromo), methylsulfonyloxy and 4-toluenesulfonyloxy (tosylate). The reactions of compounds of formula (II) and (III) are typically carried out in the presence of a base, such as diisopropylethylamine or sodium bicarbonate, in a suitable solvent such as isopropanol or dimethylformamide.

For processes (b) and (c), the reactions of a compounds of formula (II) and (IV) and of formula (V) and (VI) are carried out in the presence of a reducing agent, such as sodium triacetoxyborohydride, in a suitable solvent, such as dichloroethane or dichloromethane.

Compounds of formula (I) can be converted into further compounds of formula (1) using standard techniques. For example, and by way of illustration rather than limitation, for compounds of formula (I) wherein R¹ is hydrogen it may be possible to introduce a $C_{1-6}$alkyl group by conventional alkylation using 1 molar equivalent of a $C_{1-6}$alkylhalide and 1 molar equivalent of a suitable base in an inert solvent. Further, compounds of formula (I) may be converted to farther compounds of formula (I) by interconversion of either of substituents R² or those on group Ar.

Compounds of formulae (II), (III) and (IV) are commercially available, may be prepared according to procedures described herein, by known literature methods, or by analogous procedures thereto.

It will be appreciated by those skilled in the art that it may be necessary to protect certain reactive substituents during some of the above procedures. Standard protection and deprotection techniques, such as those described in Greene T. W. *Protective groups in organic synthesis*, New York, Wiley (1981), can be used. For example, primary amines can be protected as phthalimide, benzyl, t-butyloxycarbonyl, benzyloxycarbonyl or trityl derivatives. Carboxylic acid groups can be protected as esters. Aldehyde or ketone groups can be protected as acetals, ketals, thioacetals or thioketals. Deprotection of such groups is achieved using conventional procedures well known in the art. For example, protecting groups such as t-butyloxycarbonyl may be removed using an acid such as hydrochloric or trifluroroacetic acid in a suitable solvent such as dichloromethane, diethylether, isopropanol or mixtures thereof.

It will be further appreciated that compounds of formula (II), (III) and (IV) and any precursors thereto may have one or more chiral centres. Enantiomeric or diastereomeric mixtures of such compounds may be separated using conventional methods, for example by chromatography or by resolution by means of diastereomeric salt formation.

Pharmaceutically acceptable salts may be prepared conventionally by reaction with the appropriate acid or acid derivative.

The affinities of the compounds of this invention for $5\text{-HT}_{1A}$, $5\text{-HT}_{1B}$ and $5\text{-HT}_{1D}$ receptors can be determined by the radioligand binding assay as described in WO 99/07700. The intrinsic activity of the compounds of this invention can be determined according to the [$^{35}$S]GTPγS functional assay which is also described in WO 99/07700.

All compounds tested according to the radioligand binding assay described above were found to have pKi values >6.0 at $5\text{-HT}_{1A}$ receptors, with many showing a considerably higher affinity (having pKi values in the range 8.0–9.5). Certain compounds of this invention also demonstrate comparable affinity for $5\text{-HT}_{1B}$ and $5\text{-HT}_{1D}$ receptors.

It has been found, using the [$^{35}$S]GTPγS functional assay, that certain compounds of formula (I) appear to be antagonists at $5\text{-HT}_1$ type receptors whilst others appear to be inverse agonists, agonists or partial agonists.

The efficacy of the compounds of this invention to inhibit the re-uptake of serotonin can be measured in a 5-HT uptake assay by measurement of uptake of [$^3$H]-5-HT into rat cortical synaptosomes as described in Thomas, D. R.; Nelson, D. R.; and Johnson, A. M. *Psychopharmacology* 93:193–200 (1987). All compounds tested according to this uptake assay were found to have potency at the uptake site of pKi >6.0, with many showing a considerably higher potency (having pKi values >8.0).

Certain compounds of formula (I) demonstrate both affinity for the $5\text{-HT}_{1A}$ receptor (or affinity for $5\text{-HT}_{1A}$, $5\text{-HT}_{1B}$ and $5\text{-HT}_{1D}$ receptors) and potency at the uptake site in the higher ranges indicated above.

Compounds of formula (I) and their pharmaceutically acceptable salts are of use in the treatment or prophylaxis of certain CNS disorders such as depression, which term is used herein to include bipolar depression, unipolar depression, single or recurrent major depressive episodes with or without psychotic features, catatonic features, melancholic features, a typical features or postpartum onset, seasonal affective disorder, dysthymic disorders with early or late onset and with or without a typical features, neurotic depression and social phobia, depression accompanying dementia for example of the Alzheimer's type, vascular dementia with depressed mood, schizoaffective disorder or the depressed type, and depressive disorders resulting from general medical conditions including, but not limited to, myocardial infarction, diabetes, miscarriage or abortion, etc. Other CNS disorders which may be treated or prevented include anxiety disorders, including generalised anxiety, schizophrenia, panic disorder, agoraphobia, social phobia, obsessive compulsive disorder and post-traumatic stress disorder, pain (particularly neuropathic pain), memory disorders, including dementia, amnesic disorders and age-associated memory impairment, disorders of eating behaviours, including anorexia nervosa and bulimia nervosa, sexual dysfunction, sleep disorders (including disturbances of circadian rhythm, dyssomnia, insomnia, sleep apnea and narcolepsy), withdrawal from abuse of drugs such as of cocaine, ethanol, nicotine, benzodiazepines, alcohol, caffeine, phencyclidine (phencyclidine-like compounds), opiates (e.g. cannabis, heroin, morphine), sedative ipnotic, amphetamine or amphetamine-related drugs (e.g. dextroamphetamine, methylamphetamine) or a combination thereof, motor disorders such as Parkinson's disease, dementia in Parkinson's disease, neuroleptic-induced Parkinsonism and tardive dyskinesias, as well as other psychiatric disorders.

Compounds of formula (I) may also have utility in the treatment of certain gastrointestinal disorders such as irritable bowel syndrome, Crohn's disease, ulcerative colitis, non-steroidal anti-inflammatory drug induced damage.

Thus the invention also provides a compound of formula (I) or a pharmaceutically acceptable salt thereof, for use as a therapeutic substance, in particular in the treatment or prophylaxis of the above disorders. In particular the invention provides a compound of formula (I) or a pharmaceutically acceptable salt thereof for use as a therapeutic substance in the treatment or prophylaxis of depression.

Compounds of the invention may be administered in combination with other active substances such as 5HTT3 antagonists, NK-1 antagonists, serotonin agonists, selective serotonin reuptake inhibitors (SSRI), noradrenaline re-uptake inhibitors (SNRI), tricyclic antidepressants and/or dopaminergic antidepressants.

Suitable 5HT3 antagonists which may be used in combination of the compounds of the inventions include for example ondansetron, granisetron, metoclopramide.

Suitable serotonin agonists which may be used in combination with the compounds of the invention include sumatriptan, rauwolscine, yohimbine, metoclopramide.

Suitable SSRIs which may be used in combination with the compounds of the invention include fluoxetine, citalopram, femoxetine, fluvoxamine, paroxetine, indalpine, sertraline, zimeldine.

Suitable SNRIs which may be used in combination with the compounds of the invention include venlafaxine and reboxetine.

Suitable tricyclic antidepressants which may be used in combination with a compound of the invention include imipramine, amitriptiline, chlomipramine and nortriptiline.

Suitable dopaminergic antidepressants which may be used in combination with a compound of the invention include bupropion and amineptine.

It will be appreciated that the compounds of the combination or composition may be administered simultaneously (either in the same or different pharmaceutical formulations), separately or sequentially.

The invention further provides a method of treatment or prophylaxis of the above disorders in mammals including humans, which comprises administering to the sufferer a therapeutically safe and effective amount of a compound of formula (I) or a pharmaceutically acceptable salt thereof.

In another aspect, the invention provides for the use of a compound of formula (I) or a pharmaceutically acceptable salt thereof in the manufacture of a medicament for use in the treatment or prophylaxis of the above disorders.

In order to use the compounds of formula (I) in therapy, they will normally be formulated into a pharmaceutical composition in accordance with standard pharmaceutical practice. The present invention also provides a pharmaceutical composition, which comprises a compound of formula (I) or a pharmaceutically acceptable salt thereof, and a pharmaceutically acceptable carrier or excipient. In a further aspect, the present invention provides a process for preparing a pharmaceutical composition, the process comprising mixing a compound of formula (I) or a pharmaceutically acceptable salt thereof and a pharmaceutically acceptable carrier or excipient.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents (e.g. pregelatinised maize starch, polyvinylpyrrolidone or hydroxypropyl methylcellulose);, fillers (e.g. lactose, microcrystalline cellulose or calcium hydrogen phosphate);, tabletting lubricants lubricants (e.g. magnesium stearate, talc or silica);, disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound.

For parenteral administration, fluid unit dosage forms are prepared utilising a compound of the invention or pharmaceutically acceptable salt thereof and a sterile vehicle. Formulations for injection may be presented in unit dosage form e.g. in ampoules or in multi-dose, utilising a compound of the invention or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device. Thus compounds of formula (I) may be formulated for oral, buccal, parenteral, topical (including ophthalmic and nasal), depot or rectal administration or in a form suitable for administration by inhalation or insufflation (either through the mouth or nose).

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three times a day. Such therapy may extend for a number of weeks or months.

All publications, including but not limited to patents and patent applications, cited in this specification are herein incorporated by reference as if each individual publication were specifically and individually indicated to be incorporated by reference herein as though fully set forth.

The following Descriptions and Examples illustrate the preparation of the compounds of the invention.

Description 1

4-Hydroxy-3-nitrophenyl benzoate (D1)

To a stirred solution of 4-hydroxyphenyl benzoate (10 g, 47 mmol) in acetic acid (250 mL) was added, dropwise with external ice-bath cooling, nitric acid (d=1.42, 2.9 mL) (T=10° C.). The mixture was warmed to 20° C. and stirred for a further 56 h. The solution was evaporated in vacuo and water added to the residue. The resulting yellow solid was collected by filtration, washed with water and dried in vacuo to give the title compound (11.8 g, 97%).

$^1$H NMR (CDCl$_3$) δ: 7.23 (1H, d), 7.53 (3H, m), 7.67 (1H, m), 8.00 (1H, d), 8.17 (2H, m), 10.52 (1H, s).

Description 2

4-Methoxycarbonylmethyl-3-nitrophenyl benzoate (D2)

A mixture of 4-hydroxy-3-nitrophenyl benzoate (48.8 g, 0.19 mol), methyl bromoacetate (28.8 g, 0.19 mmol), anhydrous potassium carbonate (33.8 g, 0.24 mol) and acetone (700 mL) was heated at reflux for 24 h. The mixture was evaporated in vacuo and the residue partitioned between aqueous NaOH (1 M, 1 L) and dichloromethane (3×200 mL). The combined organic extracts were washed with aqueous NaOH (1 M, 500 mL), water (500 mL) and brine (250 mL), then dried (Na$_2$SO$_4$) and evaporated in vacuo to give a solid. Crystallisation from methanol with charcoal treatment gave the title compound (38 g, 61%) as pale yellow needles.

$^1$H NMR (CDCl$_3$) δ: 3.83 (3H, s), 4.82 (2H, s), 7.08 (1H, d, J=9 Hz), 7.45 (1H, dd, J=9, 2 Hz), 7.56 (2H, m), 7.67 (1H, m), 7.83 (1H, d, J=2 Hz), 8.19 (2H, m).

Description 3

4-Methoxycarbonylmethyl-3-nitrophenol (D3)

To a stirred suspension of 4-methoxycarbonylmethyl-3-nitrophenyl benzoate (26.2 g, 79 mmol) in methanol (600 mL) at 20° C. was added, dropwise over 0.3 h, a solution of sodium methoxide (4.7 g, 87 mmol) in methanol (300 mL). The resulting mixture was stirred at 20° C. for 2 h then at 50° C. for 1 h. The solution was concentrated to 200 mL in vacuo, then poured into water (1 L) and extracted with ether-hexane (1:5, 500 mL). The aqueous phase was neutralised with 2 M hydrochloric acid, then extracted with dichloromethane (6×300 mL). The combined dichloromethane extracts were dried (Na$_2$SO$_4$) and evaporated in vacuo to give a semi-solid, which was triturated with ether-hexane (1:3, 2×100 mL) to give the title compound (15.3 g, 85%) as a yellow solid.

$^1$H NMR (CDCl$_3$) δ: 2.00 (1H, br s), 3.80 (3H, s), 4.70 (2H, s), 6.95 (1H, d, J=9 Hz), 7.01 (1H, dd, J=9, 2 Hz), 7.33 (1H, d, J=2 Hz).

Description 4

4-(4-(N-(t-Butyloxycarbonyl)piperidinyl)oxy)-2-nitrophenoxyacetic acid, methyl ester (D4)

To a stirred solution of 4-methoxycarbonylmethyl-3-nitrophenol (6.0 g, 26.8 mmol), 1-(t-butyloxycarbonyl)-4-hydroxypiperidine (13.8 g, 68.9 mmol) and triphenylphosphine (18.0 g, 68.9 mmol) in tetrahydrofuran (80 mL) at 20° C. under argon was added diisopropyl azodicarboxylate (13.9 g, 68.9 mmol), dropwise over 0.75 h. The resulting solution was stirred at 20° C. for 4 h, then evaporated in vacuo. Chromatography of the residue on silica (400 g) eluting with 5–50% ether in hexane gave the title compound (10.1 g, 93%) as a yellow oil.

$^1$H NMR (CDCl$_3$) δ: 1.48 (9H, s), 1.65–2.00 (4H, m), 3.34 (2H, m), 3.69 (2H, m), 3.81 (3H, s), 4.44 (1H, m), 4.72 (2H, s), 7.02 (1H, d, J=9 Hz), 7.10 (1H, d, J=9, 2 Hz), 7.43 (1H, d, J=2 Hz).

The following, compounds were prepared in a similar manner to Description 4

(a) (±)-4-(3-(N-(t-Butyloxycarbonyl)pyrrolidinyl)methoxy)-2-nitrophenoxyacetic acid, methyl ester $^1$ H NMR (CDCl$_3$): δ 1.47 (9H, s), 1.78 (1H, m), 2.07 (1H, m), 2.66 (1H, m), 3.20 (1H, m), 3.70–3.65 (3H, m), 3.80

(3H, s), 3.91 (2H, m), 4.72 (2H, s), 7.03 (1H, d, J=9 Hz), 7.08 (1H, dd, J=9, 2 Hz), 7.39 (1H, d, J=2 Hz).

(b) (±)-4-(3-(N-(t-Butyloxycarbonyl)piperidinyl)methoxy)-2-nitrophenoxyacetic acid, methyl ester $^1$H NMR (CDCl$_3$) δ: 1.35 (1H, m), 1.45 (9H, s), 1.70 (1H, m), 1.89 (1H, m), 2.04 (1H, m), 1.60–3.00 (2H, m), 3.75–3.95 (4H, m), 3.80 (3H, s), 4.07 (1H, m), 4.72 (2H, s), 7.02 (1H, d, J=9 Hz), 7.09 (1H, dd, J=9.2 Hz), 7.38 (1H, d, J=2 Hz).

(c) (±)-4-(3-(N-(t-Butyloxycarbonyl)pyrrolidinyl)oxy)-2-nitrophenoxyacetic acid, methyl ester $^1$H NMR (CDCl$_3$) δ: 1.47 (9H, s), 2.15 (2H, m), 3.53 (4H, m), 3.80 (3H, s), 4.73 (2H, s), 4.85 (1H, m), 7.03 (2H, m), 7.37 (1H, d, J=2 Hz).

(d) (±)-4-(3-(N-(t-Butyloxycarbonyl)piperidinyl)oxy)-2-nitrophenoxyacetic acid, methyl ester $^1$H NMR (CDCl$_3$) δ: 1.41 (9H, s), 1.54 (1H, m), 1.68–1.92 (3H, m), 3.20–3.59 (4H, m) 3.80 (3H, s), 4.22 (1H, m), 4.72 (2H, s), 7.01 (1H, d, J=9 Hz), 7.10 (1H, dd, J=9, 2 Hz), 7.41 (1H, d, J=2 Hz).

Description 5

6-(4-(N-(t-Butyloxycarbonyl)piperidinyl)oxy)-4H-benzo[1,4]oxazin-3-one (D5)

A mixture of 4-(4-(N-(t-butyloxycarbonyl)piperidinyl)oxy)-2-nitrophenoxyacetic acid, methyl ester (10.1 g, 24.6 mmol), 10% palladium on carbon (1.0 g) and methanol (300 mL) was hydrogenated at 20° C. and 1 bar for 4 h. Catalyst was removed by filtration and the filtrate was evaporated in vacuo to give an oily residue, which was dissolved in toluene. The resulting solution was heated at reflux for 2 h then evaporated in vacuo. Chromatography of the residue on silica with 25–100% ethyl acetate-hexane gradient elution gave the title compound (7.2 g, 84%) as a colourless solid.

$^1$H NMR (CDCl$_3$) δ: 1.49 (9H, s), 1.74 (2H, m), 1.89 (2H, m), 3.02 (2H, m), 3.68 (2H, m), 4.34 (1H, m), 4.55 (2H, s), 6.44 (1H, d, J=2 Hz), 6.53 (1H, dd, J=9, 2 Hz), 6.89 (1H, d, J=9 Hz), 8.82 (1H, br s).

The following compounds were prepared in a similar manner to Description 5.

(a) 6-(4-(N-(t-Butyloxycarbonyl)piperidinyl)methyl)-4H-benzo[1,4]oxazin-3-one $^1$H NMR (CDCl$_3$) δ: 1.45 (9H, s), 1.60 (5H, m), 2.46 (2H, m), 2.63 (2H, m), 4.07 (2H, m), 4.60 (2H, s), 6.57 (1H, d, J=2 Hz), 6.74 (1H, dd, J=9, 2 Hz), 6.89 (1H, d, J=9 Hz), 8.29 (1H, br s).

(b) 6-(4-(N-(t-Butyloxycarbonyl)piperidinyl)carbonyl)-4H-benzo[1,4]oxazin-3-one

Mass spectrum (API$^-$): Found 359 ([M−H]$^-$). C$_{19}$H$_{24}$N$_2$O$_5$ requires 360.

(c) (±)-6-(3-(N-(t-Butyloxycarbonyl)pyrrolidinyl)methoxy)-4H-benzo[1,4]oxazin-3-one $^1$H NMR (CDCl$_3$) δ: 1.47 (9H, s), 1.79 (1H, m), 2.05 (1H, m), 2.65 (1H, m), 3.19 (1H, m), 3.25–3.66 (3H, m), 3.85 (2H, m), 4.55 (2H, s), 6.44 (1H, d, J=2 Hz), 6.50 (1H, dd, J=9, 2 Hz), 6.87 (1H, d, J=9 Hz), 9.02 (1H, br s).

(d) (±)-6-(3-(N-(t-Butyloxycarbonyl)piperidinyl)methoxy)-4H-benzo[1,4]oxazin-3-one Mass spectrum (API$^-$): Found 361 ([M−H]$^-$). C$_{19}$H$_{26}$N$_2$O$_5$ requires 362.

(e) (±)-6-(3-(N-(t-Butyloxycarbonyl)pyrrolidinyl)oxy)-4H-benzo[1,4]oxazin-3-one

Mass spectrum (API$^-$): Found 333 ([M−H]$^-$). C$_{17}$H$_{22}$N$_2$O$_5$ requires 334.

(f) (±)-6-(3-(N-(t-Butyloxycarbonyl)piperidinyl)oxy)-4H-benzo[1,4]oxazin-3-one

Mass spectrum (API$^-$): Found 347 ([M−H]$^-$). C$_{18}$H$_{24}$N$_2$O$_5$ requires 348.

(g) (±)-6-(3-(N-(t-Butyloxycarbonyl)piperidinyl))-4H-benzo[1,4]oxazin-3-one

Mass spectrum (API$^-$): Found 331 ([M−H]$^-$). C$_{18}$H$_{24}$N$_2$O$_4$ requires 332.

Description 6

6-(4-Piperidinyloxy)-4H-benzo[1,4]oxazin-3-one, hydrochloride (D6)

A mixture of 6-(4-(N-(t-butyloxycarbonyl)piperidinyl)oxy)-4H-benzo[1,4]oxazin-3-one (3.78 g, 10.9 mmol), ethereal hydrogen chloride (50 mL) and dichloromethane (20 mL) was heated at 40° C. for 2 h, then allowed to stir at 20° C. for 18 h. The resulting colourless solid was collected by filtration to give the title compound (2.72 g, 88%).

$^1$H NMR (CD$_3$OD) δ: 1.95–2.25 (4H, m), 3.24 (2H, m), 3.40 (2H, m), 4.53 (2H, s), 4.60 (1H, m), 6.60 (1H, d, J=2 Hz), 6.65 (1H, dd, J=9, 2 Hz), 6.92 (1H, d, J=9 Hz).

The following compounds were prepared in a similar manner to Description 6

(a) 4-Methyl-6-(4-piperidinyloxy)-4H-benzo[1,4]oxazin-3-one, hydrochloride

Mass spectrum (API$^+$): Found 263 (MH$^+$). C$_{14}$H$_{18}$N$_2$O$_3$ requires 262.

(b) 6-(4-Piperidinylmethyl)-4H-benzo[1,4]oxazin-3-one, hydrochloride

Mass spectrum (API$^+$): Found 247 (MH$^+$). C$_{14}$H$_{18}$N$_2$O$_2$ requires 246.

(c) 4-Methyl-6-(4-piperidinylmethyl)-4H-benzo[1,4]oxazin-3-one, hydrochloride

Mass spectrum (API$^+$): Found 261 (MH$^+$). C$_{15}$H$_{20}$N$_2$O$_2$ requires 260.

(d) 6-(4-(Piperidinylcarbonyl)-4H-benzo[1,4]oxazin-3-one, hydrochloride

Mass spectrum (API$^+$): Found 261 (MH$^+$). C$_{14}$H$_{16}$N$_2$O$_3$ requires 260.

(e) (±)-6-(3-Pyrrolidinylmethoxy)-4H-benzo[1,4]oxazin-3-one, hydrochloride

Mass spectrum (API$^+$): Found 249 (MH$^+$). C$_{13}$H$_{16}$N$_2$O$_3$ requires 248.

(f) (±)-6-(3-Piperidinylmethoxy)-4H-benzo[1,4]oxazin-3-one, hydrochloride

Mass spectrum (API$^+$): Found 263 (MH$^+$). C$_{14}$H$_{18}$N$_2$O$_3$ requires 262.

(g) (±)-6-(3-Pyrrolidinyloxy)-4H-benzo[1,4]oxazin-3-one, hydrochloride

Mass spectrum (API$^+$): Found 235 (MH$^+$). C$_{12}$H$_{14}$N$_2$O$_3$ requires 234.

(h) (±)-6-(3-Piperidinyloxy)-4H-benzo[1,4]oxazin-3-one, hydrochloride

Mass spectrum (API$^-$): Found 247 ([M−H]$^-$). C$_{13}$H$_{16}$N$_2$O$_3$ requires 248.

(i) (±)-6-(3-Piperidinyl)-4H-benzo[1,4]oxazin-3-one, hydrochloride

Mass spectrum (API$^+$): Found 233 (MH$^+$). C$_{13}$H$_{16}$N$_2$O$_2$ requires 232.

(j) 6-(1-Piperazinylmethyl)-4H-benzo[1,4]oxazin-3-one, dihydrochloride

Mass spectrum (API$^+$): Found 248 (MH$^+$). C$_{13}$H$_{17}$N$_3$O$_2$ requires 247.

(k) 6-(1-Piperazinyl)-4H-benzo[1,4]oxazin-3-one, dihydrochloride

Mass spectrum (API$^+$): Found 234 (MH$^+$). C$_{12}$H$_{15}$N$_3$O$_2$ requires 233.

Description 7

6-(4-(N-(t-Butyloxycarbonyl)piperidinyl)oxy)-4-methyl-4H-benzo[1,4]oxazin-3-one (D7)

6-(4-(N-(t-Butyloxycarbonyl)piperidinyl)oxy)-4H-benzo[1,4]oxazin-3-one (2.50 g, 7.18 mmol) in dimethylformamide (30 mL) was added to a suspension of sodium hydride (60% dispersion in oil, 346 mg, 8.64 mmol) in DMF (10 mL) cooled in an ice-bath to 5° C. The resulting mixture was stirred at 20° C. under argon for 1 h, then a solution of methyl iodide (2 g, 14.1 mmol) in DMF (5 mL) was added dropwise, with ice-bath cooling over 0.2 h. The resulting mixture was stirred at 20° C. for 18 h. The reaction mixture was poured into water (100 mL) and extracted with ether (3×75 mL). The combined organic extracts were washed with water (100 mL), dried ($Na_2SO_4$) and evaporated in vacuo to give the title compound (2.60 g, 100%) as a pale brown oil.

$^1$H NMR ($CDCl_3$) δ: 1.47 (9H, s), 1.75 (2H, m), 1.92 (2H, m), 3.32 (5H, m), 3.72 (2H, m), 4.38 (1H, m), 4.56 (2H, s), 6.64 (2H, m), 6.88 (1H, d, J=9 Hz).

The following compound was prepared in a similar manner to Description 7.

(a) 6-(4-(N-(t-Butyloxycarbonyl)piperidinyl)methyl)-4-methyl-4H-benzo[1,4]oxazin-3-one $^1$H NMR ($CDCl_3$) δ: 1.45 (9H, s), 1.61 (5H, m), 2.51 (2H, m), 2.64 (2H, m), 3.36 (3H, s), 4.07 (2H, m), 4.59 (2H, s), 6.75 (2H, m), 6.89 (1H, d, J=9 Hz).

Description 8

4-(4-Hydroxy)benzoylpiperidine (D8)

A solution of 4-(4-methoxy)benzoylpiperidine hydrochloride (3.0 g, 11.7 mmol), in 48% HBr (aq) (16 mL), and acetic acid (16 mL) was heated at reflux for 48 h. The reaction mixture was evaporated to dryness in vacuo to give an off-white solid which was suspended in saturated $NaHCO_3$ (aq). The resulting precipitate was collected by filtration, washed with water, and dried to give the title compound (1.76 g, 73%) as an off-white solid.

Mass spectrum (API$^+$): Found 206 (MH$^+$). $C_{12}H_{15}NO_2$ requires 205.

Description 9

1-(t-Butyloxycarbonyl)-4-(4-hydroxy-3-nitro)benzoylpiperidine (D9)

A solution of 4-(4-hydroxy)benzoylpiperidine (1.52 g, 7.4 mmol) in acetic acid (20 mL) was treated with conc. $HNO_3$ (0.54 mL) in acetic acid (2 mL), and the resulting mixture was stirred at 100° C. for 2 h. Reaction mixture was cooled and evaporated in vacuo to give an orange/brown solid (2.0 g), which was dissolved in a mixture of THF (15 mL), water (4 mL), and triethylamine (1.2 mL), and treated with di-tert-butyldicarbonate (1.62 g, 7.4 mmol). The mixture was stirred at room temperature for 2 h, then evaporated in vacuo, and the residue partitioned between ethyl acetate (100 mL) and water (100 mL). The organic layer was separated and washed twice more with water (2×50 mL), then dried ($Na_2SO_4$) and evaporated in vacuo to give a brown oil (2.4 g) which was purified by chromatography on silica gel (20 g) eluting with 50–100% EtOAc in hexane to give the title compound (1.86 g, 72%) as a yellow oil.

$^1$H NMR ($CDCl_3$) δ: 1.47 (9H, s), 1.66–1.89 (4H, m), 2.95 (2H, m), 3.37 (1H, m), 4.18 (2H, m), 7.27 (1H, d, J=9 Hz), 8.20 (1H, dd, J=9, 2 Hz), 8.71 (1H, d, J=2 Hz), 10.92 (1H, br, s).

Description 10

4-(4-(1-(t-Butyloxycarbonyl)piperidinyl)carbonyl)-2-nitrophenoxyacetic acid, methyl ester (D10)

A mixture of 1-(t-butoxycarbonyl)-4-(4-hydroxy-3-nitro) benzoylpiperidine (1.50 g, 4.3 mmol), potassium carbonate (0.77 g, 5.6 mmol), and methyl bromoacetate (0.66 g, 4.3 mmol) in acetone (20 mL) was stirred at reflux for 18 h. The reaction mixture was cooled and evaporated in vacuo and the residue partitioned between water (20 mL) and dichloromethane (20 mL). The organic layer was separated and washed with 1N NaOH (aq) (20 mL), water (20 mL), and brine (10 mL), dried ($Na_2SO_4$) and evaporated in vacuo to give crude product which was purified by chromatography on silica gel (~20 g) eluting with 10–100% EtOAc in hexane to give the title compound (0.85 g, 47%) as a yellow oil.

$^1$H NMR ($CDCl_3$) δ: 1.47 (9H, s), 1.62–1.89 (4H, m), 2.91 (2H, m), 3.35 (1H, m), 3.82 (3H, s), 4.17 (2H, m), 4.88 (2H, s), 7.04 (1H, d, J=9 Hz), 8.13 (1H, dd, J=9, 2 Hz), 8.44 (1H, d, J=2 Hz).

The following compound was prepared in a similar manner to Description 10

(a) 4-(4-(1-(t-Butyloxycarbonyl)piperidinyl)methyl)-2-nitrophenoxyacetic acid, methyl ester $^1$H NMR ($CDCl_3$) δ: 1.45 (9H, s), 1.59 (5H, m), 2.54 (2H, m), 2.64 (2H, m), 3.80 (3H, s), 4.08 (2H, m), 4.76 (2H, s), 6.92 (1H, d, J=9 Hz), 7.28 (1H, dd, J=9, 2 Hz), 7.65 (1H, d, J=2 Hz).

Description 11

(±)-4-(3-(1-(t-Butyloxycarbonyl)piperidinyl))-2-nitrophenol (D11)

A solution of 3-(4-hydroxyphenyl)piperidine [B. Macchia et al., *Eur. J. Med. Chem. Chim. Ther.* 1995, 30, 869] (3.8 g, 21.6 mmol) in acetic acid (50 mL) was treated with conc. nitric acid (2 mL), and the resulting mixture stirred at room temperature for 16 h. Reaction mixture was evaporated in vacuo to give an orange oil which was dissolved in a mixture of THF (50 mL), water (13 mL), and triethylamine (3.6 mL) and treated with di-tert-butyl dicarbonate (4.7 g, 21.6 mmol). The resulting mixture was stirred at room temperature for 18 h, then partitioned between ethyl acetate (100 mL) and water (100 mL). The organic layer was separated, dried ($Na_2SO_4$) and evaporated in vacuo to give the crude product, which was purified by chromatography on silica gel (200 g) eluting with 50–100% EtOAc in hexane to give the title compound (1.97 g, 28%) as a brown oil.

$^1$H NMR ($CDCl_3$) δ: 1.48 (9H, s), 1.58 (2H, m), 2.01 (1H, m), 2.61–2.87 (4H, m), 4.11 (2H, m), 7.12 (1H, d, J=9 Hz), 7.47 (1H, dd, J=9, 2 Hz), 7.78 (1H, d, J=2 Hz), 11.02 (1H, br s).

Description 12

(±)-4-(3-(1-(t-Butyloxycarbonyl)piperidinyl))-2-nitrophenoxyacetic acid, methyl ester (D12)

The title compound was prepared in a similar manner to Description 10, in 80% yield.

$^1$H NMR ($CDCl_3$) δ: 1.47 (9H, s), 1.51–1.79 (3H, m), 2.65–2.87 (4H, m), 3.81 (3H, s), 4.08 (2H, m), 4.78 (2H, s), 6.94 (1H, d, J=9 Hz), 7.39 (1H, dd, J=9, 2 Hz), 7.73 (1H, d, J=2 Hz).

Description 13

6-(4-Pyridyl)-4H-benzo[1,4]oxazin-3-one (D13)

A mixture of 6-bromo-4H-benzo[1,4]oxazin-3-one [N. Mazharuddin et al., *Indian J. Chem.* 1969, 7, 658] (1.37 g, 6 mmol), pyridine-4-boronic acid (0.72 g, 6 mmol), sodium bicarbonate (1.51 g, 18 mmol), (tetrakistriphenylphosphine)palladium (0) (348 mg, 0.3 mmol) in water (18 mL), and 1,2-dimethoxyethane (30 mL), was stirred at reflux under an argon atmosphere for 72 h. Reaction mixture was cooled and partitioned between ethyl acetate (100 mL) and water (100 mL). The organic layer was separated and dried ($Na_2SO_4$) and evaporated in vacuo to give a brown solid which was purified by chromatography on silica gel (30 g) eluting with 0–5% MeOH in EtOAc to give the title compound (0.58 g, 43%) as a yellow solid.

Mass spectrum ($API^+$): Found 227 ($MH^+$). $C_{13}H_{10}N_2O_2$ requires 226.

Description 14

6-(4-Piperidinyl)-4H-benzo[1,4]oxazin-3-one (D14)

A solution of 6-(4-pyridyl)-4H-benzo[1,4]oxazin-3-one (0.57 g, 2.52 mmol), in methanol (15 mL) was treated with platinum (IV) oxide (50 mg, 0.22 mmol) and 1M HCl in ether (2.7 mL) and stirred at room temperature under an atmosphere of hydrogen for 24 h. The reaction mixture was filtered through celite and the filtrate evaporated in vacuo to give the title compound (0.59 g, 87%) as a pale yellow solid.

Mass spectrum ($API^+$): Found 233 ($MH^+$). $C_{13}H_{16}N_2O_2$ requires 232.

Description 15

6-Formyl-4H-benzo[1,4]oxazin-3-one (D15)

A mixture of 4-hydroxy-3-nitrobenzaldehyde (3.05 g, 18.3 mmol), ethyl bromoacetate (3.20 g, 19.2 mmol), potassium carbonate (2.77 g, 20.1 mmol) and N,N-dimethylformamide (100 mL) was stirred at 20° C. for 40 h. The resulting solution was partitioned between water (300 mL) and ethyl acetate (300 mL), and the organic phase was washed with water (2×200 mL) and brine (100 mL), then dried ($MgSO_4$) and evaporated in vacuo to give a solid (3.85 g). An aliquot of this solid (0.65 g) was dissolved in acetic acid (16 mL) and iron powder (2.85 g, 50.9 mmol) was added. The mixture was heated to 60° C. for 20 h, then the mixture was cooled and filtered through celite. The filtrate was evaporated in vacuo and the residue was partitioned between ethyl acetate (100 mL) and saturated aqueous $NaHCO_3$. The organic phase was dried ($Na_2SO_4$) and evaporated in vacuo to give the title compound (0.31 g, 57%).

$^1$H NMR (DMSO-$d_6$) δ: 4.72 (2H, s), 7.14 (1H, d, J=8 Hz), 7.38 (1H, d, J=2 Hz), 7.54 (1H, dd, J=8, 2 Hz), 9.84 (1H, s), 10.98 (1H, br s).

Description 16

6-(4-(1-(t-Butyloxycarbonyl)piperazinyl)methyl)-4H-benzo[1,4]oxazin-3-one (D16)

A mixture of 6-formyl-4H-benzo[1,4]oxazin-3-one (1.91 g, 10.8 mmol) and N-(t-butoxycarbonyl)piperazine (2.0 g, 10.8 mmol) in 1,2-dichloroethane (120 mL), was cooled in an ice-bath, and treated portionwise with sodium triacetoxyborohydride (3.43 g, 16.2 mmol) over 0.3 h, with stirring under argon. The resulting mixture was stirred at room temperature for 4 h, then partitioned between dichloromethane (100 mL) and saturated aqueous sodium bicarbonate. The organic layer was separated, dried ($Na_2SO_4$) and evaporated in vacuo to give the title compound (3.52 g, 94%) as a yellow oil.

$^1$H NMR ($CDCl_3$) δ: 1.46 (9H, s), 2.36 (4H, m), 3.42 (6H, m), 4.61 (2H, s), 6.82 (1H, m), 6.90 (2H, m), 8.86 (1H, br s),

Description 17

1-(t-Butyloxycarbonyl)-4-(4-hydroxy-3-nitro)phenylpiperazine (D17)

To a solution of 1-(4-hydroxy)phenylpiperazine (10.0 g, 56.2 mmol) in conc. sulfuric acid (300 mL) was added potassium nitrate (6.8 g, 67.4 mmol) portionwise. The reaction mixture was stirred at 60° C. for 1.5 h and allowed to cool to room temperature, then was poured onto crushed ice (~1 L). The mixture was carefully neutralized to pH 7 using 0.880 ammonia solution and allowed to stand for 16 h. The black slurry was extracted with ethyl acetate. The aqueous phase was separated and evaporated in vacuo to give a brown slurry which was dissolved in tetrahydrofuran (700 mL) and triethylamine (8.6 mL). The solution was treated with di-tert-butyl dicarbonate (12.25 g. 56.2 mmol), and the reaction mixture was stirred at room temperature for 3 h, then evaporated in vacuo. The residue was partitioned between ethyl acetate (200 mL) and water (200 mL). The organic layer was dried ($Na_2SO_4$) and evaporated in vacuo to give the title compound (10.3 g, 57%) as a dark oil.

$^1$H NMR ($CDCl_3$) δ: 1.49 (9H, s), 3.06 (4H, m), 3.59 (4H, m), 7.09 (1H, d, J=9 Hz), 7.30 (1H, dd, J=9, 2 Hz), 7.50 (1H, d, J=2 Hz), 10.31 (1H, br s).

Description 18

4-(4-(1-(t-Butyloxycarbonyl)piperazinyl))-2-nitrophenoxyacetic acid, methyl ester (D18)

The title compound was prepared in a similar manner to Description 10, in 90% yield.

$^1$H NMR ($CDCl_3$) δ: 1.48 (9H, s), 3.10 (4H, m), 3.58 (4H, m), 3.80 (3H, s), 4.71 (2H, s), 6.99 (1H, d, J=9 Hz), 7.08 (1H, dd, J=9, 2 Hz), 7.38 (1H, d, J=2 Hz).

Description 19

4-(4-Hydroxybenzyl)piperidine hydrogen sulfate (D19)

A mixture of 4-(4-methoxyphenyl)pyridine (23.27 g, 0.117 mol), 48% HBr (150 mL) and acetic acid (150 mL) was stirred at reflux for 24 h. The reaction mixture was cooled and evaporated to dryness in vacuo to give a brown solid which was suspended in saturated aqueous $NaHCO_3$ (to pH 8). The resulting solid was collected by filtration, washed with water, and dried to give a yellow solid (20.7 g) which was dissolved in methanol (600 mL) and treated with conc. $H_2SO_4$ (10.9 g) and platinum (IV) oxide (600 mg). The reaction mixture was stirred under an atmosphere of hydrogen at 20° C. and 1 bar for 18 h, then filtered through celite. The filtrate was evaporated in vacuo to give the title compound (32.3 g, 100%) as a yellow oil.

Mass spectrum ($API^+$): Found 192 ($MH^+$). $C_{12}H_{17}NO$ requires 191.

Description 20

1-(t-Butyloxycarbonyl)-4-(4-hydroxy-3-nitro)benzylpiperidine (D20)

A mixture of 4-(4-hydroxybenzyl)piperidine hydrogen sulfate (32.2 g, 0.111 mol) in glacial acetic acid (330 mL), was treated dropwise with a solution of 70% nitric acid (20 mL) in glacial acetic acid (20 mL) with stirring. The resulting mixture was stirred at room temperature for 0.5 h then evaporated in vacuo to give a dark oil (49 g) which was dissolved in a mixture of water (170 mL), tetrahydrofuran (270 mL) and triethylamine (40 mL). A solution of di-tert-butyldicarbonate (26.3 g, 0.12 mol) in tetrahydrofuran (100 mL) was added slowly under argon with stirring. The reaction mixture was stirred at room temperature for 18 h and then partitioned between ethyl acetate (3×200 mL) and water (200 mL). The combined organic extracts were dried ($Na_2SO_4$) and evaporated in vacuo to give the title compound (37.30 g, 100%) as a dark oil.

Mass spectrum (API$^-$): Found 335 ([M−H]$^-$). $C_{17}H_{24}N_2O_5$ requires 336.

Description 21

8-Quinolinyloxyacetaldehyde (D21)

To a suspension of sodium hydride (60% oil dispersion, 3.0 g, 75 mmol) in DMF (100 mL) at 0° C. under argon, was added a solution of 8-hydroxyquinoline (9.2 g, 64 mmol) in DMF (20 mL) dropwise. The mixture was allowed to stir for 0.5 h, then allyl bromide (6.6 mL, 77 mmol) was added dropwise. The mixture was stirred at room temperature for 20 h, then was poured into ice/water (400 mL) and extracted with ether (3×300 mL). Combined organic extracts were washed with water (500 mL) and evaporated in vacuo. The crude residue was purified by silica gel chromatography (ethyl acetate in hexane 25%–75% gradient) to give 8-allyloxyquinoline (8.5 g, 72%) as an oil.

A solution of osmium tetroxide (2.1 mmol) in tert-butanol (26 mL) was added to a stirred mixture of 8-allyloxyquinoline (3.7 g, 20 mmol), sodium periodate (15 g, 70 mmol), THF (90 mL), methanol (4 mL) and water (2 mL). The mixture was stirred at room temperature for 20 h, then was extracted with dichloromethane (100 mL). The aqueous layer was basified with the addition of sodium hydrogen carbonate then was extracted with dichloromethane (2×200 mL). The combined organic extracts were washed with 20% w/w sodium sulfite solution (200 mL), then dried over sodium sulfate and evaporated in vacuo to give the title compound (1.1 g, 30%) as an amber oil.

Mass spectrum (API$^+$): Found 188 (MH$^+$). $C_{11}H_9NO_2$ requires 187.

Description 22

1-Isoquinolinyloxyacetaldehyde (D22)

To a stirred suspension of sodium hydride (60% oil dispersion, 1.2 g, 30 mmol) in DMF (6 mL) was added dropwise 2-hydroxyacetaldehyde dimethyl acetal (3.2 g, 30 mmol). The resulting mixture was left to stir for 0.5 h, then a solution of 1-chloroisoquinoline (1.6 g, 10 mmol) in DMF (2 mL) was added and the mixture was stirred at 80° C. for 24 h. The mixture was then poured into water (150 mL) and extracted with ether (2×150 mL). The combined organic extracts were dried over sodium sulfate and evaporated in vacuo. The residue was purified by silica gel chromatography (10% ethyl acetate in hexane) to give 1-isoquinolinyloxyacetaldehyde dimethyl acetal (1.5 g, 64%).

A mixture of 1-isoquinolinyloxyacetaldehyde dimethyl acetal (0.93 g, 4 mmol), dioxane (10 mL), water (15 mL) and conc. sulfuric acid (2 mmol) was heated at 85° C. for 2 h, then was quenched with saturated aqueous sodium hydrogen carbonate (100 mL). The resulting mixture was extracted with dichloromethane (2×100 mL) and the combined organic extracts were washed with saturated aqueous sodium hydrogen carbonate (50 mL), dried over sodium sulfate and evaporated in vacuo to give the title compound (0.43 g, 57%).

Mass spectrum (API$^+$): Found 188 (MH$^+$). $C_{11}H_9NO_2$ requires 187.

Description 23

4-(2-Cyano)indolyloxyacetaldehyde (D23)

The title compound was prepared from 2-cyano-4-hydroxyindole [K. G. Estep, Synth. Commun., 1995, 25, 507] using a procedure similar to that described in H. Sasai et al., Tetrahedron 1994, 43, 12313.

Other aryloxyacetaldehydes are known in the literature or were prepared by analogous methods Description 24

2-(5-Quinolinyloxy)ethyl bromide (D24)

A mixture of 5-hydroxyquinoline (0.3 g, 2.1 mmol), 1,2-dibromoethane (3.9 g, 21 mmol) and potassium carbonate (1.5 g, 11 mmol) in methyl ethyl ketone (15 mL) was allowed to stir at 85° C. for 24 h. The mixture was evaporated in vacuo and the residue was partitioned between ether (200 mL) and water (200 mL). The organic layer was dried over sodium sulfate and evaporated in vacuo to give the title compound (0.53 g).

$^1$H NMR (CDCl$_3$) δ: 3.80 (2H, m), 4.49 (2H, m), 6.86 (1H, d, J=8 Hz), 7.41 (1H, dd, J=8, 4 Hz), 7.61 (1H, t, J=8 Hz), 7.73 (1H, d, J=8 Hz), 8.64 (1H, d, J=8 Hz), 8.91 (1H, m).

Description 25

5-Hydroxy-2-methylquinoline (D25)

A mixture of 2-methyl-5,6,7,8-tetrahydroquinolin-5-one [E. Reimann, J. Freisinger, Arch. Pharm. (Weinheim), 318, 871 (1985)] (0.57 g, 3.5 mmol) and 48% aqueous HBr (3.5 mL) was warmed to 60° C. and treated dropwise with bromine (0.19 mL, 0.59 g, 3.6 mmol), with vigorous stirring. The resulting mixture was stirred at 60° C. for 1 h, then evaporated in vacuo. The residue was treated with isopropanol with stirring, then the mixture was evaporated in vacuo to give a waxy solid, which was triturated with 1:1 isopropanol—ether to give a beige powder (0.9 g). A mixture of this material, lithium carbonate (0.48 g, 6.7 mmol), lithium bromide (0.28 g, 3.2 mmol) and N,N-dimethylformamide (10 mL) was heated at 150° C. under argon with stirring for 2 h. The mixture was cooled then evaporated in vacuo. Chromatography of the residue on silica with 0–100% ethyl acetate-hexane gradient elution gave the title compound (0.28 g, 49%) as a solid.

Mass spectrum (API$^+$): Found 160 (MH$^+$). $C_{10}H_9NO$ requires 159.

Description 26

2-(5-(2-Methyl)quinolinyloxy)ethyl bromide (D26)

The title compound was prepared from 5-hydroxy-2-methylquinoline and 1,2-dibromoethane using a similar procedure to Description 24, in 91% yield.

Mass spectrum (API$^+$): Found 266 (MH$^+$). $C_{12}H_{12}{}^{79}BrNO$ requires 265.

The following aryloxyethyl bromides were prepared from the corresponding phenol and either 1,2-dibromoethane or 1,3-dibromopropane, using a procedure similar to that of Description 24.

a) 2-(7-(2,2-Dimethyl-2,3-dihydro)benzo[b]furanyl)oxyethyl bromide
b) 3-(7-(2,2-Dimethyl-2,3-dihydro)benzo[b]furanyl)oxypropyl bromide
c) 2-(5-Isoxazolyl)phenoxyethyl bromide
d) 3-(5-Isoxazolyl)phenoxypropyl bromide
e) 2-(8-(6-Fluoro-3,4-dihydro)-2H-benzo[b]pyranyl)oxyethyl bromide
f) 3-(1-(5-Oxo-5,6,7,8-tetrahydro)naphthyl)oxypropyl bromide
g) 2-(7-(2,3-Dihydro)benzo[b]furanyl)oxyethyl bromide
h) 2-(7-Benzo[b]furanyl)oxyethyl bromide
i) 2-(8-(2,2-Dimethyl-3,4-dihydro)-2H-benzo[b]pyranyl)oxyethyl bromide
j) 3-(8-(2,2-Dimethyl-3,4-dihydro)-2H-benzo[b]pyranyl)oxypropyl bromide
k) 2-(7-(2-Methyl)benzo[b]furanyl)oxyethyl bromide
l) 3-(7-(2-Methyl)benzo[b]furanyl)oxypropyl bromide
m) 2-(7-(2,2-Dimethyl-2,3-dihydro-3-fluoro)benzo[b]furanyl)oxyethyl bromide
n) 3-(7-(2,2-Dimethyl-2,3-dihydro-3-fluoro)benzo[b]furanyl)oxypropyl bromide
o) 3-(2-Cyano-4-fluoro)phenoxypropyl bromide
p) 2-(5-(3-Methyl)quinolinyl)oxyethyl bromide
q) 2-(5-Cinnolinyl)oxyethyl bromide
r) 2-(4-(2,3-Dihydro)benzo[b]furanyl)oxyethyl bromide
s) 2-(4-Benzo[b]furanyl)oxyethyl bromide
t) 3-(5-(2-Methyl)quinoxalinyl)oxypropyl bromide
u) 3-(2-(5-(3-Methyl)isoxazolyl)phenoxy)propyl bromide
v) 2-(5-(7-Fluoro-2-methyl)quinolinyl)oxyethyl bromide
w) 2-(5-(2-Methyl)quinazolinyl)oxyethyl bromide Other aryloxyalkyl bromides are known in the literature or were prepared by analogous methods.

Description 27

3-(5-(2-Methyl)quinolinyl)oxypropyl bromide (D27)

The title compound was prepared from 5-hydroxy-2-methylquinoline and 1,3-dibromopropane using a similar procedure to Description 24.

Mass spectrum (API$^+$): Found 280 (MH$^+$). $C_{13}H_{14}{}^{79}BrNO$ requires 279.

Description 28

2-(5-(8-Chloro-2-methyl)quinolinyl)oxyethyl bromide (D28)

The title compound was prepared from 8-chloro-5-hydroxy 2-methylquinoline and 1,2-dibromoethane using a similar procedure to Description 24.

Mass spectrum (API$^+$): Found 300 (MH$^+$). $C_{12}H_{11}{}^{79}Br^{35}ClNO$ requires 299.

Description 29

2-(5-(8-Fluoro-2-methyl)quinolinyl)oxyethyl bromide (D29)

The title compound was prepared from 8-fluoro-5-hydroxy-2-methylquinoline and 1,2-dibromoethane using a similar procedure to Description 24.

Mass spectrum (API$^+$): Found 284 (MH$^+$). $C_{12}H_{11}{}^{79}BrFNO$ requires 283.

Description 30

2-(5-(7-Chloro-2-methyl)quinolinyl)oxyethyl bromide (D30)

The title compound was prepared from 7-chloro-5-hydroxy-2-methylquinoline and 1,2-dibromoethane using a similar procedure to Description 24.

Mass spectrum (API$^+$): Found 300 (MH$^+$). $C_{12}H_{11}{}^{79}Br^{35}ClNO$ requires 299.

Description 31

3-(5-(7-Chloro-2-methyl)quinolinyl)oxypropyl bromide (D31)

The title compound was prepared from 7-chloro-5-hydroxy-2-methylquinoline and 1,3-dibromopropane using a similar procedure to Description 24.

Mass spectrum (API$^+$): Found 314 (MH$^+$). $C_{13}H_{13}{}^{79}Br^{35}ClNO$ requires 313.

Description 32

2-(4-(1-Acetyl)-indazolyl)oxyethyl iodide (D32)

A mixture of 2-(4-(1-acetyl)-1-H-indazolyl)oxyethyl chloride (1.1 g, 4.6 mmol), and sodium iodide (0.69 g, 4.6 mmol) in acetone (10 mL), was stirred at 45° C. for 16 h and then evaporated in vacuo. The residue was partitioned between dichloromethane (10 mL), and water (10 mL). The organic layer was dried ($Na_2SO_4$) and evaporated in vacuo to give a brown oil (0.91 g, 60%).

$^1$H NMR (CDCl$_3$) δ: 2.32 (3H, s), 3.82 (2H, m), 4.23 (2H, m), 6.69 (1H, m), 7.45 (1H, m), 8.03 (1H, m), 8.23 (1H, m).

Description 33

2-(4-(1H)-Indazolyl)oxyethyl chloride (D33)

Prepared in a similar manner to that described in R. E. Mewshaw et al, *Bioorg. Med. Chem. Lett.* (1999), 9 (17), 2593–2598.

Mass spectrum (API$^+$): Found 239 (MH$^+$). $C_{11}H_{11}{}^{35}ClN_2O_2$ requires 238.

Description 34

8-Chloro-5-hydroxy-2-methylquinoline (D34)

Crotonaldehyde (17.5 mL, 0.21 mol) was added dropwise to a refluxing solution of 2-chloro-5-methoxyaniline hydrochloride (10.36 g. 53.4 mmol) in 5 N hydrochloric acid (450 mL) and reflux continued for a further 0.5 h. The reaction mixture was cooled and diluted with water (500 mL), then extracted with ether (400 mL). The aqueous layer was separated and basified using 50% aqueous NaOH (pH 14), and then extracted into dichloromethane (3×300 mL). The combined organic phases were dried ($Na_2SO_4$) and evaporated in vacuo to give a dark oil which was purified by chromatography on silica gel (~200 g) eluting with 20% EtOAc in hexane to give a brown oil (5.17 g) which was heated at reflux in a mixture of acetic acid (30 mL) and 48% hydrobromic acid (30 mL) for 66 h. Reaction mixture was evaporated in vacuo and the residue suspended in sat. NaHCO$_3$ (aq), then extracted into dichloromethane (3×50 mL). The combined organic phases were dried ($Na_2SO_4$) and evaporated in vacuo to give a brown solid (2.90 g, 28%).

Mass spectrum (API$^+$): Found 194 (MH$^+$). $C_{10}H_8{}^{35}ClNO$ requires 193.

Description 35

8-Fluoro-5-hydroxy-2-methylquinoline (D35)

The title compound was prepared from 2-fluoro-5-methoxyaniline using a similar procedure to Description 34, in 43% yield.

Mass spectrum (API$^+$): Found 178 (MH$^+$). $C_{10}H_8FNO$ requires 177.

Description 36

2-Fluoro-5-methoxyaniline (D36)

To a stirred mixture of 2,6-dibromo-4-fluoroanisole (52.5 g, 0.185 mol) in 98% sulfuric acid (152 mL) at 15° C. was added, dropwise over 0.5 h, a solution of nitric acid (9.2 mL) and sulfuric acid (152 mL) with external ice-bath cooling. The mixture was stirred at 20° C. over 4 h, then was poured into ice water (1 kg) and extracted with dichloromethane (3×150 mL). The combined extracts were dried ($Na_2SO_4$) and evaporated in vacuo to give a brown oil. Chromatography on silica with 1–50% ether in hexane gradient elution gave an off-white solid, a solution of which in ethanol (250 mL) was hydrogenated at 20° C. and 4 bar over 10% palladium on carbon (3.5 g) for 18 h. Catalyst was removed by filtration and the filtrate was evaporated in vacuo to give a residue which was partitioned between saturated aqueous $NaHCO_3$ (300 mL) and dichloromethane (3×100 mL). The combined organic extracts were dried ($Na_2SO_4$) and evaporated in vacuo to give an oil. Chromatography on silica with 20–50% ether in hexane gradient elution gave the title compound (15.3 g, 59%) as an oil.

Mass spectrum ($API^+$): Found 142 ($MH^+$). $C_7H_8FNO$ requires 141.

Description 37

7-Chloro-5-hydroxy-2-methylquinoline (D37)

The title compound was prepared from 3-chloro-5-methoxyaniline using a similar procedure to Description 34, in 26% yield.

Mass spectrum ($API^+$): Found 194 ($MH^+$). $C_{10}H_8{}^{35}ClNO$ requires 193.

Description 38

5-Hydroxy-3-methylquinoline (D38)

To a stirred solution of N-pivaloyl-3-methoxyaniline (4.14 g, 20 mmol) in dry tetrahydrofuran (80 mL) at 0° C. under argon was added a solution of sec-butyllithium in cyclohexane (1.4 M, 35.7 mL, 50 mmol), dropwise over 0.2 h (T≦0° C.) and the resulting mixture was stirred at 0–5° C. for 2 h. The mixture was cooled to −5° C. then dry N,N-dimethylformamide (2.3 mL, 30 mmol) was added dropwise, and the resulting solution stirred at 0° C. for 1 h then at 20° C. for 20 h. The mixture was cooled to 0° C. and propionaldehyde (1.17 g, 20.2 mmol) was added dropwise followed by a solution of potassium hexamethyldisilazide in toluene (0.5 M, 80 mL, 40 mmol) dropwise over 0.2 h. The mixture was stirred at 0° C. for 0.25 h, then at 20° C. for 2 h and at 30° C. for 1 h. The resulting mixture was partitioned between saturated aqueous $NH_4Cl$ (200 mL) and ether (3×50 mL), and the combined organic extracts dried ($Na_2SO_4$) and evaporated in vacuo. Chromatography of the residue on silica with 20–100% ether in hexane gradient elution gave 5-methoxy-3-methylquinoline (0.16 g, 5%) as an oil. A mixture of 5-methoxy-3-methylquinoline (0.16 g, 0.92 mmol) and pyridine hydrochloride (0.064 g, 5.5 mmol) was heated under argon at 200° C. with stirring for 2.5 h, then cooled and partitioned between saturated aqueous $NaHCO_3$ (30 mL) and dichloromethane (5×30 mL). Combined organic extracts were dried ($Na_2SO_4$) and evaporated in vacuo to give a solid which was purified by chromatography on silica eluting with ethyl acetate to give the title compound (0.089 g, 60%) as a solid.

Mass spectrum ($API^+$): Found 160 ($MH^+$). $C_{10}H_9NO$ requires 159.

Description 39

5-Hydroxycinnoline (D39)

To a mixture of 4-methoxyindole (1.26 g, 8.57 mmol), powdered potassium hydroxide (10.05 g, 0.179 mol) and dry dimethylformamide (20 mL) at 15° C. under argon was added, portionwise over 0.2 h, hydroxylamine-O-sulfonic acid. Internal temperature was kept ≦30° C. by external ice bath cooling. The mixture was stirred at 20° C. for 4 h, then was extracted with toluene (4×50 mL). The combined extracts were washed with water (4×50 mL) and brine (50 mL), then dried ($Na_2SO_4$) and evaporated in vacuo to give an oil. Chromatography of the residue on silica with 5–50% ether in hexane gradient elution gave 1-amino-4-methoxyindole (0.79 g, 56%). A mixture of 1-amino-4-methoxyindole (0.78 g, 4.8 mmol), nitrobenzene (3.4 g, 27.8 mmol), and methanolic HCl (3% w/w, 180 mL) was heated at reflux for 76 h, then cooled and partitioned between 10% aqueous NaOH (50 mL) and dichloromethane (3×30 mL). The combined organic extracts were dried ($Na_2SO_4$) and evaporated in vacuo to give an oil which was purified by chromatography on silica with 5–100% ether in hexane gradient elution. The resulting 5-methoxycinnoline (0.56 g, 3.5 mmol) was mixed with 48% aqueous HBr (35 mL) and the resulting solution heated at reflux for 18 h. The mixture was cooled, then evaporated in vacuo, and the residue dissolved in water (10 mL). Aqueous ammonia (d=0.880) was added until pH 6 was obtained, and the resulting mixture cooled to 0° C. The precipitated solid was collected by filtration and purified by charcoal-methanol treatment to give the title compound (0.37 g, 53%) as a yellow solid.

Mass spectrum ($API^+$): Found 147 ($MH^+$). $C_8H_6N_2O$ requires 146.

Description 40

5-Methoxy-2-methylquinazoline (D40)

To a stirred solution of 2-amino-6-methoxybenzaldehyde [K. Tsuda et al., Chem. Pharm. Bull. 1962, 10, 856] (1.3 g, 8.6 mmol), pyridine (0.81 g, 10.3 mmol) and toluene (60 mL) was added acetic anhydride (0.97 g, 9.5 mmol). The resulting mixture was heated at reflux for 18 h, cooled, then partitioned between saturated aqueous $NaHCO_3$ (100 mL) and ether (50 mL). The organic phase was dried ($Na_2SO_4$) and evaporated in vacuo to give a solid which was purified by chromatography on silica with 0–50% ether in hexane gradient elution to give a colourless solid (1.28 g). The latter was dissolved in 2 M methanolic ammonia (100 mL) and the solution heated at reflux for 3 h, cooled, then evaporated in vacuo. Chromatography of the residue on silica with 0–100% ether in dichloromethane gradient elution gave the title compound (0.92 g, 62%) as a colourless solid.

Mass spectrum ($API^+$): Found 175 ($MH^+$). $C_{10}H_{10}N_2O$ requires 174.

$^1$H NMR ($CDCl_3$) δ: 2.89 (3H, s), 4.02 (3H, s), 6.86 (1H, d, J=8 Hz), 7.49 (1H, d, J=8 Hz), 7.76 (H, t, J=8 Hz), 9.65 (1H, s).

Description 41

5-Hydroxy-2-methylquinazoline (D41)

To a stirred solution of 5-methoxy-2-methylquinazoline (0.22 g, 1.26 mmol) in dichloromethane (20 mL) at 0° C.

under argon was added a solution of boron tribromide in dichloromethane (1M, 3.8 mL), dropwise over 0.01 h. The resulting mixture was stirred at 20° C. for 48 h then poured into a mixture of ice (50 g) and 0.880 aqueous ammonia (50 mL) and stirred for 0.5 h. Organic phase was separated and aqueous phase washed with dichloromethane (3×30 mL). The aqueous phase was acidified (pH 6) with citric acid and the resulting mixture extracted with ethyl acetate (3×50 mL). The combined ethyl acetate extracts were dried ($Na_2SO_4$) and evaporated in vacuo to give the title compound (0.030 g, 15%) as an oil which was used without further purification.

Mass spectrum ($API^+$): Found 161 ($MH^+$). $C_9H_8N_2O$ requires 160.

Description 42

7-Fluoro-5-hydroxy-2-methylquinoline hydrobromide (D42)

Crotonaldehyde (28 mL, 0.33 mol) was added dropwise to a refluxing solution of 3,5-difluoroaniline (10.75 g, 0.083 mol) in 5 N hydrochloric acid (450 mL) and reflux was continued for a further 0.5 h. Reaction mixture was cooled, diluted with water (200 mL) and washed with ether (200 mL). The aqueous layer was basified (pH 14) with 50% NaOH (aq) and extracted into MDC (3×200 mL). The combined organic phases were dried ($Na_2SO_4$) and evaporated in vacuo to give a dark oil which was purified by chromatography on silica gel (~100 g) with 50–100% ethyl acetate in hexane gradient elution to give 5,7-difluoro-2-methylquinoline as a brown solid (6.57 g, 44%). A mixture of 5,7-difluoro-2-methylquinoline (1.0 g, 5.6 mmol) and sodium methoxide (1.69 g, 30 mmol) in methanol (50 mL), was stirred at reflux for 18 h, cooled, and most of the methanol removed in vacuo. The residue was partitioned between ethyl acetate (100 mL), and water (100 mL). The organic phase was dried ($Na_2SO_4$) and evaporated in vacuo to give a brown oil which was purified by chromatography on silica gel (~60 g) with 20–30% ethyl acetate hexane gradient elution to give a yellow solid (0.57 g) which was suspended in 48% HBr (aq) (5 mL) and heated at reflux for 18 h. Reaction mixture was cooled and evaporated in vacuo to give the title compound as a brown solid (0.67 g, 46%).

Mass spectrum ($API^+$): Found 178 ($MH^+$). $C_{10}H_8FNO$ requires 177.

Description 43

7-Iodo-2-methyl-quinolin-5-ol (D43)

The title compound was prepared from 3-iodo-5-methoxyaniline in a similar manner to Description 34

Mass spectrum ($API^+$): Found 286 ($MH^+$). $C_{10}H_8INO$ requires 285.

Description 44

6-Bromo-4-fluoro-3-methoxyaniline (D44)

A mixture of 4-fluoro-3-methoxyaniline (9.87 g, 70 mmol) and N-bromosuccinimide (12.46 g, 70 mmol) in dichloromethane (150 ml) was stirred at room temperature for 1 h (exothermic). The reaction mixture was evaporated in vacuo to give a dark slurry which was chromatographed on silica gel (~350 g) using a gradient elution 20–50% ethyl acetate in hexane to give the title compound as a brown solid (12.70 g, 82%).

Mass spectrum (API): Found 220 ($MH^+$). $C_7H_7{}^{79}BrFNO$ requires 219.

$^1H$ NMR ($CDCl_3$)–3.82 (3H, s), 6.39 (1H, d, J=8 Hz), 7.14 (1H, d, J=11 Hz).

Description 45

8-Bromo-6-fluoro-5-methoxy-2-methylquinoline (D45)

To 6-bromo-4-fluoro-3-methoxyaniline (7.0 g, 32 mmol) was added conc. HCl (10 ml) followed by p-chloranil (7.80 g, 32 mmol), then "butanol (10 ml) was added and the whole mix heated up to reflux, with stirring. A solution of crotonaldehyde (2.7 g 38.4 mmol) in "butanol (5 ml), was added slowly over 0.5 h, and reflux continued for a further 0.5 h. The reaction mixture was allowed to cool, and the basified to pH14 using 50% NaOH solution. The reaction mixture was diluted with water (200 ml) and extracted with dichloromethane (3×100 ml). The combined organic extracts were dried over $Na_2SO_4$ and evaporated in vacuo to give a dark oil which was chromatographed on silica gel (~200 g) eluting from 20% ethyl acetate in hexane to give the title compound as a brown oil (2.97 g, 34%).

Mass spectrum (API): Found 270 ($MH^+$). $C_{11}H_9{}^{79}BrFNO$ requires 269.

$^1H$ NMR ($CDCl_3$) δ: 2.79 (3H, s), 4.13 (3H, m), 7.34 (1H, d, J=9 Hz), 7.82 (1H, d, J=11 Hz), 8.40 (1H, d, J=9 Hz).

Description 46

6-Fluoro-5-methoxy-2-methylquinoline (D46)

A solution of 2-methyl-5-methoxy-6-fluoro-8-bromoquinoline (2.95 g, 10.9 mmol) in ethanol (100 ml) was charged with 10% palladium on charcoal (250 g) and stirred at room temperature and pressure under an atmosphere of hydrogen for 2 h. The mixture was then filtered through a pad of kieselguhr and the filtrate evaporated in vacuo to give the title compound as a brown solid (2.09 g, 100%).

Mass spectrum (API): Found 192 ($MH^+$). $C_{11}H_{10}FNO$ requires 191.

$^1H$ NMR ($CDCl_3$) δ: 3.23 (3H, s), 4.31 (3H, m), 7.62 (1H, d, J=9 Hz), 7.77 (1H, m), 8.77 (1H, m), 9.02 (1H, d, J=9 Hz).

Description 47

6-Fluoro-5-hydroxy-2-methylquinoline (D47)

A mixture of 2-methyl-5-methoxy-6-fluoroquinoline (2.07 g, 10.8 mmol) and 48% hydrobromic acid (30 ml) was stirred at reflux for 24 h. The reaction mix was reduced to minimum volume in vacuo and partitioned between dichloromethane (50 ml) and sat. aqueous sodium bicarbonate solution (50 ml). The organic layer was dried over sodium sulfate, filtered and evaporated in vacuo to give the title compound as a brown solid (1.39 g, 73%).

Mass spectrum (API): Found 178 ($MH^+$). $C_{10}H_8FNO$ requires 177.

$^1H$ NMR ($DMSO-d^6$) δ: 2.62 (3H, s), 7.41 (2H, m), 7.58 (1H, m), 8.43 (1H, d, J=9 Hz).

Description 48

5-(2-Bromoethoxy)-6-fluoro-2-methylquinoline (D48)

The title compound was prepared using a similar procedure to Description 24.

Mass spectrum (API): Found 284 ($MH^+$). $C_{12}H_{11}{}^{79}BrFNO$ requires 283.

¹H NMR (CDCl₃) δ: 2.73 (3H, s), 3.72 (2H, t, J=6 Hz), 4.61 (2H, m), 7.33 (1H, d, J=9 Hz), 7.45 (1H, m), 7.74 (1H, m), 8.54 (1H, d, J=9 Hz).

Description 49

7,8-Difluoro-2-methyl-quinolin-5-ol (D49)

The title compound was prepared from 2,3,5 trifluoroaniline in a similar manner to Description 42.

Mass spectrum (API): Found 198 (MH⁺). $C_{10}H_6F_3N$ requires 197.

¹H NMR (CDCl₃) δ: 2.81 (3H, s), 7.09 (1H, m), 7.38 (1H, d, J=9 Hz), 8.26 (1H, d, J=9 Hz).

Description 50

5-(2-Bromoethoxy)-7,8-difluoro-2-methylquinoline (D50)

The title compound was prepared using the procedure described in Description 24.

Mass spectrum (API): Found 302 (MH⁺). $C_{12}H_{10}{}^{79}BrF_2NO$ requires 301.

¹H NMR (CDCl₃) δ: 2.78 (3H, s), 3.68 (2H, m), 4.55 (2H, m), 7.00 (1H, m), 7.29 (1H, m), 8.21 (1H, m).

Description 51

2,3-Difluoro-4-hydroxy-5-nitro-benzoic acid methyl ester (D51)

Concentrated nitric acid (70% w/w) (0.72 mL, 11.2 mmol) in glacial acetic acid (2 mL) was added dropwise to a solution of 2,3-difluoro-4-hydroxy-benzoic acid methyl ester [Gonzales, Javier et al., PCT Int. Appl. (1999), 551 pp. WO 9901423 A1 19990114] (2 g, 10.6 mmol) in glacial acetic acid (28 mL). The mixture was stirred at 45° C. for 0.5 hour and then at room temperature overnight before it was evaporated to a quarter of the volume in vacuo. Water was added to the concentrate to give a solid precipitate which was filtered, washed with water twice and dried to give the title compound (2.2 g, 88%) as a colourless solid.

¹H NMR (DMSO-d₆) δ: 3.86 (3H, s), 8.27 (1H, dd, J=10, 3 Hz).

Description 52

5-Amino-2,3-difluoro-4-hydroxy-benzoic acid methyl ester (D52)

A solution of 2,3-difluoro-4-hydroxy-5-nitro-benzoic acid methyl ester (2.2 g, 9.4 mmol) in methanol (100 mL) was stirred under atmospheric hydrogen at ambient temperature in the presence of 10% palladium on charcoal (0.8 g) for 3 hours. The mixture was filtered and the filtrate was evaporated in vacuo to give the title compound (1.9 g, 100%) as a colourless solid.

¹H NMR (CDCl₃) δ: 3.87 (3H, s), 7–02 (1H, dd, J=10.3 Hz).

Description 53

7,8-Difluoro-6-methoxycarbonyl-4H-benzo[1,4]oxazine-3-one (D53)

A mixture of 5-amino-2,3-difluoro-4-hydroxy-benzoic acid methyl ester (5.5 g, 27.1 mmol) and benzyl-triethylammonium chloride (6.2 g) in chloroform (300 mL) was warmed and sonicated until most of the solid was dissolved. The mixture was cooled in an ice bath and sodium hydrogen carbonate (10 g) was added, followed by chloroacetyl chloride (2.4 mL, 29 mmol). The combined mixture was stirred in cold for 1 hour and then under reflux for approximately 9 hours. It was then evaporated in vacuo and the resulting residue was treated with water and chloroform to give a solid. This solid was collected by filtration, washed with water, diethyl ether and dried in vacuo to give the title compound (3.7 g, 56%).

¹H NMR (DMSO-d₆) δ: 3.85 (3H, s), 4.78 (2H, s), 7.21 (1H, dd, J=10, 3 Hz).

Description 54

7,8-Difluoro-4H-benzo[1,4]oxazine-3-one-6-carboxylic acid, (D54)

A 2M solution of aqueous sodium hydroxide (30 mL) was added to a suspension of 7,8-difluoro-6-methoxycarbonyl-4H-benzo[1,4]oxazine-3-one (4.8 g, 19.88 mmoL) in THF (100 mL). The mixture was allowed to stir for 3 hours and the total volume was then reduced in vacuo to half. It was treated with 2M hydrochloric acid to caused a solid precipitate which was filtered, washed with water three times and then dried in vacuo to give the title compound (3.6 g, 80%).

¹H NMR (DMSO-d₆) δ: 4.79 (2H, s), 7.22 (1H, dd, J=10, 3 Hz), 11.05 (1H, br s), 13.41 (1H, br, s).

Description 55

7,8-Difluoro-6-hydroxymethyl-4H-benzo[1,4]oxazin-3-one (D55)

Triethylamine (2.4 mL, 17.3 mmol) was added to a suspension of 7,8-difluoro-4H-benzo[1,4]oxazine-3-one-6-carboxylic acid (3.6 g, 15.7 mmol) in anhydrous THF (250 mL). Isobutyl chloroformate (2.2 mL, 17.3 mmol) was added to the mixture at ice cold temperature over 0.5 hour. Stirring was continued for further 2 hours at room temperature. It was then cooled in ice and the solid was removed by filtration. The filtrate was added to a cold solution of sodium borohydride (3.2 g) in water. The mixture was stirred in cold for 1 hour before it was concentrated in vacuo to half and acidified with 2M hydrochloric acid. The resulting solid precipitate was collected by filtration and dried to give the title compound (1.15 g, 22%).

¹H NMR (DMSO-d₆) δ: 4.47 (1H, d, J=8 Hz), 4.68 (2H, s), 5.38 (1H, t, J=9 Hz), 6.79 (1H, dd, J=10, 3 Hz), 10.92 (1H, br, s),

Description 56

7,8-Difluoro-6-formyl-3-oxo-3,4-dihydro-4H-benzo[1,4]oxazin-3-one (D56)

Manganese dioxide (2.3 g, 26.3 mmol) was added to a mixture of 7,8-difluoro-6-hydroxymethyl-4H-benzo[1,4]oxazin-3-one (1.13 g, 5.25 mmol), dichloromethane (70 mL) and THF (50 mL). The mixture was stirred for 6 hours and then filtered through celite. The filtrate was evaporated in vacuo to give the title compound (1.02 g, 80%) as a pale yellow solid.

¹H NMR (DMSO-d₆) δ: 4.84 (2H, s), 7.10 (1H, dd, J=10, 3 Hz), 10.07 (1H, s), 11.14 (1H, br, s).

Description 57

Diethyl 3-fluoro-4-methoxybenzyl phosphonate (D57)

A mixture of 3-fluoro-4-methoxybenzyl chloride [Cervena, Irena; Holubek, Jiri; Svatek, Emil; Valchar, Martin; Protiva, Miroslav; Collect. Czech. Chem. Commun.; 52; 10; 1987; 2564–2571.] (6 g, 35 mmol) and triethylphosphite (23 g, 140 mmol) was stirred under reflux for 16 hours. Removal of the excess triethylphosphite in vacuo gave the title compound (11.2 g, 100%) as an amber oil.

Mass spectrum (API$^+$): Found 277 (MH$^+$). $C_{12}H_{18}FO_4P$ requires 276.

$^1$H NMR (CDCl$_3$) δ: 1.26 (6H, m), 3.06 (2H, d, J=21 Hz), 3.87 (3H, s), 3.90–4.10 (4H, m), 6.90 (1H, t, J=8 Hz), 6.95–7.05 (2H, m).

Description 58

4-(3-Fluoro-4-methoxy-benzylidene)-piperidine-1-carboxylic acid tert-butyl ester (D58)

A 1M solution of potassium tert-butoxide in THF (24 mL, 24 mmol) was added dropwise to a stirring solution of diethyl 3-fluoro-4-methoxybenzyl phosphonate (6 g, 22 mmol) in anhydrous THF (10 mL) at room temperature. Upon completion of the addition, stirring was continued for 45 mins. 4-oxo-piperidine-1-carboxylic acid tert-butyl ester (4.8 g, 24.2 mmol) in anhydrous THF (10 mL) was added. The mixture was left to stir for 16 hours before it was quenched with saturated ammonium chloride (250 mL). Extraction with diethyl ether (200 mL) twice and evaporation of the combined organic layer gave a crude oil. Silica gel chromatography eluting with ethyl acetate in hexane (5–15%) gave the title compound (4.7 g, 66%) as a colourless oil.

$^1$H NMR (CDCl$_3$) δ: 1.48 (9H, s), 2.31 (2H, m), 2.44 (2H, m), 3.40 (2H, m), 3.50 (2H, m), 3.88 (3H, s), 6.25 (1H, s), 6.80–7.00 (3H, m).

Description 59

4-(3-Fluoro-4-methoxy-benzyl)-piperidine-1-carboxylic acid tert-butyl ester (D59)

A solution of 4-(3-fluoro-4-methoxy-benzylidene)-piperidine-1-carboxylic acid tert-butyl ester (4.7 g, 14.6 mmol) in methanol (400 mL) was allowed to stir under atmospheric pressure of hydrogen at room temperature in the presence of 10% palladium on carbon (0.8 g) for 16 hours. Removal of the catalyst by filtration and evaporation of the filtrate gave a crude oil. Silica gel chromatography eluting with ethyl acetate in hexane (10%) gave the title compound (4.3 g, 99%) as a colourless oil.

$^1$H NMR (CDCl$_3$) δ: 1.05–1.20 (2H, m), 1.45 (9H, s), 1.55–1.65 (3H, m), 2.46 (2H, d, J=6 Hz), 2.60–2.70 (2H, m), 3.86 (3H, s), 4.00–4.15 (2H, m), 6.75–6.90 (3H, m).

Description 60

2-Fluoro-4-piperidin-4-ylmethyl-phenol, hydrogen sulfate salt (D60)

A solution of 4-(3-fluoro-4-methoxy-benzyl)-piperidine-1-carboxylic acid tert-butyl ester (0.26 g, 0.81 mmol) in methanol (1 mL) and diethyl ether (5 mL) was allowed to stir under reflux in the presence of concentrated sulfuric acid (0.088 g) for 1.5 hours. The solvents were removed in vacuo to give a colourless oil which was treated with glacial acetic acid (10 mL) and 48% w/w hydrobromic acid (10 mL). The mixture was heated under reflux for 4 hours before it was evaporated to dryness in vacuo to give an amber solid (0.24 g, 100%).

Mass spectrum (API$^+$): Found 210 (MH$^+$). $C_{12}H_{16}FNO$ requires 209.

$^1$H NMR (CD$_3$OD) δ: 1.30–1.45 (2H, m), 1.75–1.95 (3H, m), 2.52 (2H, d, J=7 Hz), 2.80–3.00 (2H, m), 3.30–3.40 (2H, m), 6.975–8.00 (3H, m).

Description 61

4-(3-Fluoro-4-hydroxy-5-nitro-benzyl)-piperidine-1-carboxylic acid tert-butyl ester (D61)

A solution of 70% w/w nitric acid (0.08 g, 0.81 mmol) in glacial acetic acid (0.5 mL) was added dropwise to a stirred solution of 2-fluoro-4-piperidin-4-ylmethyl-phenol hydrogen sulfate (0.24 g, 0.81 mmol) and acetic anhydride (0.099 g, 0.097 mmol) at room temperature. The mixture was left to stir for 16 hours before it was evaporated in vacuo. The residue was dissolved in water (15 mL) and basified with sodium bicarbonate before being treated with triethylamine (2 mL) and di-tert-butyl dicarbonate (0.21 g, 0.97 mmol) in THF (10 mL). After 16 hours of stirring, the mixture was partitioned between ethyl acetate (80 mL) and water (60 mL). The aqueous layer was extracted with more ethyl acetate (80 mL). The combined organic layer was dried (Na$_2$SO$_4$) and evaporated in vacuo. Chromatography of the residue on silica eluting with ethyl acetate in hexane (10%–50%) gave the title compound (60 mg, 21%) as a yellow solid.

Mass spectrum (API$^-$): Found 353 ([M−H]$^-$). $C_{17}H_{23}FN_2O_5$ requires 354.

$^1$H NMR (CDCl$_3$) δ: 1.10–1.25 (2H, m), 1.45 (9H, s), 1.55–1.65 (3H, m), 2.53 (2H, d, J=7 Hz), 2.55–2.65 (2H, m), 4.00–4.20 (2H, m), 7.23 (1H, dd, J=10, 2 Hz), 7.68 (1H, m).

Description 62

4-(3-Fluoro-4-methoxycarbonylmethoxy-5-nitro-benzyl)-piperidine-1-carboxylic acid tert-butyl ester (D62)

The title compound was prepared in a similar manner to Description 10.

$^1$H NMR (CDCl$_3$) δ: 1.10–1.25 (2H, m), 1.45 (9H, s), 1.55–1.75 (3H, m), 2.55 (2H, d, J=7 Hz), 2.60–2.75 (2H, m), 3.79 (3H, s), 4.05–4.20 (2H, m), 4.79 (2H, s), 7.12 (1H, dd, J=10, 2 Hz), 7.40 (1H, m).

Description 63

6-(4-(N-(t-Butyloxycarbonyl)piperidinyl)methyl)-8-fluoro-4H-benzo[1,4]oxazin-3-one (D63)

The title compound was prepared in a similar manner to Description 5.

$^1$H NMR (CDCl$_3$) δ: 1.05–1.20 (2H, m), 1.45 (9H, s), 1.50–1.70 (3H, m), 2.44 (2H, d, J=7 Hz), 2.55–2.70 (2H, m), 4.00–4.15 (2H, m), 4.66 (2H, s), 6.36 (1H, s), 6.60 (1H, dd, J=10, 2 Hz), 8.11 (1H, s).

Description 64

6-(4-(Piperidinylmethyl)-8-fluoro-4H-benzo[1,4]oxazin-3-one hydrochloride (D64)

The title compound was prepared in a similar manner to Description 6.

$^1$H NMR (DMSO-d$_6$) δ: 1.20–1.40 (2H, m), 1.60–1.80 (3H, m), 2.40–2.46 (2H, m), 2.70–2.90 (2H, m), 3.15–3.30 (2H, m), 4.62 ((2H, s), 6.51 (1H, s), 6.74 (1H, dd, J=11, 2 Hz), 8.30–8.80 (2H, br, m), 10.87 (1H, s).

Description 65

6-(4-(N-(t-Butyloxycarbonyl)piperidinyl)methyl)-8-fluoro-4-methyl-4H-benzo[1,4]oxazin-3-one (D65)

The title compound was prepared in a similar manner to Description 7.

¹H NMR (CDCl₃) δ: 1.05–1.20 (2H, m), 1.45 (9H, s), 1.60–1.70 (3H, m), 2.49 (2H, d, J=8 Hz), 2.60–2.75 (2H, m), 3.35 (3H, s), 4.00–4.15 (2H, m), 4.66 (2H, s), 6.51 (1H, s), 6.64 (1H, dd, J=10, 2 Hz).

Description 66

8-Fluoro-4-methyl-6-(4-(piperidinylmethyl))-4H-benzo[1,4]oxazin-3-one hydrochloride (D66)

The title compound was prepared in a similar manner to Description 6.

¹H NMR (DMSO-d₆) δ: 1.20–1.40 (2H, m), 1.60–1.75 (2H, m), 1.78–1.90 (1H, m), 2.75–2.90 (2H, m), 3.20–3.27 (2H, m), 3.30 (3H, s), 4.70 (2H, s), 6.80–6.90 (2H, m), 8.35 (1H, br. s), 8.65 (1H, br. s).

Description 67

Diethyl 2-fluoro-4-methoxybenzyl phosphonate (D67)

The title compound was prepared in a similar manner to Description 57.

Mass spectrum (API⁺): Found 277 (MH⁺). $C_{12}H_{18}FO_4P$ requires 276.

¹H NMR (CDCl₃) δ: 1.27 (6H, t, J=5 Hz), 3.06 (2H, d, J=21 Hz), 3.78 (3H, s), 4.00 (4H, m), 6.60–6.75 (2H, m), 7.20–7.30 (1H, m).

Description 68

4-(2-Fluoro-4-methoxy-benzylidene)-piperidine-1-carboxylic acid tert-butyl ester (D68)

The title compound was prepared in a similar manner to Description 58.

¹H NMR (CDCl₃) δ: 1.47 (9H, s), 2.25–2.40 (4H, m), 3.35–3.45 (2H, m), 3.45–3.55 (2H, m), 3.79 (3H, s), 6.20 (1H, s), 6.55–6.70 (2H, m), 7.07 (1H, t, J=9 Hz).

Description 69

4-(2-Fluoro-4-methoxy-benzyl)-piperidine-1-carboxylic acid tert-butyl ester (D69)

The title compound was prepared in a similar manner to Description 59.

¹H NMR (CDCl₃) δ: 1.05–1.20 (2H, m), 1.45 (9H, s), 1.55–1.70 (3H, m), 2.50 (2H, d, J=6 Hz), 2.55–2.70 (2H, m), 3.78 (3H, s), 4.00–4.15 (2H, m), 6.55–6.65 (2H, m), 7.00 (1H, t, J=9 Hz).

Description 70

3-Fluoro-4-piperidin-4-ylmethyl-phenol, hydrogen sulfate salt (D70)

The title compound was prepared in a similar manner to Description 60.

Mass spectrum (API⁺): Found 210 (MH⁺). $C_{12}H_{16}FNO$ requires 209.

¹H NMR (DMSO-d₆) δ: 1.20–1.40 (2H, m), 1.65–1.80 (3H, m), 2.44 (2H, d, J=6 Hz), 2.75–2.85 (2H, m), 3.15–3.30 (2H, m), 6.45–6.60 (2H, m), 7.03 (1H, t, J=8 Hz), 8.10 (1H, br s), 8.42 (1H, br s), 9.67 (1H, br, s).

Description 71

4-(2-Fluoro-4-hydroxy-5-nitro-benzyl)-piperidine-1-carboxylic acid tert-butyl ester (D71)

The title compound was prepared in a similar manner to Description 61.

Mass spectrum (API⁻): Found 353 ([M–H]⁻). $C_{17}H_{23}FN_2O_5$ requires 354.

¹H NMR (CDCl₃) δ: 1.10–1.25 (2H, m), 1.45 (9H, s), 1.55–1.75 (3H, m), 2.55 (2H, d, J=7 Hz), 2.60–2.75 (2H, m), 4.00–4.20 (2H, m), 6.82 (1H, d, J=10 Hz), 7.94 (1H, d, J=8 Hz).

Description 72

4-(2-Fluoro-4-methoxycarbonylmethoxy-5-nitro-benzyl)-piperidine-1-carboxylic acid tert-butyl ester (D72)

The title compound was prepared in a similar manner to Description 10.

¹H NMR (CDCl₃) δ: 1.10–1.25 (2H, m), 1.45 (9H, s), 1.55–1.75 (3H, m), 2.56 (2H, d, J=7 Hz), 2.60–2.70 (2H, m), 3.83 (3H, s), 4.05–4.20 (2H, m), 4.76 (2H, s), 6.67 (1H, d, J=10 Hz), 7.79 (1H, d, J=7 Hz).

Description 73

6-(4-(N-(t-Butyloxycarbonyl)piperidinyl)methyl)-7-fluoro-4H-benzo[1,4]oxazin-3-one (D73)

The title compound was prepared in a similar manner to Description 5.

¹H NMR (CDCl₃) δ: 1.05–1.20 (2H, m), 1.45 (9H, s), 1.55–1.75 (3H, m), 2.49 (2H, d, J=7 Hz), 2.60–2.70 (2H, m), 4.00–4.10 (2H, m), 4.60 (2H, s), 6.58 (1H, d, J=8 Hz), 6.90 (1H, d, J=10, 2 Hz), 8.85 (1H, s).

Description 74

6-(4-(Piperidinylmethyl)-7-fluoro-4H-benzo[1,4]oxazin-3-one hydrochloride (D74)

The title compound was prepared in a similar manner to Description 6.

Mass spectrum (API⁺): Found 265 (MH⁺). $C_{14}H_{17}FN_2O_2$ requires 264.

EXAMPLE 1

6-(4-(1-(2-(4-1H-Indolyloxy)ethyl)piperidinyl)oxy)-4H-benzo[1,4]oxazin-3-one (E1)

A mixture of 6-(4-piperidinyloxy)-4H-benzo[1,4]oxazin-3-one hydrochloride (0.10 g, 0.35 mmol), 4-1H-indolyloxyacetaldehyde [H. Sasai et al., Tetrahedron 1994, 43, 12313] (0.062 g, 0.35 mmol) and sodium triacetoxyborohydride (0.11 g, 0.53 mmol) in 1,2-dichloroethane (10 mL) was stirred at 20° C. for 18 h. The mixture was then partitioned between saturated NaHCO₃ aq (20 mL) and dichloromethane (3×15 mL). Combined organic extracts were dried (Na₂SO₄) and evaporated in vacuo. Chromatography of the residue on SiO₂ eluting with 0–20% methanol in ethyl acetate gave the title compound (0.090 g, 63%) as an oil.

Mass spectrum (API⁺): Found 408 (MH⁺). $C_{23}H_{25}N_3O_4$ requires 407.

¹H NMR (CDCl₃) δ: 1.84 (2H, m), 2.01 (2H, m), 2.54 (2H, m), 2.85–3.00 (4H, m), 4.21 (1H, m), 4.29 (2H, d, J=6 Hz), 4.56 (2H, s), 6.37 (1H, d, J=3 Hz), 6.52 (2H, m), 6.64 (1H, m), 6.87 (1H, d, J=9 Hz), 7.00–7.13 (3H, m), 8.15 (1H, br s), 8.21 (1H, br s).

EXAMPLE 2

6-(4-(1-(2-(4-(2-Cyano)-1H-indolyloxy)ethyl)piperidinyl)oxy)-4H-benzo[1,4]oxazin-3-one (E2)

The title compound was prepared in a similar manner to Example 1.

Mass spectrum (API⁺): Found 433 (MH⁺). $C_{24}H_{24}N_4O_4$ requires 432.

¹H NMR (CDCl₃) δ: 1.84 (2H, m), 2.01 (2H, m), 2.53 (2H, m), 2.93 (4H, m), 4.26 (3H, m), 4.55 (2H, s), 6.38 (1H, d, J=2 Hz), 6.53 (2H, m), 6.88 (1H, d, J=9 Hz), 6.98 (1H, d, J=8 Hz), 7.23 (2H, m), 8.07 (1H, br s), 8.97 (1H, br s).

EXAMPLE 3

6-(4-(1-(3-(2-(5-Isoxazolyl)phenoxy)propyl) piperidinyl)oxy)-4H-benzo[1,4]oxazin-3-one (E3)

A mixture of 6-(4-(piperidinyl)oxy)-4H-benzo[1,4] oxazin-3-one hydrochloride (100 mg, 0.35 mmol), 3-(2-(5-isoxazolyl)phenoxy)propyl bromide (99 mg, 0.39 mmol), diisopropylethylamine (149 mg, 1.155 mmol) in isopropyl alcohol (8 mL) was heated at reflux with stirring in a reaction block for 48 h. The reaction mixture was cooled, and the isopropyl alcohol evaporated in vacuo. The residue was partitioned between dichloromethane (5 mL), and water (5 mL). The organic layer was added onto a 10 g pre-packed silica column and eluted with 0–10% methanol in ethyl acetate. Fractions containing desired material were combined and evaporated in vacuo give the title compound (50 mg, 32%) as a colourless oil.

Mass spectrum (API⁺): Found 450 (MH⁺). $C_{25}H_{27}N_3O_5$ requires 449.

¹H NMR (CDCl₃) δ: 1.82 (2H, m), 1.95 (2H, m), 2.10 (2H, m), 2.31 (2H, m), 2.57 (2H, m), 2.75 (2H, m), 4.19 (3H, m), 4.56 (1H, s), 6.39 (1H, d, J=2 Hz), 6.52 (1H, dd, J=9, 2 Hz), 6.80 (1H, d, J=2 Hz), 6.88 (1H, d, J=9 Hz), 7.05 (2H, m) 7.37 (1H, m), 7.99 (1H, dd, J=8, 2 Hz), 8.03 (1H, br s), 8.30 (1H, d, J=2 Hz).

EXAMPLE 4

6-(4-(1-(5-(1-Quinolinyloxy)ethyl)piperidinyl) methyl)-4H-benzo[1,4]oxazin-3-one (E4)

A mixture of 6-(4-piperidinylmethyl)-4H-benzo[1,4] oxazin-3-one hydrochloride (0.11 g, 0.4 mmol). 2-(5-quinolinyloxy)ethyl bromide (0.1 g, 0.4 mmol) and diisopropylethylamine (0.16 g, 1.2 mmol) in isopropanol (5 mL) was heated under reflux for 48 hours. The isopropanol was evaporated in vacuo. Chromatography of the residue on silica gel eluting with methanol in ethyl acetate (0%–5%) followed by 0.880 ammonia/methanol/ethyl acetate (5/5/90) gave the title compound (0.03 g, 18%).

Mass spectrum (API⁺): Found 418 (MH⁺). $C_{25}H_{27}N_3O_3$ requires 417.

¹H NMR (CDCl₃) δ: 1.31–1.38 (2H, m), 1.49 (1H, m), 1.64 (2H, m), 2.14 (2H, m), 2.46 (2H, d, J=7 Hz), 2.94 (2H, t, J=5 Hz), 3.05 (2H, m), 4.29 (2H, t, J=5 Hz), 4.58 (2H, s), 6.55 (1H, s), 6.74 (1H, d, J=8 Hz), 6.87 (2H, m), 7.37 (1H, dd, J=8, 4 Hz), 7.60 (1H, t, J=8 Hz), 7.69 (1H, d, J=8 Hz), 8.04 (1H, s), 8.55 (1H, d, J=8 Hz), 8.90 (1H, m).

EXAMPLE 5

6-(4-(1-(3-(2-Cyanophenoxy)propyl)piperidinyl) oxy)-4H-benzo[1,4]oxazin-3-one (E5)

The title compound was prepared in a similar manner to Example 3.

Mass spectrum (API⁺): Found 408 (MH⁺). $C_{23}H_{25}N_3O_4$ requires 407.

¹H NMR (CDCl₃) δ: 1.78 (2H, m), 1.99 (4H, m), 2.27 (2H, m), 2.56 (2H, t, J=7 Hz), 2.77 (2H, m), 4.17 (3H, m), 4.56 (2H, s), 6.40 (1H, d, J=3 Hz), 6.52 (1H, dd, J=9 Hz, 3 Hz), 6.87 (1H, d, J=9 Hz), 6.99 (2H, m), 7.52 (1H, m), 8.15 (1H, br, s).

EXAMPLE 6

6-(4-(1-(3-(7-(2,2-Dimethyl-2,3-dihydro)benzo[b] furanyloxy)propyl)piperidinyl)-oxy)-4H-benzo[1,4] oxazin-3-one (E6)

The title compound was prepared in a similar manner to Example 3.

Mass spectrum (API⁺): Found 453 (MH⁺). $C_{26}H_{32}N_2O_5$ requires 452.

¹H NMR (CDCl₃) δ: 1.49 (6H, s), 1.80 (2H, m), 1.88–2.07 (4H, m), 2.29 (2H, m), 2.54 (2H, t, J=6 Hz), 2.75 (2H, m), 3.01 (2H, s), 4.12 (2H, t, J=6 Hz), 4.18 (1H, m), 4.55 (2H, s), 6.43 (1H, d, J=3 Hz), 6.52 (1H, dd, J=9, 3 Hz), 6.75 (3H, m), 6.85 (1H, d, J=9 Hz), 9.00 (1H, br s).

EXAMPLE 7

6-(4-(1-(2-(7-(2,2-Dimethyl-2,3-dihydro)benzo[b] furanyloxy)ethyl)piperidinyl)oxy)-4-methyl-4H-benzo[1,4]oxazin-3-one (E7)

The title compound was prepared in a similar manner to Example 3.

Mass spectrum (API⁺): Found 453 (MH⁺). $C_{26}H_{32}N_2O_5$ requires 452.

¹H NMR (CDCl₃) δ: 1.49 (6H, s), 1.82 (2H, m), 1.98 (2H, m), 2.43 (2H, m), 2.84 (4H, m), 3.01 (2H, s), 3.33 (3H, s), 4.22 (3H, m), 4.55 (2H, s), 6.53 (2H, m), 6.76 (3H, m), 6.88 (1H, d, J=9 Hz).

EXAMPLE 8

6-(4-(1-(2-(1-naphthyloxy)ethyl)piperidinyl)oxy)-4-methyl-4H-benzo[1,4]oxazin-3-one (E8)

The title compound was prepared in a similar manner to Example 3.

Mass spectrum (API⁺): Found 433 (MH⁺). $C_{26}H_{28}N_2O_4$ requires 432.

¹H NMR (CDCl₃) δ: 1.84 (2H, m), 2.01 (2H, m), 2.51 (2H, m), 2.97 (4H, m), 3.31 (3H, s), 4.27 (3H, m), 4.55 (2H, s), 6.53 (2H, m), 6.84 (2H, m), 7.43 (4H, m), 7.79 (1H, m), 8.24 (1H, m).

EXAMPLE 9

(±)-6-(3-(1-(3-(2-Cyanophenoxy)propyl)piperidinyl) methoxy)-4H-benzo[1,4]oxazin-3-one (E9)

The title compound was prepared in a similar manner to Example 3.

Mass spectrum (API⁺): Found 422 (MH⁺). $C_{24}H_{27}N_3O_4$ requires 421.

¹H NMR (CDCl₃) δ: 1.16 (1H, m), 1.53–1.83 (4H, m), 1.97 (1H, m), 1.99–2.12 (3H, m), 2.55 (2H, t, J=6 Hz), 2.80 (1H, m), 2.97 (1H, m), 3.79 (2H, m), 4.12 (2H, t, J=6 Hz), 4.54 (2H, s), 6.39 (1H, d, J=3 Hz), 6.49 (1H, dd, J=9, 3 Hz), 6.86 (1H, d, J=9 Hz), 6.92–7.02 (2H, m), 7.44–7.58 (2H, m), 8.12 (1H, br s).

EXAMPLE 10

(±)-6-(3-(1-(3-(2-Cyanophenoxy)propyl) pyrrolidinyl)methoxy)-4H-benzo[1,4]oxazin-3-one (E10)

The title compound was prepared using a similar method to Example 3.

Mass spectrum (API⁺): Found 408 (MH⁺). $C_{23}H_{25}N_3O_4$ requires 407.

¹H NMR (CDCl₃) δ: 1.61 (2H, m), 2.06 (2H, m), 2.49 (1H, m), 2.56–2.81 (6H, m), 3.83 (2H, d, J=7 Hz), 4.14 (2H, t, J=6 Hz), 4.56 (2H, s), 6.37 (1H, d, J=3 Hz), 6.50 (1H, dd, J=9, 3 Hz), 6.88 (1H, d, J=9 Hz), 6.97 (2H, m), 7.46–7.58 (2H, m), 7.89 (1H, br s).

EXAMPLE 11

6-(4-(1-(3-(2-(5-Isoxazolyl)phenoxy)propyl)piperazinyl)methyl)-4H-benzo[1,4]oxazin-3-one (E11)

A mixture of 6-(4-Piperazinylmethyl)-4H-benzo[1,4]oxazin-3-one dihydrochloride (550 mg, 1.72 mmol), 3-(2-(5-isoxazolyl)phenoxy)propyl bromide (485 mg, 1.72 mmol), diisopropylethylamine (1.2 mL, 6.9 mmol,) in isopropyl alcohol (30 mL) was heated at reflux with stirring in a reaction block for 48 h. The reaction mixture was cooled, and the isopropyl alcohol evaporated in vacuo. The residue was partitioned between dichloromethane (25 mL) and water (25 mL). The organic layer was added onto silica gel (30 g) and eluted with 0–10% methanol in ethyl acetate. Fractions containing desired material were combined and evaporated in vacuo to give the title compound as a yellow oil (2.80 mg, 36%).

Mass spectrum (API⁺): Found 449 (MH⁺). $C_{25}H_{28}N_4O_4$ requires 448.

¹H NMR (CDCl₃) δ: 2.11 (2H, m), 2.52 (10H, m), 3.43 (2H, s), 4.14 (2H, m), 4.61 (2H, s), 6.79 (2H, m), 6.91 (2H, s), 7.03 (2H, m), 7.38 (1H, m), 7.99 (1H, dd, J=8.2 Hz), 8.07 (1H, br s), 8.29 (1H, d, J=2 Hz).

The examples of Tables 1–6 were prepared in a similar manner to Example 1 or Example 3.

TABLE 1

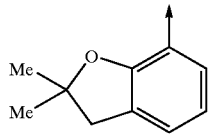

| Example | Ar | m | R¹ | Mass spectrum (API⁺) |
|---|---|---|---|---|
| E12 | 2,3-dichlorophenyl | 2 | H | Found 438 (MH⁺). $C_{21}H_{22}Cl_2N_2O_2$ requires 437. |
| E13 | 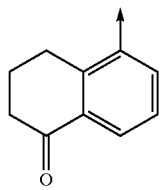 | 2 | H | Found 439 (MH⁺). $C_{25}H_{30}N_2O_5$ requires 438. |
| E14 | 3-bromophenyl | 2 | H | Found 447 (MH⁺). $C_{21}H_{23}{}^{79}BrN_2O_4$ requires 446. |
| E15 | 3-methylphenyl | 2 | H | Found 383 (MH⁺). $C_{22}H_{26}N_2O_4$ requires 382. |
| E16 | 2-(5-isoxazolyl)phenyl | 2 | H | Found 436 (MH⁺). $C_{24}H_{25}N_3O_5$ requires 435. |
| E17 | 1-naphthyl | 2 | H | Found 419 (MH⁺). $C_{25}H_{26}N_2O_4$ requires 418. |
| E18 | (3-trifluoromethyl)phenyl | 2 | H | Found 437 (MH⁺). $C_{22}H_{23}F_3N_2O_4$ requires 436. |
| E19 | (3-ethyl-4-chloro)phenyl | 2 | H | Found 431 (MH⁺). $C_{26}H_{30}N_2O_5$ requires 430. |
| E20 | 2-propylphenyl | 2 | H | Found 411 (MH⁺). $C_{24}H_{30}N_2O_4$ requires 410. |
| E21 |  | 3 | H | Found 451 (MH⁺). $C_{26}H_{30}N_2O_5$ requires 450. |
| E22 | 5-quinolinyl | 2 | H | Found 420 (MH³⁰). $C_{24}H_{25}N_3O_4$ requires 419. |
| E23 | 2-(5-isoxazolyl)phenyl | 2 | Me | Found 450 (MH⁺). $C_{25}H_{27}N_3O_5$ requires 449. |
| E24 | 1-isoquinolinyl | 2 | H | Found 420 (MH⁺). $C_{24}H_{25}N_3O_4$ requires 419. |

TABLE 1-continued

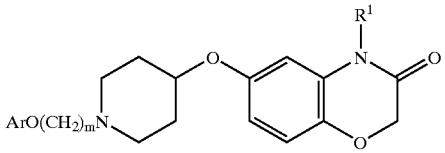

| Example | Ar | m | R¹ | Mass spectrum (API⁺) |
|---|---|---|---|---|
| E25 | 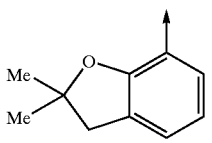 | 2 | H | Found 443 (MH⁺).<br>$C_{24}H_{27}FN_2O_5$ requires 442. |
| E26 | 8-quinolinyl | 2 | H | Found 420 (MH⁺).<br>$C_{24}H_{25}N_3O_4$ requires 419. |
| E27 | 7-benzo[b]furanyl | 2 | H | Found 409 (MH⁺).<br>$C_{23}H_{24}N_2O_5$ requires 408. |
| E28 | 7-(2,3-dihydro)benzo[b]furanyl | 2 | H | Found 411 (MH⁺).<br>$C_{23}H_{26}N_2O_5$ requires 410. |
| E29 | 7-(2,3-dihydro)beno[b]furanyl | 2 | Me | Found 425 (MH⁺).<br>$C_{24}H_{28}N_2O_5$ requires 424. |
| E30 | 7-benzo[b]furanyl | 2 | Me | Found 423 (MH⁺).<br>$C_{24}H_{26}N_2O_5$ requires 422 |
| E31 | 2-(5-isoxazolyl)phenyl | 3 | Me | Found 464 (MH⁺).<br>$C_{26}H_{29}N_3O_5$ required 463. |
| E32 | 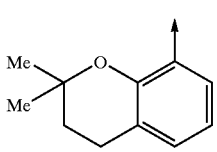 | 3 | Me | Found 467 (MH⁺).<br>$C_{27}H_{34}N_2O_5$ requires 466. |
| E33 | 7-benzo[b]furanyl | 3 | H | Found 423 (MH⁺).<br>$C_{24}H_{26}N_2O_5$ requires 422. |
| E34 | 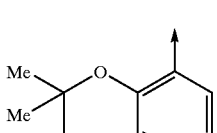 | 3 | H | Found 467 (MH⁺).<br>$C_{27}H_{34}N_2O_5$ requires 466. |
| E35 | 7-(2-methyl)benzo[b]furanyl | 3 | H | Found 437 (MH⁺).<br>$C_{25}H_{28}N_2O_5$ requires 436. |
| E36 | 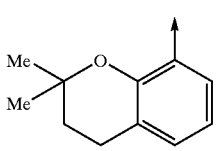 | 3 | Me | Found 481 (MH⁺).<br>$C_{28}H_{36}N_2O_5$ requires 480. |
| E37 | 7-(2-methyl)benzo[b]furanyl | 3 | Me | Found 451 (MH⁺).<br>$C_{26}H_{30}N_2O_5$ requires 450. |
| E38 | 7-(2-methyl)benzo[b]furanyl | 2 | Me | Found 437 (MH⁺).<br>$C_{25}H_{28}N_2O_5$ requires 436. |
| E39 | 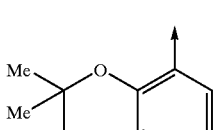 | 2 | H | Found 453 (MH⁺).<br>$C_{26}H_{32}N_2O_5$ requires 452. |
| E40 |  | 2 | Me | Found 467 (MH⁺).<br>$C_{27}H_{34}N_2O_5$ requires 466. |

TABLE 1-continued

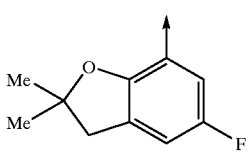

| Example | Ar | m | R¹ | Mass spectrum (API⁺) |
|---|---|---|---|---|
| E41 | 5-quinolinyl | 9 | Me | Found 434 (MH⁺). $C_{25}H_{27}N_3O_4$ requires 433. |
| E42 | 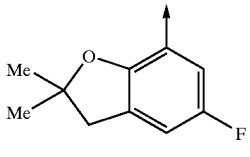 | 2 | Me | Found 471 (MH⁺). $C_{26}H_{31}FN_2O_5$ requires 470. |
| E43 | 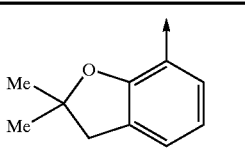 | 2 | H | Found 457 (MH⁺). $C_{25}H_{29}FN_2O_5$ requires 456. |
| E138 | 4-benzofuranyl | 2 | H | Found 409 (MH⁺). $C_{23}H_{24}N_2O_5$ requires 408. |
| E139 | 4-benzofuranyl | 2 | Me | Found 423 (MH⁺). $C_{24}H_{26}N_2O_5$ requires 422. |
| E140 | 1-isoquinolinyl | 2 | Me | Found 434 (MH⁺). $C_{25}H_{27}N_3O_4$ requires 433. |
| E141 | 5-(8-chloro-2-methyl)quinolinyloxy | 2 | Me | Found 482 (MH⁺). $C_{26}H_{28}{}^{35}ClN_3O_4$ requires 481. |

TABLE 2

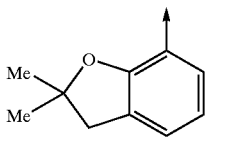

| Example | Ar | m | R¹ | Mass spectrum (API⁺) |
|---|---|---|---|---|
| E44 |  | 2 | H | Found 437 (MH⁺). $C_{26}H_{32}N_2O_4$ requires 436. |
| E45 | 2-cyanophenyl | 2 | H | Found 392 (MH⁺). $C_{23}H_{25}N_3O_3$ requires 391. |
| E46 | 2-(5-isoxazolyl)phenyl | 2 | H | Found 434 (MH⁺). $C_{25}H_{27}N_3O_3$ requires 433. |
| E47 | 2-cyanophenyl | 3 | H | Found 406 (MH⁺). $C_{24}H_{27}N_3O_3$ requires 405. |
| E48 | 4-indolyl | 2 | H | Found 406 (MH⁺). $C_{24}H_{27}N_3O_3$ requires 405. |
| E49 |  | 3 | H | Found 451 (MH⁺). $C_{27}H_{34}N_2O_4$ requires 450. |

TABLE 2-continued

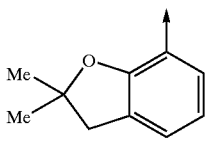

| Example | Ar | m | R¹ | Mass spectrum (API⁺) |
|---|---|---|---|---|
| E50 | 2-(5-isoxazolyl)phenyl | 3 | Me | Found 462 (MH⁺). $C_{27}H_{31}N_3O_4$ requires 461. |
| E51 | 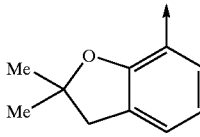 | 2 | Me | Found 451 (MH⁺). $C_{27}H_{34}N_2O_4$ requires 450. |
| E52 | 4-indolyl | 2 | Me | Found 420 (MH⁺). $C_{25}H_{29}N_3O_3$ requires 419. |
| E53 | 1-naphthyl | 2 | H | Found 417 (MH⁺). $C_{26}H_{28}N_2O_3$ requires 416. |
| E54 | 2-isopropoxyphenyl | 2 | H | Found 425 (MH⁺). $C_{25}H_{32}N_2O_4$ requires 424. |
| E55 | 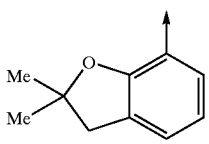 | 2 | H | Found 455 (MH⁺). $C_{26}H_{31}FN_2O_4$ requires 454. |
| E56 | 5-quinolinyl | 3 | H | Found 432 (MH⁺). $C_{26}H_{29}N_3O_3$ requires 431. |
| E57 | 4-benzo[b]furanyl | 2 | H | Found 407 (MH⁺). $C_{24}H_{26}N_2O_4$ requires 406. |
| E142 | 1-isoquinolinyl | 2 | H | Found 418 (MH⁺). $C_{25}H_{27}N_3O_3$ requires 417. |
| E143 | 5-(2-methyl)quinoxalinyl | 3 | H | Found 447 (MH⁺). $C_{26}H_{30}N_4O_3$ requires 446. |

TABLE 3

| Example | Ar | m | Mass spectrum (API⁺) |
|---|---|---|---|
| E58 | 4-indolyl | 2 | Found 420 (MH⁺). $C_{24}H_{25}N_3O_4$ requires 419. |
| E59 | 2-(5-isoxazolyl)phenyl | 3 | Found 462 (MH⁺). $C_{26}H_{27}N_3O_5$ requires 461. |
| E60 | | 2 | Found 451 (MH⁺). $C_{26}H_{30}N_2O_5$ requires 450. |

TABLE 4

ArO(CH₂)ₘN(pyrrolidinyl-(CH₂)q)-CH₂-O-(benzoxazin-3-one)

| Example | Ar | m | q | Mass spectrum (API⁺) |
|---|---|---|---|---|
| E61 | 2-(5-isoxazolyl)phenyl | 3 | 2 | Found 464 (MH⁺). $C_{26}H_{29}N_3O_5$ requires 463. |
| E62 | 4-indolyl | 2 | 2 | Found 422 (MH⁺). $C_{24}H_{27}N_3O_4$ requires 421. |
| E63 | 2,2-dimethyl-2,3-dihydrobenzofuran-7-yl | 2 | 2 | Found 453 (MH⁺). $C_{26}H_{32}N_2O_5$ requires 452. |
| E64 | 4-indolyl | 2 | 1 | Found 408 (MH⁺). $C_{23}H_{25}N_3O_4$ requires 407. |
| E65 | 2-(5-isoxazolyl)phenyl | 3 | 1 | Found 450 (MH⁺). $C_{25}H_{27}N_3O_5$ requires 449. |
| E66 | 2,2-dimethyl-2,3-dihydrobenzofuran-7-yl | 2 | 1 | Found 439 (MH⁺). $C_{25}H_{30}N_2O_5$ requires 438. |
| E67 | 2,2-dimethyl-2,3-dihydrobenzofuran-7-yl | 3 | 1 | Found 453 (MH⁺). $C_{26}H_{32}N_2O_5$ requires 452. |
| E68 | 1-naphthyl | 2 | 1 | Found 419 (MH⁺). $C_{25}H_{26}N_2O_4$ requires 418. |
| E69 | 2-isopropoxyphenyl | 2 | 2 | Found 441 (MH⁺). $C_{25}H_{32}N_2O_5$ requires 440. |
| E70 | 2-isopropoxyphenyl | 2 | 1 | Found 427 (MH⁺). $C_{24}H_{30}N_2O_5$ requires 426. |
| E71 | 5-quinolinyl | 2 | 2 | Found 434 (MH⁺). $C_{25}H_{27}N_3O_4$ requires 433. |
| E72 | 5-quinolinyl | 2 | 1 | Found 420 (MH⁺). $C_{24}H_{25}N_3O_4$ requires 419. |
| E73 | 2-cyano-4-fluorophenyl | 3 | 1 | Found 426 (MH⁺). $C_{23}H_{24}FN_3O_4$ requires 425. |
| E74 | 2-cyano-4-fluorophenyl | 3 | 2 | Found 440 (MH⁺). $C_{24}H_{26}FN_3O_4$ requires 439. |
| E75 | 2,2-dimethyl-5-fluoro-2,3-dihydrobenzofuran-7-yl | 2 | 2 | Found 471 (MH⁺). $C_{26}H_{31}FN_2O_5$ requires 470. |
| E76 | 2,2-dimethyl-5-fluoro-2,3-dihydrobenzofuran-7-yl | 2 | 1 | Found 457 (MH⁺). $C_{25}H_{29}FN_2O_5$ requires 456. |
| E77 | 8-quinolinyl | 2 | 1 | Found 420 (MH⁺). $C_{24}H_{25}N_3O_4$ requires 419. |
| E78 | 8-quinolinyl | 2 | 2 | Found 434 (MH⁺). $C_{25}H_{27}N_3O_4$ requires 433. |

TABLE 5

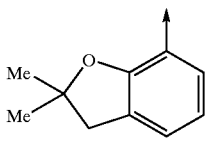

| Example | Ar | m | n | q | Y | Mass spectrum (API+) |
|---|---|---|---|---|---|---|
| E79 | 2-cyanophenyl | 3 | 1 | 1 | O | Found 394 (MH+). $C_{22}H_{23}N_3O_4$ requires 393. |
| E80 | 2-(5-isoxazolyl)phenyl | 3 | 1 | 1 | O | Found 436 (MH+). $C_{24}H_{25}N_3O_5$ requires 435. |
| E81 | 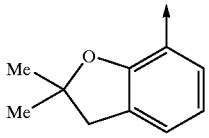 | 2 | 1 | 1 | O | Found 425 (MH+). $C_{24}H_{28}N_2O_5$ requires 424. |
| E82 | 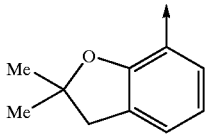 | 3 | 1 | 1 | O | Found 439 (MH+). requires 438. |
| E83 | 1-naphthyl | 2 | 1 | 1 | O | Found 405 (MH+). $C_{24}H_{24}N_2O_4$ requires 404. |
| E84 | 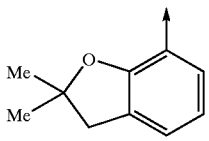 | 2 | 1 | 2 | O | Found 439 (MH+). $C_{25}H_{30}N_2O_5$ requires 438. |
| E85 | 1-naphthyl | 2 | 1 | 2 | bond | Found 403 (MH+). $C_{25}H_{26}N_2O_3$ requires 402. |
| E86 | 2-cyanophenyl | 3 | 1 | 2 | bond | Found 392 (MH+). $C_{23}H_{25}N_3O_3$ requires 391. |
| E87 | 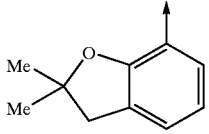 | 2 | 1 | 2 | bond | Found 423 (MH+). $C_{25}H_{30}N_2O_4$ requires 422. |
| E88 | 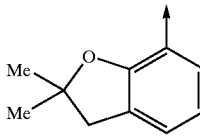 | 3 | 1 | 2 | bond | Found 437 (MH+). $C_{26}H_{32}N_2O_4$ requires 436. |
| E89 | (Me,Me-benzofuran with F) | 2 | 1 | 1 | O | Found 443 (MH+). $C_{24}H_{27}FN_2O_5$ requires 442. |
| E90 | 4-indolyl | 3 | 2 | 1 | bond | Found 406 (MH+). $C_{24}H_{27}N_3O_3$ requires 405. |
| E91 | 2-cyanophenyl | 3 | 2 | 1 | bond | Found 392 (MH+). $C_{23}H_{25}N_3O_3$ requires 391. |
| E92 | 2-(5-isoxazolyl)phenyl | 3 | 2 | 1 | bond | Found 434 (MH+). $C_{25}H_{27}N_3O_4$ requires 433. |

TABLE 5-continued

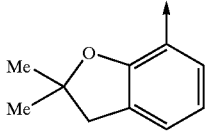

| Example | Ar | m | n | q | Y | Mass spectrum (API+) |
|---|---|---|---|---|---|---|
| E93 | (2,2-dimethyl-2,3-dihydrobenzofuran-7-yl) | 3 | 2 | 1 | bond | Found 437 (MH+). $C_{26}H_{32}N_2O_4$ requires 436. |
| E94 | 5-quinolinyl | 2 | 1 | 2 | bond | Found 404 (MH+). $C_{24}H_{25}N_3O_3$ requires 403. |

TABLE 6

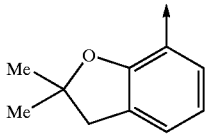

| Example | Ar | m | p | Mass spectrum (API+) |
|---|---|---|---|---|
| E95 | 4-indolyl | 2 | 1 | Found 407 (MH+). $C_{23}H_{26}N_4O_3$ requires 406. |
| E96 | 1-naphthyl | 2 | 1 | Found 418 (MH+). $C_{25}H_{27}N_3O_3$ requires 417. |
| E97 | 2-cyanophenyl | 3 | 1 | Found 407 (MH+). $C_{23}H_{26}N_4O_3$ requires 406. |
| E98 | (2,2-dimethyl-2,3-dihydrobenzofuran-7-yl) | 2 | 1 | Found 438 (MH+). $C_{25}H_{31}N_3O_4$ requires 437. |
| E99 | 4-indolyl | 3 | 0 | Found 407 (MH+). $C_{23}H_{26}N_4O_3$ requires 406. |
| E100 | 2-cyanophenyl | 3 | 0 | Found 393 (MH+). $C_{22}H_{24}N_4O_3$ requires 393. |
| E101 | 2-(5-isoxazolyl)phenyl | 3 | 0 | Found 435 (MH+). $C_{24}H_{26}N_4O_4$ requires 434. |
| E102 | (2,2-dimethyl-2,3-dihydrobenzofuran-7-yl) | 3 | 0 | Found 438 (MH+). $C_{25}H_{31}FN_3O_4$ requires 437. |
| E103 | (5-oxo-5,6,7,8-tetrahydronaphthalen-1-yl) | 2 | 1 | Found 456 (MH+). $C_{25}H_{30}FN_3O_4$ requires 455. |
| E104 | 5-quinolinyl | 2 | 1 | Found 419 (MH+). $C_{24}H_{26}N_4O_3$ requires 418. |
| E105 | 2-cyanophenyl | 4 | 0 | Found 407 (MH+). $C_{23}H_{26}N_4O_3$ requires 406. |
| E106 | 2-(5-isoxazolyl)phenyl | 4 | 0 | Found 449 (MH+). $C_{25}H_{28}N_4O_4$ requires 448. |
| E107 | 5-quinolinyl | 3 | 0 | Found 419 (MH+). |

TABLE 6-continued

ArO(CH₂)ₘN(piperazine)(CH₂)ₚ-benzoxazinone structure

| Example | Ar | m | p | Mass spectrum (API⁺) |
|---|---|---|---|---|
| E144 | 4-benzofuranyl | 2 | 1 | $C_{24}H_{26}N_4O_3$ requires 418. Found 408 (MH⁺). |
| E145 | 1-isoquinolinyl | 2 | 1 | $C_{23}H_{25}N_3O_4$ requires 407. Found 419 (MH⁺). |
| E146 | 2-(5-(3-methyl)isoxazolyl)phenyl | 3 | 1 | $C_{24}H_{26}N_4O_3$ requires 418. Found 463 (MH⁺). $C_{26}H_{30}N_4O_4$ requires 462. |

EXAMPLE 108

6-(4-(1-(2-(5-(2-methyl)quinolinyloxy)ethyl)piperidinyl)methyl)-4H-benzo[1,4]oxazin-3-one (E108)

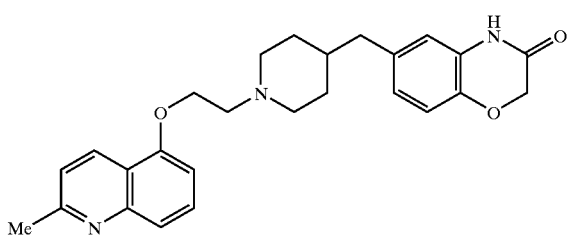

A mixture of 6-(4-piperidinylmethyl)-4H-benzo[1,4]oxazin-3-one hydrochloride (0.10 g 0.35 mmol). 2-(5-(2-methyl)quinolinyloxy)ethyl bromide (0.11 g, 0.42 mmol), diisopropylethylamine (1 mL) and isopropanol (10 mL) was heated at reflux under argon for 48 h. cooled, then evaporated in vacuo. The residue was partitioned between saturated aqueous NaHCO₃ (50 mL) and dichloromethane (3×30 mL) and the combined organic extracts were dried (Na₂SO₄) and evaporated in vacuo. The resulting oil was purified by chromatography on silica eluting with 50% ethyl acetate-hexane followed by 0–25% methanol-ethyl acetate gradient elution, to give the title compound (0.04 g, 26%) as an oil.

Mass spectrum (API⁺): Found 432 (MH⁺). $C_{26}H_{29}N_3O_3$ requires 431.

¹H NMR (CDCl₃) δ: 1.25–1.38 (2H, m), 1.49 (1H, m), 1.65 (2H, m), 2.14 (2H, m), 2.45 (2H, d, J=7 Hz), 2.72 (3H, s), 2.94 (2H, t, J=6 Hz), 3.05 (2H, m), 4.27 (2H, t, J=6 Hz), 4.58 (2H, s), 6.56 (1H, d, J=2 Hz), 6.73 (1H, dd, J=7, 2 Hz), 6.78 (1H, d, J=8 Hz), 7.86 (1H, d, J=7 Hz), 7.23 (1H, d, J=8 Hz), 7.50–7.64 (2H, m), 8.42 (1H, d, J=8 Hz), 8.75 (1H, br s).

EXAMPLE 108a 6-(4-(1-(2-(5-(2-Methyl)quinolinyloxy)ethyl)piperidinyl)methyl)-4H-benzo[1,4]oxazin-3-one dihydrochloride (E108a)

A mixture of 6-(4-piperidinylmethyl)-4H-benzo[1,4]oxazin-3-one hydrochloride (9.0 g 29.5 mmol). 2-(5-(2-methyl)quinolinyloxy)ethyl bromide (9.29 g, 34.9 mmol), diisopropylethylamine (93 mL) and isopropanol (250 mL) was heated at reflux under argon for 48 h. cooled, then evaporated in vacuo. The residue was partitioned between 5% aqueous NaOH (300 mL) and dichloromethane (3×150 mL) and tile combined organic extracts were dried (Na₂SO₄) and evaporated in vacuo. The resulting oil was purified by chromatography on silica with 0–20% methanol/ethyl acetate gradient elution to give the free base of the title compound (10.8 g 85%) as a colourless solid. This material was dissolved in 2-propanol at reflux, then 35% hydrochloric acid (5.36 mL) was added dropwise over 0.1 h. The mixture was stirred for 3 h and simultaneously allowed to cool to 20° C. whereupon the resulting solid was collected by filtration and dried in vacuo at 80–90° C. to give the title compound (11.71 g, 95%) as a pale yellow solid.

HPLC purity 98.6%

Mass spectrum (API⁺): Found 432 (MH⁺). $C_{26}H_{29}N_3O_3$ requires 431.

EXAMPLE 109

6-(4-(1-(2-(5-(3-Methyl)quinolinyloxy)ethyl)piperidinyl)methyl)-4H-benzo[1,4]oxazin-3-one (E109)

The title compound was prepared in a similar manner to Example 3.

Mass spectrum (API⁺): Found 432 (MH⁺). $C_{26}H_{29}N_3O_3$ requires 431.

¹H NMR (CDCl₃) δ: 1.34 (2H, m), 1.52 (1H, m), 1.65 (2H, m), 2.15 (2H, m), 2.47 (2H, d, J=7 Hz), 2.61 (3H, s), 2.94 (2H, t, J=6 Hz), 3.05 (2H, m), 4.26 (2H, t, J=6 Hz), 4.56 (2H, s), 6.56 (1H, d, J=1 Hz), 6.75 (1H, dd, J=8, 1 Hz), 6.83 (1H, d, J=8 Hz), 6.85 (1H, d, J=8 Hz), 7.50 (1H, t, J=8 Hz), 7.65 (1H, d, J=8 Hz), 8.29 (1H, d, J=2 Hz), 8.85 (1H, d, J=2 Hz), 8.99 (1H, br s).

EXAMPLE 110

6-(4-(1-(2-(5-Cinnolinyloxy)ethyl)piperidinyl)methyl)-4H-benzo[1,4]oxazin-3-one (E110)

The title compound was prepared in a similar manner to Example 3.

Mass spectrum (API⁺): Found 419 (MH⁺). $C_{24}H_{26}N_4O_3$ requires 418.

¹H NMR (CDCl₃) δ: 1.31 (2H, m), 1.52 (1H, m), 1.67 (2H, m), 2.17 (2H, m), 2.46 (2H, d, J=7 Hz), 2.95 (2H, d, J=6 H₂), 3.05 (24H, m), 4.31 (2H, t, J=6 Hz), 4.58 (2H, s), 6.57 (1H, s), 6.74 (1H, d, J=8 Hz), 6.86 (1H, d, J=8 Hz), 6.99 (1H, d, J=8 Hz), 7.74 (1H, t, J=8 Hz), 8.11 (1H, d, J=8 Hz), 8.17 (1H, d, J=6 Hz), 8.42 (1H, br s), 9.29 (1H, d, J=6 Hz).

EXAMPLE 111

6-(4-(1-(2-(4-(1,2-Dihydro)benzo[b]furanyloxy)ethyl)piperidinyl)methyl)-4H-benzo[1,4]oxazin-3-one (E111)

The title compound was prepared in a similar manner to Example 3.

Mass spectrum (API$^+$): Found 409 (MH$^+$). $C_{24}H_{28}N_2O_4$ requires 408.

$^1$H NMR (CDCl$_3$) δ: 1.33 (2H, m), 1.49 (1H, m), 1.65 (2H, m), 2.09 (2H, m), 2.46 (2H, d, J=7 Hz), 2.78 (1H, m), 3.00 (2H, m), 3.12 (2H, t, J=9 Hz), 4.13 (2H, m), 4.56 (4H, m), 6.37 (1H, d, J=8 Hz), 6.45 (1H, d, J=8 Hz), 6.56 (1H, s), 6.74 (1H, d, J=8 Hz), 6.87 (1H, d, J=5 Hz), 7.03 (1H, t, J=8 Hz), 8.14 (1H, br s).

EXAMPLE 112

6-(4-(1-(2-(4-(1H)-Indazolyloxy)ethyl)piperidinyl)methyl)-4H-benzo[1,4]oxazin-3-one (E112)

The title compound was prepared in a similar manner to Example 3.

Mass spectrum (API$^+$): Found 407 (MH$^+$). $C_{23}H_{26}N_4O_3$ requires 406.

$^1$H NMR (CDCl$_3$) δ: 1.32 (1H, m), 1.48 (1H, m), 1.63 (2H, m), 2.13 (1H, m), 2.45 (2H, m), 2.93 (2H, m), 3.06 (2H, m), 4.29 (2H, m), 4.58 (2H, s), 6.47 (1H, d, J=8 Hz), 6.55 (1H, d, J=2 Hz), 6.73 (1H dd, J=8, 2 Hz), 6.87 (1H, d, J=8 Hz), 7.06 (1H, d, J=8 Hz), 7.27 (2H, m), 8.10 (1H, m), 8.49 (1H, m).

EXAMPLE 113

6-(4-(1-(2-(5-(2-Methyl)quiniolinyloxy)ethyl)piperidinyl)oxy)-4H-benzo[1,4]oxazin-3-one (E113)

The title compound was prepared in a similar manner to Example 3

Mass spectrum (API$^+$): Found 434 (MH$^+$). $C_{25}H_{27}N_3O_4$ requires 433.

$^1$H NMR (CDCl$_3$) δ: 1.85 (2H, m), 1.99 (2H, m), 2.54 (2H, m), 2.74 (3H, s), 2.90 (2H, m), 2.96 (2H, m), 4.23 (1H, m), 4.30 (2H, m), 4.56 (2H, s), 6.37 (1H, d, J=2 Hz), 6.52 (1H, dd, J=9 Hz), 6.79 (1H, d, J=8 Hz), 6.87 (1H, d, J=9 Hz), 7.25 (1H, m), 7.56 (2H, m), 8.22 (1H, br s), 8.45 (1H, d, J=8 Hz).

EXAMPLE 114

4-Methyl-6-(4-(1-(2-(5-(2-methyl)quinolinyloxy)ethyl)piperidinyl)oxy)-4H-benzo[1,3]oxazin-3-one (E114)

The title compound was prepared in a similar manner to Example 3.

Mass spectrum (API$^+$): Found 448 (MH$^+$). $C_{26}H_{29}N_3O_4$ requires 447.

$^1$H NMR (CDCl$_3$) δ: 1.86 (1H, m), 2.01 (2H, m), 2.55 (2H, m), 2.75 (3H, s), 2.93 (2H, m), 3.00 (2H, m), 3.33 (3H, s), 4.20–4.34 (3H, m), 4.56 (2H, s), 6.55 (2H, m), 6.82 (1H, d, J=7 Hz), 6.89 (1H, d, J=7 Hz), 7.26 (1H, d, J=7 Hz), 7.59 (2H, m), 8.45 (1H, d, J=8 Hz).

EXAMPLE 115

6-(4-(1-(2-(5-(2-Methyl)quinolinyloxy)ethyl)piperazinyl)methyl)-4H-benzo[1,4]oxazin-3-one (E115)

The title compound was prepared in a similar manner to Example 3.

Mass spectrum (API$^+$): Found 433 (MH$^+$). $C_{25}H_{28}N_4O_3$ requires 432.

$^1$H NMR (CDCl$_3$) δ: 2.50 (4H, m), 2.69 (4H, m), 2.73 (3H, m), 2.97 (2H, t, J=6 Hz), 3.54 (2H, s), 4.30 (2H, t, J=6 Hz), 4.61 (2H, s), 6.79 (2H, m), 6.92 (1H, s), 7.24 (1H, d, J=8 Hz), 7.59 (2H, m), 7.87 (1H, br s), 8.43 (1H, d, J=8 Hz).

EXAMPLE 116

6-(4-(1-(3-(5-(2-methyl)quinolinyloxy)propyl)piperidinyl)methyl)4-H-benzo[1,4]oxazin-3-one (E116)

The title compound was prepared in a similar manner to Example 3.

Mass spectrum (API$^+$): Found 446 (MH$^+$). $C_{27}H_{31}N_3O_3$ requires 445.

$^1$H NMR (CDCl$_3$) δ: 1.40–1.60 (3H, m), 1.69 (2H, m) 2.14 (2H, m), 2.22 (2H, m), 2.50 (2H, d, J=6 Hz), 2.73 (5H, m), 3.14 (22H, m), 4.19 (2H, m), 4.60 (2H, s), 6.59 (1H, s), 6.75 (1H, d, J=8 Hz), 6.79 (1H, d, J=8 Hz), 6.89 (1H, d, J=8 Hz), 7.24 (1H, d, J=8 Hz), 7.56 (2H, m), 8.39 (1H, br s), 8.43 (1H, d, J=8 Hz).

EXAMPLE 117

6-(4-(1-(3-(5-(2-methyl)quinolinyloxy)propyl)piperazinyl)methyl)-4H-benzo[1,4]oxazin-3-one (E117)

The title compound was prepared in a similar manner to Example 3.

Mass spectrum (API$^+$): Found 447 (MH$^+$). $C_{26}H_{30}N_4O_3$ requires 446.

$^1$H NMR (CDCl$_3$) δ: 2.09 (2H, m), 2.50 (8H, m), 2.61 (2H, m), 2.73 (3H, s), 3.42 (2H, s), 4.18 (2H, m), 4.60 (2H, s), 6.80 (2H, m), 6.90 (2H, m), 7.24 (1H, d, J=9 Hz), 7.55 (2H, m), 8.32 (1H, br s), 8.44 (1H, d, J=9 Hz).

EXAMPLE 118

6-(4-(1-(3-(5-(2-Methyl)quinolinyloxy)propyl)piperidinyl)oxy)-4H-benzo[1,4]oxazin-3-one (E118)

The title compound was prepared in a similar manner to Example 3.

Mass spectrum (API$^+$): Found 448 (MH$^+$). $C_{26}H_{29}N_3O_4$ requires 447.

$^1$H NMR (CDCl$_3$) δ: 1.81 (2H, m), 1.97 (2H, m), 2.11 (2H, m), 2.34 (2H, m), 2.63 (2H, m), 0.73 (3H, s), 2.76 (2H, m), 4.20 (3H, m), 4.56 (2H, s), 6.41 (1H, d, J=3 Hz), 6.53 (1H, dd, J=9, 3 Hz), 6.81 (1H, dd, J=7.2 Hz), 6.88 (1H, d, J=9 Hz), 7.24 (1H, m), 7.56 (2H, m), 8.46 (1H, d, J=9 Hz), 8.55 (1H, br s).

EXAMPLE 119

4-Methyl-6-(4-(1-(3-(5-(2-methyl)quinolinyloxy)propyl)piperidinyl)oxy)-4H-benzo[1,4]oxazin-3-one (E119)

The title compound was prepared in a similar manner to Example 3.

Mass spectrum (API$^+$): Found 462 (MH$^+$). $C_{27}H_{31}N_3O_4$ requires 461.

$^1$H NMR (CDCl$_3$) δ: 1.83 (2H, m), 1.99 (2H, m), 2.12 (2H, m), 2.35 (2H, m), 2.63 (2H, m), 2.73 (3H, s), 2.80 (2H, m), 3.33 (3H, s), 4.21 (2H, m), 4.25 (1H, m), 4.56 (2H, s), 6.54 (2H, m), 6.81 (1H, dd, J=7.2 Hz), 6.88 (1H, d, J=9 Hz), 7.24 (1H, m), 7.55 (2H, m), 8.46 (1H, d, J=9 Hz).

EXAMPLE 120

4-Methyl-6-(4-(1-(2-(5-(2-methyl)quinolinyloxy)
ethyl)piperidinyl)methyl)-4H-benzo[1,4]oxazin-
3-one (E120)

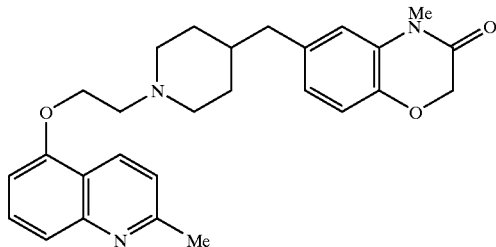

A solution of 2-(5-(2-methyl)quinolinyl)oxyethyl bromide (0.15 g 0.62 mmol), 4-methyl-6-(4-piperidinylmethyl)-4H-benzo[1,4]oxazin-3-one hydrochloride (0.19 g, 0.62 mmol) and diisopropylethylamine (0.6 mL, 3.4 mmol) in isopropyl alcohol (8 mL) was stirred at 78° C. for 48 h. The mixture was concentrated in vacuo to approximately 1 mL and applied to silica gel column. Gradient elution with methanol (0–10%) in ethyl acetate gave the title compound (0.15 g, 52%) as a colourless oil.

Mass spectrum (API$^+$): Found 446 (MH$^+$). $C_{27}H_{31}N_3O_3$ requires 445.

$^1$H NMR (CDCl$_3$) δ: 1.40 (2H, m), 1.55 (1H, m), 1.70 (2H, m), 2.10 (2H, m), 2.62 (2H, d, J=7 Hz), 2.74 (3H, s), 3.13 (4H, m), 3.34 (3H, s), 4.57 (2H, s), 4.70 (2H, m), 6.71–6.78 (2H, m), 6.86 (1H, d, J=6.5 Hz), 6.91 (1H, d, J=8 Hz), 7.26 (1H, d, J=8 Hz), 7.58 (1H, t, J=8 Hz), 7.67 (1H, d, J=8 Hz), 8.33 (1H, d, J=8 Hz).

EXAMPLE 121

6-(4-(1-(2-(5-(8-Chloro-2-methyl)quinolinyloxy)
ethyl)piperidinyl)methyl)-4H-benzo[1,4]oxazin-
3-one (E121)

A solution of 2-(5-(8-chloro-2-methyl)quinolinyl) oxyethyl bromide (0.10 g, 0.33 mmol), 6-(4-piperidinylmethyl)-4H-benzo[1,4]oxazin-3-one hydrochloride (0.093 g, 0.33 mmol) and diisopropylethylamine (0.25 mL, 1.43 mmol) in isopropyl alcohol (10 mL) was stirred at reflux for 48 h. The reaction mixture was cooled and evaporated in vacuo. The residue was partitioned between dichloromethane (5 mL) and water (5 mL), and the organic layer was added onto a pre-packed silica column (10 g) which was then eluted with 0–20% methanol in ethyl acetate. The fractions containing the title compound were combined and evaporated to dryness in vacuo to give the title compound (0.035 g, 23%) as an oil.

Mass spectrum (API$^+$): Found 466 (MH$^+$). $C_{26}H_{28}^{35}ClN_3O_3$ requires 465.

$^1$H NMR (CDCl$_3$) δ: 1.32 (2H, m), 1.48 (1H, m), 1.66 (2H, m), 2.12 (2H, m), 2.46 (2H, m), 2.80 (3H, s), 2.92 (2H, m), 3.03 (2H, m), 4.25 (2H, m), 4.58 (2H, s), 6.55 (1H, d, J=2 Hz), 6.72 (2H, m), 6.87 (1H, d, J=8 Hz), 7.30 (1H, d, J=9 Hz), 7.65 (1H, d, J=8 Hz), 8.35 (1H, br s), 8.43 (1H, d, J=9 Hz).

EXAMPLE 122

4-Methyl-6-(4-(1-(3-(5-(2-methyl)quinolinyloxy)
propyl)piperidinyl)-methyl)-4H-benzo[1,4]oxazin-
3-one (E122)

The title compound was prepared in a similar manner to Example 3.

Mass spectrum (API$^+$): Found 460 (MH$^+$). $C_{28}H_{33}N_3O_3$ requires 459

$^1$H NMR (CDCl$_3$) δ: 1.34 (2H, m), 1.52 (1H, m), 1.63 (2H, m), 1.94 (2H, m), 2.09 (2H, m), 2.52 (2H, d, J=13 Hz), 2.58 (2H, m), 2.73 (3H, s), 2.97 (2H, m), 3.36 (3H, s), 4.18 (2H, m), 4.59 (2H, s), 6.70–8.86 (3H, m), 6.89 (1H, d, J=8 Hz), 7.24 (1H, d, J=8 Hz), 7.50–7.60 (2H, m), 8.43 (1H, d, J=8 Hz).

EXAMPLE 123

6-(4-(1-(2-(5-(8-Chloro-2-methyl)quinolinyloxy)
ethyl)piperidinyl)methyl)-4-methyl-4H-benzo[1,4]
oxazin-3-one (E122)

The title compound was prepared in a similar manner to Example 3.

Mass spectrum (API$^+$): Found 480 (MH$^+$), $C_{27}H_{30}^{35}ClN_3O_3$ requires 479.

$^1$H NMR (CDCl$_3$) δ: 1.35 (2H, m), 1.51 (1H, m), 1.66 (2H, m), 2.13 (2H, m), 2.52 (2H, m), 2.80 (3H, s), 2.92 (2H, m), 3.03 (2H, m), 3.35 (3H, s), 4.25 (2H, m), 4.59 (2H, s), 6.75 (3H, m), 6.89 (1H, d, J=8 Hz), 7.31 (1H, d, J=9 Hz), 7.66 (1H, d, J=8 Hz), 8.44 (1H, d, J=9 Hz).

EXAMPLE 124

6-(4-(1-(2-(5-(8-Fluoro-2-methyl)quinolinyloxy)
ethyl)piperidinyl)methyl)-4H-benzo[1,4]oxazin-
3-one (E124)

A mixture of 6-(4-piperidinylmethyl)-4H-benzo[1,4] oxazin-3-one hydrochloride (1.2 g. 3.93 mmol). 2-(5-(8-fluoro-2-methyl)quinolinyloxy)ethyl bromide (1.32 g, 4.65 mmol), diisopropylethylamine (12.4 mL) and isopropanol (50 mL) was heated at reflux under argon for 36 h cooled, then evaporated in vacuo. The residue was partitioned between water (100 mL) 50% aqueous sodium hydroxide (20 mL) and dichloromethane (3×50 mL). The combined organic extracts were dried (Na$_2$SO$_4$) and evaporated in vacuo to give a solid (2.2 g). Chromatography on silica with 0–20% methanol/ethyl acetate gradient elution gave the title compound (1.38 g, 68%) as a colourless solid.

Mass spectrum (API$^+$): Found 450 (MH$^+$). $C_{26}H_{28}FN_3O_3$ requires 449.

$^1$H NMR (CDCl$_3$) δ: 1.29 (2H, m), 1.50 (1H, m), 1.65 (2H, m), 2.15 (2H, m), 2.45 (2H, d, J=6 Hz), 2.79 (3H, s), 2.92 (2H, m), 3.04 (2H, m), 4.24 (2H, m), 4.58 (2H, s), 6.55 (1H, s), 6.66 (1H, m), 6.75 (1H, d, J=9 Hz), 6.87 (1H, d, J=9 Hz), 7.21–7.34 (2H, m), 8.35 (1H, br s), 8.42 (1H, d, J=8 Hz).

EXAMPLE 125

6-(4-(1-(2-(5-(8-Fluoro-2-methyl)quinolinyloxy)
ethyl)piperidinyl)methyl)-4-methyl-4H-benzo[1,4]
oxazin-3-one (E125)

The title compound was prepared in a similar manner to Example 3.

Mass spectrum (API$^+$): Found 464 (MH$^+$). $C_{27}H_{30}FN_3O_3$ requires 463.

$^1$H NMR (CDCl$_3$) δ: 1.35 (2H, m), 1.54 (1H, m), 1.67 (2H, m), 2.15 (2H, m), 2.53 (2H, d, J=6 Hz), 2.79 (3H, s), 2.92 (2H, m), 3.05 (2H, m), 3.35 (3H, s), 4.24 (2H, m), 4.58 (2H, s), 6.67 (1H, m), 6.73 (1H, s), 6.77 (1H, d, J=8 Hz), 6.87 (1H, d, J=8 Hz), 7.20–7.34 (2H, m), 8.42 (1H, d, J=8 Hz).

EXAMPLE 126

6-(4-(1-(2-(5-(8-Fluoro-2-methyl)quinolinyloxy)ethyl)piperidinyl)oxy)-4H-benzo[1,4]oxazin-3-one (E126)

The title compound was prepared in a similar manner to Example 3.

Mass spectrum (API$^+$): Found 452 (MH$^+$). $C_{25}H_{26}FN_3O_4$ requires 451.

$^1$H NMR (CDCl$_3$) δ: 1.81 (2H, m), 1.97 (2H, m), 2.52 (2H, m), 2.80 (3H, s), 2.89 (2H, m), 2.96 (2H, t, J=6 Hz), 4.25 (3H, m), 4.56 (2H, s), 6.43 (1H, d, J=2 Hz), 6.53 (1H, dd, J=9, 2 Hz), 6.71 (1H, dd, J=9.3 Hz), 6.88 (1H, d, J=9 Hz), 7.22–7.35 (2H, m), 8.45 (1H, d, J=9 Hz), 8.47 (1H, br s).

EXAMPLE 127

6-(4-(1-(2-(5-(8-Fluoro-2-methyl)quinolinyloxy)ethyl)piperidinyl)oxy)-4-methyl-4H-benzo[1,4]oxazin-3-one (E127)

The title compound was prepared in a similar manner to Example 3.

Mass spectrum (API$^+$): Found 466 (MH$^+$). $C_{26}H_{28}FN_3O_4$ requires 465.

$^1$H NMR (CDCl$_3$) δ: 1.86 (2H, m), 2.02 (2H, m), 2.52 (2H, m), 2.79 (3H, s), 2.93 (2H, m), 2.96 (2H, t, J=6 Hz), 3.35 (3H, s), 4.28 (3H, m), 4.56 (2H, s), 6.55 (2H, m), 6.70 (1H, dd, J=9.2 Hz), 6.90 (1H, d, J=9 Hz), 7.22–7.36 (2H, m), 8.45 (1H, d, J=8 Hz).

EXAMPLE 128

6-(4-(1-(2-(5-(7-Chloro-2-methyl)quinolinyloxy)ethyl)piperidinyl)methyl)-4H-benzo[1,4]oxazin-3-one (E128)

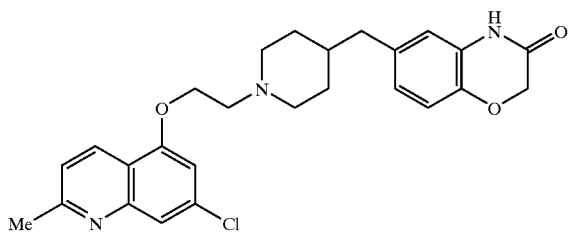

A solution of 2-(5-(7-chloro-2-methyl)quinolinyl)oxyethyl bromide (0.64 g, 2.13 mmol). 6-(4-piperidinylmethyl)-4H-benzo[1,4]oxazin-3-one hydrochloride (0.60 g, 2.13 mmol) and diisopropylamine (1.50 mL. 8.62 mmol) in isopropyl alcohol (60 mL) was stirred at reflux for 48 h. The reaction mixture was cooled and evaporated in vacuo. The residue was partitioned between dichloromethane (30 mL) and water (30 mL). The organic layer was dried over anhydrous sodium sulfate and evaporated in vacuo to give a brown oil which was purified by chromatography on silica gel (30 g) eluting with 0–15% methanol in ethyl acetate to give the title compound (0.46 g, 47%) as a brown solid.

Mass spectrum (API$^+$): Found 466 (MH$^+$). $C_{26}H_{28}{}^{35}ClN_3O_3$ requires 465.

$^1$H NMR (CDCl$_3$) δ: 1.33 (2H, m), 1.47 (1H, m), 1.63 (2H, m), 2.15 (2H, m), 2.46 (2H, d, J=7 Hz), 2.68 (3H, s), 2.87 (2H, t, J=6 Hz), 2.97 (2H, m), 4.24 (2H, t, J=6 Hz), 4.55 (2H, s), 6.50 (1H, d, J=2 Hz), 6.72 (1H, dd, J=8, 2 Hz), 6.78 (1H, d, J=2 Hz), 6.85 (1H, d, J=8 Hz), 7.17 (1H, d, J=9 Hz), 7.56 (2H, m), 8.32 (1H, d, J=9 Hz).

EXAMPLE 129

6-(4-(1-(2-(5-(7-Chloro-2-methyl)quinolinyloxy)ethyl)piperidinyl)methyl)-4-methyl-4H-benzo[1,4]oxazin-3-one (E129)

The title compound was prepared in a similar manner to Example 3.

Mass spectrum (API$^+$): Found 480 (MH$^+$). $C_{27}H_{30}{}^{35}ClN_3O_3$ requires 479.

$^1$H NMR (CDCl$_3$) δ: 1.35 (2H, m), 1.50 (1H, m), 1.67 (2H, m), 2.14 (2H, m), 2.52 (2H, m), 2.71 (3H, s), 2.92 (1H, m), 3.03 (2H, m), 3.35 (3H, s), 4.25 (2H, m), 4.59 (2H, s), 6.76 (3H, m), 6.89 (1H, d, J=8 Hz), 7.22 (1H, d, J=9 Hz), 7.60 (1H, d, J=1 Hz), 8.35 (1H, J=9 Hz).

EXAMPLE 130

6-(4-(1-(2-(5-(7-Chloro-2-methyl)quinolinloxy)ethyl)piperidinyl)oxy)-4H-benzo[1,4]oxazin-3-one (E130)

The title compound was prepared in a similar manner to Example 3.

Mass spectrum (API$^+$): Found 468 (MH$^+$). $C_{25}H_{26}{}^{35}ClN_3O_4$ requires 467.

$^1$H NMR (CDCl$_3$) δ: 1.81 (2H, m), 1.97 (2H, m), 2.51 (2H, m), 2.71 (3H, s), 2.88 (2H, m), 2.97 (H, m), 4.23 (3H, m), 4.56 (2H, s), 6.40 (1H, d, J=3 Hz), 6.53 (1H, dd, J=9, 3 Hz), 6.78 (1H, d, J=2 Hz), 6.88 (1H, d, J=9 Hz), 7.24 (1H, d, J=9 Hz), 7.60 (1H, m), 8.37 (1H, d, J=9 Hz), 8.50 (1H, br s).

EXAMPLE 131

6-(4-(1-(2-(5-(7-Chloro-2-methyl)quinolinyloxy)ethyl)piperidinyl)oxy)-4-methyl-4H-benzo[1,4]oxazin-3-one (E131)

The title compound was prepared in a similar manner to Example 3.

Mass spectrum (API$^+$): Found 482 (MH$^+$). $C_{26}H_{28}{}^{35}ClN_3O_4$ requires 481.

$^1$H NMR (CDCl$_3$) δ: 1.84 (2H, m), 2.02 (2H, m), 2.52 (2H, m), 2.72 (3H, s), 2.91 (2H, m), 2.98 (2H, m), 3.32 (3H, s), 4.27 (3H, m), 4.56 (2H, s), 6.54 (2H, m), 6.76 (1H, m), 6.89 (1H, d, J=8 Hz), 7.24 (1H, d, J=8 Hz), 7.60 (1H, m), 8.37 (1H, d, J=9 Hz).

EXAMPLE 132

6-(4-(1-(2-(5-(7-Chloro-2-methyl)quinolinyloxy)ethyl)piperazinyl)methyl)-4H-benzo[1,4]oxazin-3-one (E132)

The title compound was prepared in a similar manner to Example 3.

Mass spectrum (API$^+$): Found 467 (MH$^+$). $C_{25}H_{27}{}^{35}ClN_4O_3$ requires 466.

$^1$H NMR (CDCl$_3$) δ: 2.49 (4H, m), 2.67 (4H, m), 2.71 (3H, s), 2.93 (2H, m), 3.42 (2H, s), 4.26 (2H, m), 4.60 (2H, s), 6.78 (1H, m), 6.90 (2H, m), 7.22 (1H, d, J=9 Hz), 7.60 (1H, m), 8.20 (1H, br s), 8.35 (1H, d, J=9 Hz).

EXAMPLE 133

6-(4-(1-(3-(5-(7-Chloro-2-methyl)quinolinyloxy)propyl)piperidinyl)oxy)-4H-benzo[1,4]oxazin-3-one (E133)

The title compound was prepared in a similar manner to Example 3.

Mass spectrum (API$^+$): Found 482 (MH$^+$). $C_{26}H_{28}{}^{35}ClN_3O_4$ requires 481.

$^1$H NMR (CDCl$_3$) δ: 1.81 (2H, m), 1.97 (2H, m), 2.11 (2H, m), 2.34 (2H, m), 2.60 (2H, m), 2.72 (3H, s), 2.77 (2H, m), 4.22 (3H, m), 4.57 (2H, s), 6.41 (1H, d, J=3 Hz), 6.53 (1H, dd, J=9, 3 Hz), 6.79 (1H, d, J=2 Hz), 6.88 (1H, d, J=9 Hz), 7.24 (1H, d, J=9 Hz), 7.59 (1H, d, J=2 Hz), 8.38 (1H, d, J=9 Hz), 8.48 (1H, br s).

EXAMPLE 134

6-(4-(1-(3-(5-(7-Chloro-2-methyl)quinolinyloxy) propyl)piperidinyl)oxy)-4-methyl-4H-benzo[1,4] oxazine-3-one (E134)

The title compound was prepared in a similar manner to Example 3.

Mass spectrum (API$^+$): Found 496 (MH$^+$). C$_{27}$H$_{30}^{35}$ClN$_3$O$_4$ requires 495.

$^1$H NMR (CDCl$_3$) δ: 1.82 (2H, m), 1.98 (2H, m), 2.11 (2H, m), 2.34 (2H, m), 2.61 (2H, m), 2.71 (3H, s), 2.79 (2H, m), 3.33 (3H, s), 4.17 (2H, m), 4.26 (1H, m), 4.56 (2H, s), 6.54 (2H, m), 6.79 (1H, d, J=2 Hz), 6.88 (1H, d, J=8 Hz), 7.23 (1H, d, J=9 Hz), 7.59 (1H, d, J=2 Hz), 8.38 (1H, d, J=9 Hz).

EXAMPLE 135

6-(4-(1-(2-(5-(2-Methyl)quinolinyloxy)ethyl) piperidinyl)methyl)-4-(2-propyl)-4H-benzo[1,4] oxazin-3-one (E135)

The title compound was prepared in a similar manner to Example 3.

Mass spectrum (API$^+$): Found 474 (MH$^+$). C$_{29}$H$_{35}$N$_3$O$_3$ requires 473.

$^1$H NMR (CDCl$_3$) δ: 1.30 (2H, m), 1.49 (1H, m), 1.55 (6H, d, J=7 Hz), 1.67 (2H, m), 2.15 (2H, m), 2.52 (2H, m), 2.73 (3H, s), 2.94 (2H, m), 3.05 (2H, m), 4.28 (2H, m), 4.45 (2H, s), 4.69 (1H, m), 6.77 (2H, m), 6.89 (2H, m), 7.24 (1H, d, J=9 Hz), 7.56 (2H, m), 8.43 (1H, d, J=9 Hz).

EXAMPLE 136

6-(4-(1-(2-(5-(2-Methyl)quinazolinyloxy)ethyl) piperidinyl)methyl)-4H-benzo[1,4]-oxazin-3-one (E136)

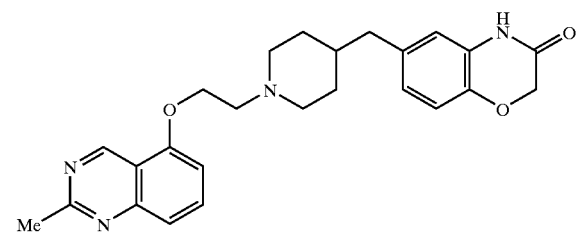

A mixture of 6-(4-piperidinylmethyl)-4H-benzo[1,4] oxazin-3-one hydrochloride (0.019 g, 0.067 mmol). 2-(5-(2-methyl)quinazolinyl)oxyethyl bromide (0.018 g, 0.067 mmol), diisopropylamine (0.3 mL) and isopropanol (5 mL) was heated at reflux for 64 h. cooled, then evaporated in vacuo. The residue was partitioned between 10% aqueous NaOH (2 mL) and dichloromethane (3×2 mL). The combined organic extracts were applied directly to a 5 g sep-pak silica cartridge. Gradient elution with 0–20% methanol in ethyl acetate gave the title compound (0.022 g, 76%) as an oil.

Mass spectrum (API$^+$): Found 433 (MH$^+$). C$_{25}$H$_{28}$N$_4$O$_3$ requires 432.

$^1$H NMR (CDCl$_3$) δ: 1.32 (2H, m), 1.50 (1H, m), 1.65 (2H, m), 2.18 (2H, m), 2.46 (2H, d, J=7 Hz), 2.90 (3H, s), 2.97 (2H, t, J=6 Hz), 3.04 (2H, m), 4.33 (2H, t, J=6 Hz), 4.59 (2H, s), 6.57 (1H, d, J=2 Hz), 6.74 (1H, dd, J=9.2 Hz), 6.86 (2H, m), 7.50 (1H, d, J=9 Hz), 7.75 (1H, t J=9 Hz), 8.49 (1H, br s), 9.64 (1H, s).

EXAMPLE 137

6-(4-(1-(2-(5-(7-Fluoro-2-methyl)quinolinyloxy) ethyl)piperidinyl)methyl)-4H-benzo[1,4]oxazin-3-one (E137)

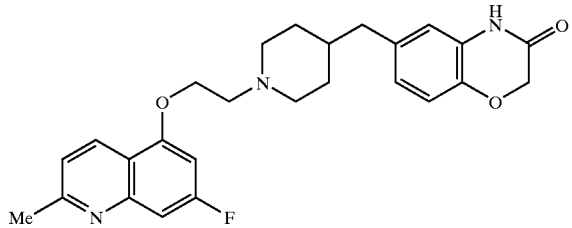

A solution or 2-(5-(7-fluoro-2-methyl)quinolinyl) oxyethyl bromide (0.10 g, 0.35 mmol), 6-(4-piperidinylmethyl)-4H-benzo[1,4]-oxazin-3-one hydrochloride (0.10 g 0.35 mmol) and diisopropylamine (0.25 mL, 1.44 mmol) in isopropyl alcohol (10 mL) was heated at reflux for 48 h. cooled and evaporated in vacuo. The residue was partitioned between dichloromethane (5 mL) and water (5 mL). The organic layer was added onto a pre-packed silica column (10 g) which was eluted with 0–20% methanol in ethyl acetate to give the title compound (0.068 g, 43%) as a colourless oil.

Mass spectrum (API$^+$): Found 450 (MH$^+$). C$_{26}$H$_{28}$FN$_3$O$_3$ requires 449.

$^1$H NMR (CDCl$_3$) δ:1.32 (2H, m), 1.48 (1H, m), 1.63 (2H, m), 2.13 (2H, m), 2.45 (2H, m), 2.70 (3H, s), 2.92 (2H, m), 3.03 (2H, m), 4.24 (2H, m), 4.57 (2H, s), 6.57 (2H, m), 6.72 (1H, dd, J=8, 2 Hz), 6.86 (1H, d, J=8 Hz), 7.18 (2H, m), 8.33 (1H, d, J=9 Hz), 9.17 (1H, br s).

EXAMPLE 147

6-{1-[2-(6-Fluoro-2-methyl-quinolin-5-yloxy)-ethyl]-piperidin-4-ylmethyl}-4H-benzo[1,4]oxazin-3-one (E147)

The title compound was prepared in a similar manner to Example 3.

Mass spectrum (API): Found 450 (MH$^+$). C$_{26}$H$_{28}$FN$_3$O$_3$ requires 449.

$^1$H NMR (CDCl$_3$) δ: 1.33 (2H, m), 1.49 (1H, m), 1.62 (2H, m), 2.04 (2H, m), 2.46 (2H, m), 2.72 (3H, s), 2.81 (2H, m), 3.00 (2H, m), 4.37 (2H, m), 4.60 (2H, s), 6.58 (1H, d, J=2H), 6.74 (1H, dd, J=8 Hz, 2 Hz), 6.88 (1H, d, J=8 Hz), 7.28 (1H, d, J=9 Hz), 7.44 (1H, m), 7.70 (1H, m), 8.42 (1H, d, J=9 Hz), 8.51 (1H, bs).

EXAMPLE 148

6-{4-[2-(6-Fluoro-2-methyl-quinolin-5-yloxy)-ethyl]-piperazin-1-ylmethyl}-4H-benzo[1,4]oxazin-3-one (E148)

The title compound was prepared in a similar manner to Example 3

Mass spectrum (API): Found 451 (MH$^+$). C$_{25}$H$_{27}$FN$_4$O$_3$ requires 450.

¹H NMR (CDCl₃) δ: 2.48 (4H, bs), 2.60 (4H, bs), 2.73 (3H, s), 2.84 (2H, m), 3.43 (2H, s), 4.38 (2H, m), 4.60 (2H, s), 6.79 (1H, s), 6.91 (2H, s), 7.28 (1H, d, J=9 Hz), 7.44 (1H, m), 7.70 (1H, m), 7.87 (1H, bs), 8.48 (1H, d, J=9 Hz).

EXAMPLE 149

6-{1-[2-(7,8-Difluoro-2-methyl-quinolin-5-yloxy)-ethyl]-piperidin-4-ylmethyl}-4H-benzo[1,4]oxazin-3-one (E149)

The title compound was prepared in a similar manner to Example 3

Mass spectrum (API): Found 468 (MH⁺). $C_{26}H_{27}F_2N_3O_3$ requires 467.

¹H NMR (CDCl₃) δ: 1.33 (2H, m), 1.47 (1H, m), 1.63 (2H, m), 2.12 (2H, m), 2.46 (2H, m), 2.77 (3H, s), 2.88 (2H, m), 3.02 (2H, m), 4.34 (2H, m), 4.59 (2H, s), 6.56 (1H, d, J=2 Hz), 6.74 (1H, dd, J=8 Hz, 2 Hz), 6.88 (1H, d, J=8 Hz), 7.00 (1H, m), 7.26 (1H, d, J=9 Hz), 8.19 (2H, m).

EXAMPLE 150

6-{4-[2-(7,8-Difluoro-2-methyl-quinolin-5-yloxy)-ethyl]-piperazin-1-ylmethyl}-4H-benzo[1,4]oxazin-3-one (E150)

The title compound was prepared in a similar manner to Example 3

Mass spectrum (API): Found 469 (MH⁺). $C_{25}H_{26}F_2N_4O_3$ requires 468.

¹H NMR (CDCl₃) δ: 2.48 (4H, bs), 2.64 (4H, bs), 2.77 (3H, s), 2.87 (2H, m), 3.42 (2H, s), 4.34 (2H, m), 4.60 (2H, s), 6.81 (1H, s), 6.90 (2H, m), 6.99 (1H, m), 7.26 (1H, d, J=9 Hz), 8.19 (1H, dd, J=9 Hz, 1 Hz), 8.51 (1H, bs).

EXAMPLE 151

6-{1-[2-(7-Iodo-2-methyl-quinolin-5-yloxy)-ethyl]-piperidin-4-ylmethyl}-4H-benzo[1,4]oxazin-3-one (E115)

The title compound was prepared in a similar manner to Example 3

Mass spectrum (API): Found 558 (MH⁺). $C_{26}H_{28}IN_3O_3$ requires 557.

EXAMPLE 152

2-Methyl-5-{2-[4-(3-oxo-3,4-dihydro-2H-benzo[1,4]oxazin-6-ylmethyl)-piperidin-1-yl]-ethoxy}-quinoline-7-carbonitrile (E152)

A mixture of 6-{1-[2-(7-Iodo-2-methyl-quinolin-5-yloxy)-ethyl]-piperidin-4-ylmethyl}-4H-benzo[1,4]oxazin-3-one (155 mg, 0.28 mmol) and copper (I) cyanide (50 mg, 0.56 mmol) in N-methylpyrrolidinione (2 mL) was stirred at 90° C. for 18 hrs. Upon cooling to room temperature the reaction mixture was partitioned between dichloromethane (5 mL) and ammonia (0.880, 5 mL). The organic layer was separated and applied directly to a 10 g pre-packed silica column eluting with 0–20% methanol in ethyl acetate to afford the title compound as a yellow oil (30 mg, 23%).

Mass spectrum (API): Found 457 (MH⁺). $C_{25}H_{26}F_2N_4O_3$ requires 456.

The following compounds were prepared from 6-(4-(1-(2-(5-(2-methyl)quinolinyloxy)ethyl)piperazinyl)methyl)-4H-benzo[1,4]oxazin-3-one (E115) and a suitable alkylating agent using a procedure similar to that described in Description 7.

TABLE 7

| Example | R | Mass spectrum (API⁺) |
|---|---|---|
| E153 | ethyl | Found 461 (MH⁺). C27H32N4O3 requires 460. |
| E154 | 1-propyl | Found 475 (MH⁺). C28H34N4O3 requires 474. |
| E155 | 1-butyl | Found 489 (MH⁺). C29H36N4O3 requires 488. |
| E156 | 2-methyl-1-propyl | Found 489 (MH⁺). C29H36N4O3 requires 488. |
| E157 | benzyl | Found 523 (MH⁺). C32H34N4O3 requires 522. |
| E158 | phenethyl | Found 537 (MH⁺). C32H36N4O3 requires 536. |

EXAMPLE 159

4-Ethyl-6-{1-[2-(2-methyl-quinolin-5-yloxy)-ethyl]-piperidin-4-ylmethyl}-4H-benzo[1,4]oxazin-3-one (E159)

The title compound was prepared using a similar procedure to that described in Description 7

Mass spectrum (API): Found 460 (MH⁺). $C_{28}H_{33}N_3O_3$ requires 459.

¹H NMR (CDCl₃) δ: 1.28 (3H, t J 7.1), 1.35–1.40 (3H, m), 1.59–1.66 (2H, m), 2.19 (2H, br t J 11), 2.52 (2H, d, J 6.6), 2.73 (3H, s), 2.97 (2H, t J 5.7), 3.07–3.11 (2H, m), 3.97 (2H, q J 7.2), 4.30 (2H, t J 5.7), 4.56 (2H, s), 6.56–6.81 (3H, m), 6.86–6.91 (1H, m), 7.22–7.26 (1H, m), 7.51–7.62 (2H, m), 8.41 (1H, d, J 8.5).

EXAMPLE 160

7,8-Difluoro-6-(4-(1-(2-(5-(2-methyl)quinolinyloxy)ethyl)piperazinyl)methyl)-4H-benzo[1,4]oxazin-3-one (E160)

The title compound was prepared using a similar procedure to that described in Description 16. The starting compound was 2,3-difluoro-4-hydroxy-benzoic acid methyl ester which was converted to D51 (see D51) and then underwent the sequential reactions described under D52–56.

Mass spectrum (API⁺): Found 469 (MH⁺). $C_{25}H_{26}F_2N_4O_3$ requires 468.

¹H NMR (CDCl₃) δ: 1.59 (4H, m), 2.50–2.70 (4H, m), 2.73 (3H, m), 3.51 (2H, m), 4.29 (2H, m), 4.66 (2H, s), 6.60 (1H, m), 6.80 (1H, m), 6.92 (2H, s), 7.24 (1H, m), 7.50–7.65 (2H, m), 7.87 (1H, br s), 8.43 (1H, m).

EXAMPLE 161

8-Fluoro-6-(4-(1-(2-(5-(2-methyl)quinolinyloxy)ethyl)piperidinyl)methyl)-4H-benzo[1,4]oxazin-3-one (E161)

The title compound was prepared in a similar manner to Example 3.

Mass spectrum (API⁺): Found 450 (MH⁺). $C_{26}H_{28}FN_3O_3$ requires 449.

¹H NMR (CDCl₃) δ: 1.25–1.38 (2H, m), 1.45–1.55 (1H, m), 1.65–1.75 (2H, m), 2.16 (2H, m), 2.44 (2H, d, J=7 Hz), 2.73 (3H, s), 2.95 (2H, t, J=6 Hz), 3.06 (2H, m), 4.28 (2H, t, J=6 Hz), 4.65 (2H, s), 6.34 (1H, s), 6.60 (1H, dd, J=7.2 Hz), 6.79 (1H, d, J=7 Hz), 7.24 (1H, d, J=8 Hz), 7.50–7.64 (2H, m), 7.74 (1H, br s), 8.42 (1H, d, J=8 Hz).

EXAMPLE 162

8-Fluoro-4-methyl-6-(4-(1-(2-(5-(2-methyl) quinolinyloxy)ethyl)piperidinyl)methyl)-4H-benzo [1,4]oxazin-3-one (E162)

The title compound was prepared in a similar manner to Example 3.

Mass spectrum (API⁺): Found 464 (MH⁺). $C_{27}H_{30}FN_3O_3$ requires 463.

¹H NMR (CDCl₃) δ: 1.40 (2H, m), 1.50–1.65 (1H, m), 1.65–1.70 (2H, m), 2.20 (2H, m), 2.50 (2H, d, J=7 Hz), 2.74 (3H, s), 2.90–3.20 (4H, m), 3.34 (3H, s), 4.30 (2H, s), 4.65 (2H, m), 6.51 (1H, s), 6.65 (1H, d, J=8 Hz), 6.80 (1H, d, J=8 Hz), 7.24 (1H, d, J=8 Hz), 7.50–7.60 (2H, m), 8.42 (1H, d, J=8 Hz).

EXAMPLE 163

7-Fluoro-6-(4-(1-(2-(5-(2-methyl)quinolinyloxy) ethyl)piperidinyl)methyl)-4H-benzo[1,4]oxazin-3-one (E163)

The title compound was prepared in a similar manner to Example 3.

Mass spectrum (API⁻): Found 448 ([M−H]⁻). $C_{26}H_{28}FN_3O_3$ requires 449.

¹NMR (CDCl₃) δ: 1.25–1.38 (1H, m), 1.50–1.60 (1H, m), 1.60–1.70 (2H, m), 2.14 (2H, m), 2.49 (2H, d, J=7 Hz), 2.73 (3H, s), 2.93 (2H, t, J=6 Hz), 3.04 (2H, m): 4.27 (2H, t, J=6 Hz), 4.58 (2H, s), 6.52 (1H, d, J=7 Hz), 6.69 (1H, d, J=10 Hz), 6.80 (1H, d, J=7 Hz), 7.24 (1H, d, J=8 Hz), 7.50–7.60 (2H, m), 7.61 (1H, br s), 8.42 (1H, d, J=8 Hz).

The following compounds (E164–167) were prepared in a similar manner to Example 3:

EXAMPLE 164

8-Fluoro-6-(4-(1-(2-(5-(2-Methyl)quinazolinyloxy) ethyl)piperidinyl)methyl)-4H-benzo[1,4]oxazin-3-one (E164)

EXAMPLE 165

7-Fluoro-6-(4-(1-(2-(5-(2-Methyl)quinazolinyloxy) ethyl)piperidinyl)methyl)-4H-benzo[1,4]-oxazin-3-one (E165)

EXAMPLE 166

8-Fluoro-6-(4-(1-(2-(5-(7-Chloro-2-methyl) quinolinyloxy)ethyl)piperidinyl)methyl)-4H-benzo [1,4]oxazin-3-one (E166)

EXAMPLE 167

7-Fluoro-6-(4-(1-(2-(5-(7-Chloro-2-methyl) quinolinyloxy)ethyl)piperidinyl)methyl)-4H-benzo [1,4]oxazin-3-one (E167)

What is claimed is:

1. A compound of formula (I) and/or a pharmaceutically acceptable salt thereof:

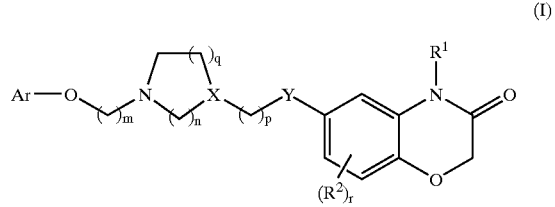

(I)

in which

Ar is phenyl, naphthyl, a monocyclic heteroaromatic group or a bicyclic heteroaromatic group, said Ar group being optionally substituted by 1–4 substituents, which may be the same or different, and which are selected from the group consisting of:

halogen, hydroxy, cyano, nitro, trifluoromethyl, trifluoromethoxy, $C_{1-6}$alkyl, trifluoromethanesulfonyloxy, pentafluoroethyl, $C_{1-6}$alkoxy, aryl$C_{1-6}$alkoxy, $C_{1-6}$alkylthio, $C_{1-6}$alkyl, $C_{3-7}$cycloalkyl$C_{1-6}$alkoxy, $C_{1-6}$alkanoyl, $C_{1-6}$alkoxycarbonyl, $C_{1-6}$alkylsulfonyl, $C_{1-6}$alkylsulfinyl, $C_{1-6}$alkylsulfonyloxy, $C_{1-6}$alkylsulfonyl$C_{1-6}$alkyl, arylsulfonyl, arylsulfonyloxy, arylsulfonyl$C_{1-6}$alkyl, $C_{1-6}$alkylsulfonamido, $C_{1-6}$alkylamino, $C_{1-6}$alkylsulfonamido$C_{1-6}$alkyl, $C_{1-6}$alkylamido$C_{1-6}$alkyl, arylsulfonamido, arylcarboxamido, arylsulfonamido$C_{1-6}$alkyl, arylcarboxamido$C_{1-6}$alkyl, aroyl, aroyl$C_{1-6}$alkyl, aryl$C_{1-6}$alkanoyl, a group $R^3OCO(CH_2)_s$, $R^3CON(R^4)(CH_2)_s$, $R^3R^4NCO(CH_2)_s$ or $R^3R^4NSO_2(CH_2)_s$ where each of $R^3$ and $R^4$ independently represents a hydrogen atom or $C_{1-4}$alkyl or $R^3$ and $R^4$ form part of a $C_{3-6}$azacyloalkane or $C_{3-6}$(2-oxo)azacycloalkane ring and s represents zero or an integer from 1 to 4, and a group $Ar^1$-Z, wherein Z represents a single bond, O, S or $CH_2$ and $Ar^1$ represents a phenyl or a monocyclic heteroaromatic group, said $Ar^1$ group being optionally substituted by 1–3 substituents, which may be the same or different, and which are selected from the group consisting of: a halogen, hydroxy, cyano, trifluoromethyl, $C_{1-6}$alkyl, $C_{1-6}$alkoxy or $C_{1-6}$alkanoyl;

when Ar is a phenyl or a monocyclic heteroaromatic group, substituents positioned ortho to one another may be linked to form a 5- or 6- membered ring selected from 2,3-dihydrobenzo[b]furanyl, 3,4-dihydro-2H-benzo[b]pyranyl, 2,2-dimethyl-2,3-dihydrobenzo[b]furanyl, 2,2-dimethyl-3,4-dihydro-2H-benzo[b]pyranyl, or 5-oxo-5,6,7,8-tetrahydronaphthyl, said 5- or 6- membered ring being optionally further substituted as defined above;

$R^1$ is hydrogen, $C_{1-6}$alkyl, $C_{3-6}$alkenyl, $C_{3-6}$alkynyl or aryl$C_{1-6}$alkyl;

$R^2$ is halogen, $C_{1-6}$alkyl, cyano, $CF_3$, $C_{1-6}$alkanoyl, $C_{1-6}$alkoxy or hydroxy;

X is CH or N;

Y is a single bond, O, or C=O;

p is 0, 1 or 2;

r is 0, 1, 2 or 3;

m is 2, 3 or 4;

n and q are independently 1 or 2.

2. A compound according to claim 1 in which Ar is phenyl, naphthyl, indolyl, quinolinyl, quinazolinyl, indazolyl, isoquinolinyl, cinnolinyl or benzofuranyl, said groups being optionally substituted as defined in claim 1.

3. A compound according to claim 1, in which Ar is substituted by halogen, $C_{1-6}$alkyl, cyano, $CF_3$, $C_{1-6}$alkoxy, $C_{1-6}$alkanoyl or a group $Ar^1$-Z as defined in claim 1.

4. A compound according to claim 3, in which $Ar^1$ is a monocyclic heteroaromatic group, optionally substituted as defined in claim 1, and Z is a single bond.

5. A compound according to claim 1 in which Ar is 4-indolyl, 4-indolyl(2-CN), 5-quinolinyl, 5-quinolinyl(2-methyl), 8-quinolinyl, 1-isoquinolinyl, naphthyl, phenyl(2-CN), phenyl(2,3-dichloro), phenyl(3-Br), phenyl(3-methyl), phenyl(3-$CF_3$), phenyl(2-propyl), phenyl(2-CN, 4-F), phenyl(2-(5-isoxazolyl), phenyl(3-ethyl-4-Cl), 2,2-dimethyl-2,3-dihydrobenzo[b]furan-7-yl, (5-F)-2,2-dimethyl-2,3-dihydrobenzo[b]furan-7-yl, (6-F)-3,4-dihydro-2H-benzo[b]pyranyl, (2,2-dimethyl)3,4-dihydro-2-benzo[b]pyranyl, 5-oxo-5,6,7,8-tetrahydronaphth-1-yl, 7-(2, 3-dihydrobenzofuranyl), 7-(2-methyl)benzo[b]furanyl, 7-benzo[b]furanyl, 5-quinolinyl(2-methyl, 8-Cl), 5-quinolinyl(2-methyl, 8-F), 5-quinolinyl(2-methyl, 7-Cl), 5-quinolinyl(2-methyl, 7-F) or 5-quinazolinyl(2-methyl).

6. A compound according to claim 1, wherein r is 0, 1 or 2.

7. A compound according to claim 1, wherein $R^2$ is halogen.

8. A compound according to claim 1, in which $R^1$ is hydrogen or methyl.

9. A compound according to claim 1, in which m is 2.

10. A compound according to claim 1, which is:

6-(4-(1-(2-(4-1H-Indolyloxy)ethyl)piperidinyl)oxy)-4H-benzo[1,4]oxazin-3-one;

6-(4-(1-(2-(4-(2-Cyano)-1H-indolyloxy)ethyl)piperidinyl)oxy)-4H-benzo[1,4]oxazin-3-one;

6-(4-(1-(3-(2-(5-Isoxazolyl)phenoxy)propyl)piperidinyl)oxy)-4H-benzo[1,4]oxazin-3-one;

6-(4-(1-(2-(5-Quinolinyloxy)ethyl)piperidinyl)methyl)-4H-benzo[1,4]oxazin-3-one;

6-(4-(1-(3-(2-Cyanophenoxy)propyl)piperidinyl)oxy)-4H-benzo[1,4]oxazin-3-one;

6-(4-(1-(3-(7-(2,2-Dimethyl-2,3-dihydro)benzo[b]furanyloxy)propyl)piperidinyl)-oxy)-4H-benzo[1,4]oxazin-3-one;

6-(4-(1-(2-(7-(2,2-Dimethyl-2,3-dihydro)benzo[b]furanyloxy)ethyl)piperidinyl)oxy)-4-methyl-4H-benzo[1,4]oxazin-3-one;

6-(4-(1-(2-(1-naphthyloxy)ethyl)piperidinyl)oxy)-4-methyl-4H-benzo[1,4]oxazin-3-one;

(±)-6-(3-(1-(3-(2-Cyanophenoxy)propyl)piperidinyl)methoxy)-4H-benzo[1,4]oxazin-3-one;

(±)-6-(3-(1-(3-(2-Cyanophenoxy)propyl)pyrrolidinyl)methoxy)-4H-benzo[1,4]oxazin-3-one;

6-(4-(1-(3-(2-(5-Isoxazolyl)phenoxy)propyl)piperazinyl)methyl)-4H-benzo[1,4]oxazin-3-one;

6-(4-(1-(2-(5-(2-Methyl)quinolinyloxy)ethyl)piperidinyl)methyl)-4H-benzo[1,4]oxazin-3-one;

6-(4-(1-(2-(5-(3-Methyl)quinolinyloxy)ethyl)piperidinyl)methyl)-4H-benzo[1,4]oxazin-3-one;

6-(4-(1-(2-(5-Cinnolinyloxy)ethyl)piperidinyl)methyl)-4H-benzo[1,4]oxazin-3-one;

6-(4-(1-(2-(4-(1,2-Dihydro)benzo[b]furanyloxy)ethyl)piperidinyl)methyl)-4H-benzo[1,4]oxazin-3-one;

6-(4-(1-(2-(4-(1H)-Indazolyloxy)ethyl)piperidinyl)methyl)-4H-benzo[1,4]oxazin-3-one;

6-(4-(1-(2-(5-(2-Methyl)quinolinyloxy)ethyl)piperidinyl)oxy)-4H-benzo[1,4]oxazin-3-one;

4-Methyl-6-(4-(1-(2-(5-(2-methyl)quinolinyloxy)ethyl)piperidinyl)oxy)-4H-benzo[1,3]oxazin-3-one;

6-(4-(1-(2-(5-(2-Methyl)quinolinyloxy)ethyl)piperazinyl)methyl)-4H-benzo[1,4]oxazin-3-one;

6-(4-(1-(3-(5-(2-Methyl)quinolinyloxy)propyl)piperidinyl)methyl)-4H-benzo[1,4]oxazin-3-one;

6-(4-(1-(3-(5-(2-Methyl)quinolinyloxy)propyl)piperazinyl)methyl)-4H-benzo[1,4]oxazin-3-one;

6-(4-(1-(3-(5-(2-Methyl)quinolinyloxy)propyl)piperidinyl)oxy)-4H-benzo[1,4]oxazin-3-one;

4-Methyl-6-(4-(1-(3-(5-(2-methyl)quinolinyloxy)propyl)piperidinyl)oxy)-4H-benzo[1,4]oxazin-3-one;

4-Methyl-6-(4-(1-(2-(5-(2-methyl)quinolinyloxy)ethyl)piperidinyl)methyl)-4H-benzo[1,4]oxazin-3-one;

6-(4-(1-(2-(5-(8-Chloro-2-methyl)quinolinyloxy)ethyl)piperidinyl)methyl)-4H-benzo[1,4]oxazin-3-one;

4-Methyl-6-(4-(1-(3-(5-(2-methyl)quinolinyloxy)propyl)piperidinyl)-methyl)-4H-benzo[1,4]oxazin-3-one;

6-(4-(1-(2-(5-(8-Chloro-2-methyl)quinolinyloxy)ethyl)piperidinyl)methyl)-4-methyl-4H-benzo[1,4]oxazin-3-one;

6-(4-(1-(2-(5-(8-Fluoro-2-methyl)quinolinyloxy)ethyl)piperidinyl)methyl)-4H-benzo[1,4]oxazin-3-one;

6-(4-(1-(2-(5-(8-Fluoro-2-methyl)quinolinyloxy)ethyl)piperidinyl)methyl)-4-methyl-4H-benzo[1,4]oxazin-3-one;

6-(4-(1-(2-(5-(8-Fluoro-2-methyl)quinolinyloxy)ethyl)piperidinyl)oxy)-4H-benzo[1,4]oxazin-3-one;

6-(4-(1-(2-(5-(8-Fluoro-2-methyl)quinolinyloxy)ethyl)piperidinyl)oxy)-4-methyl-4H-benzo[1,4]oxazin-3-one;

6-(4-(1-(2-(5-(7-Chloro-2-methyl)quinolinyloxy)ethyl)piperidinyl)methyl)-4H-benzo[1,4]oxazin-3-one;

6-(4-(1-(2-(5-(7-Chloro-2-methyl)quinolinyloxy)ethyl)piperidinyl)methyl)-4-methyl-4H-benzo[1,4]oxazin-3-one;

6-(4-(1-(2-(5-(7-Chloro-2-methyl)quinolinyloxy)ethyl)piperidinyl)oxy)-4H-benzo[1,4]oxazin-3-one;

6-(4-(1-(2-(5-(7-Chloro-2-methyl)quinolinyloxy)ethyl)piperidinyl)oxy)-4-methyl-4H-benzo[1,4]oxazin-3-one;

6-(4-(1-(2-(5-(7-Chloro-2-methyl)quinolinyloxy)ethyl)piperazinyl)methyl)-4H-benzo[1,4]oxazin-3-one;

6-(4-(1-(3-(5-(7-Chloro-2-methyl)quinolinyloxy)propyl)piperidinyl)oxy)-4H-benzo[1,4]oxazin-3-one;

6-(4-(1-(3-(5-(7-Chloro-2-methyl)quinolinyloxy)propyl)piperidinyl)oxy)-4-methyl-4H-benzo[1,4]oxazine-3-one;

6-(4-(1-(2-(5-(2-Methyl)quinolinyloxy)ethyl)piperidinyl)methyl)-4-(2-propyl)-4H-benzo[1,4]oxazin-3-one;

6-(4-(1-(2-(5-(2-Methyl)quinazolinyloxy)ethyl)piperidinyl)methyl)-4H-benzo[1,4]-oxazin-3-one;

6-(4-(1-(2-(5-(7-Fluoro-2-methyl)quinolinyloxy)ethyl)piperidinyl)methyl)-4H-benzo[1,4]oxazin-3-one;

7-Fluoro-6-(4-(1-(2-(5-(2-methyl)quinolinyloxy)ethyl)piperidinyl)methyl)-4H-benzo[1,4]oxazin-3-one;

8-Fluoro-4-methyl-6-(4-(1-(2-(5-(2-methyl) quinolinyloxy)ethyl)piperidinyl)methyl)-4H-benzo[1,4]oxazin-3-one;

8-Fluoro-6-(4-(1-(2-(5-(2-methyl)quinolinyloxy)ethyl) piperidinyl)methyl)-4H-benzo[1,4]oxazin-3-one;

7,8-Difluoro-6-(4-(1-(2-(5-(2-methyl)quinolinyloxy) ethyl)piperazinyl)methyl)-4H-benzo[1,4]oxazin-3-one; or 4-Ethyl-6-{1-[2-(2-methyl-quinolin-5-yloxy)-ethyl]-piperidin-4-ylmethyl}-4H-benzo[1,4]oxazin-3-one and/or a pharmaceutically acceptable salt thereof.

11. A process for the preparation of a compound of formula (I) or a pharmaceutically acceptable salt thereof, which process comprises:

(a) the coupling of a compound of formula (II):

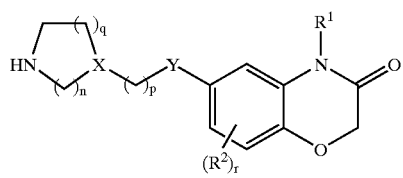

(II)

in which $R^1$, $R^2$, Y, n, p, q and r are defined in formula (I), with a compound of formula (III):

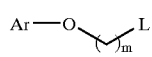

(III)

in which Ar and m are as defined for formula (I) and L is a leaving group; or (b) reacting a compound of formula (II) as defined above with a compound of formula (IV)

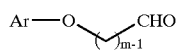

(IV)

in which Ar and m are defined in formula (I), in the presence of a reducing agent; or (c) for a compound of formula (I) wherein X is N, reacting a compound of formula (V):

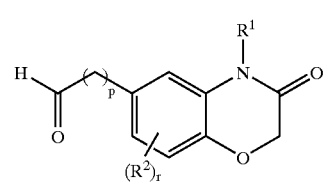

(V)

in which p, $R^2$, r and $R^1$ are as defined in formula (I), with a compound of formula (VI):

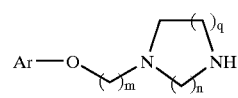

(VI)

in which Ar, m, q and n are as defined in formula (I), in the presence of a reducing agent;

and optionally thereafter for each of process (a), (b) or (c):
i) removing any protecting groups, and/or
ii) forming a pharmaceutically acceptable salt.

12. A pharmaceutical composition which comprises a compound according to claim 1 and a pharmaceutically acceptable carrier or excipient.

13. A process for preparing a pharmaceutical composition that comprises mixing a compound according to claim 1 and a pharmaceutically acceptable carrier or excipient.

14. A method of treating a disease state selected from: depression, generalized anxiety, schizophrenia, panic disorder, agoraphobia, social phobia, obsessive compulsive disorder, post-traumatic stress disorder, pain, anorexia, bulimia, sexual dysfunction, dyssomnia, insomnia, sleep apnea, narcolepsy, withdrawal from abuse of drugs, neuroleptic-induced Parkinsonism and/or tardive dyskinesias which comprises administering a safe and therapeutically effective amount to a patient in need thereof of a compound according to claim 1 or a pharmaceutically acceptable salt thereof.

15. A method of treating a disease state selected from: depression, generalized anxiety, schizophrenia, panic disorder, agoraphobia, social phobia, obsessive compulsive disorder, post-traumatic stress disorder, pain, anorexia, bulimia, sexual dysfunction, dyssomnia, insomnia, sleep apnea, narcolepsy, withdrawal from abuse of drugs, neuroleptic-induced Parkinsonism and/or tardive dyskinesias which comprises administering a safe and therapeutically effective amount to a patient in need thereof of a composition according to claim 12.

16. A method according to claim 15, wherein the disease state is selected from: depression, generalized anxiety, panic disorder, agoraphobia, social phobia, obsessive compulsive disorder and/or post-traumatic stress disorder.

* * * * *